US009577200B2

(12) United States Patent
Ma et al.

(10) Patent No.: US 9,577,200 B2
(45) Date of Patent: *Feb. 21, 2017

(54) ORGANIC ELECTROLUMINESCENT MATERIALS AND DEVICES

(71) Applicant: UNIVERSAL DISPLAY CORPORATION, Ewing, NJ (US)

(72) Inventors: Bin Ma, Plainsboro, NJ (US); Yonggang Wu, Ewing, NJ (US); Chun Lin, Yardley, PA (US); Raymond Kwong, Fo Tan (HK)

(73) Assignee: UNIVERSAL DISPLAY CORPORATION, Ewing, NJ (US)

(*) Notice: Subject to any disclaimer, the term of this patent is extended or adjusted under 35 U.S.C. 154(b) by 0 days.

This patent is subject to a terminal disclaimer.

(21) Appl. No.: 14/838,450

(22) Filed: Aug. 28, 2015

(65) Prior Publication Data

US 2015/0372243 A1 Dec. 24, 2015

Related U.S. Application Data

(60) Continuation of application No. 14/335,076, filed on Jul. 18, 2014, now Pat. No. 9,153,786, which is a division of application No. 13/714,872, filed on Dec. 14, 2012, now Pat. No. 8,822,708, which is a division of application No. 12/672,198, filed as application No. PCT/US2008/072499 on Aug. 7, 2008, now Pat. No. 8,367,850.

(60) Provisional application No. 60/963,944, filed on Aug. 8, 2007, provisional application No. 61/017,506, filed on Dec. 28, 2007, provisional application No. 61/017,391, filed on Dec. 28, 2007.

(51) Int. Cl.
| | |
|---|---|
| *C07D 333/76* | (2006.01) |
| *H01L 51/00* | (2006.01) |
| *C07D 307/91* | (2006.01) |
| *C07D 409/04* | (2006.01) |
| *C07C 15/38* | (2006.01) |
| *C09B 57/00* | (2006.01) |
| *C09K 11/06* | (2006.01) |
| *H05B 33/14* | (2006.01) |
| *H01L 51/50* | (2006.01) |

(52) U.S. Cl.
CPC .......... *H01L 51/0074* (2013.01); *C07C 15/38* (2013.01); *C07D 307/91* (2013.01); *C07D 333/76* (2013.01); *C07D 409/04* (2013.01); *C09B 57/00* (2013.01); *C09K 11/06* (2013.01); *H01L 51/004* (2013.01); *H01L 51/0054* (2013.01); *H01L 51/0058* (2013.01); *H01L 51/0061* (2013.01); *H01L 51/0067* (2013.01); *H01L 51/0071* (2013.01); *H01L 51/0073* (2013.01); *H01L 51/0085* (2013.01); *H05B 33/14* (2013.01); *C07C 2103/42* (2013.01); *C09K 2211/1007* (2013.01); *C09K 2211/1011* (2013.01); *H01L 51/0059* (2013.01); *H01L 51/0081* (2013.01); *H01L 51/5016* (2013.01); *H01L 51/5024* (2013.01)

(58) Field of Classification Search
CPC .......................... H01L 51/0074; C07D 333/76
See application file for complete search history.

(56) References Cited

U.S. PATENT DOCUMENTS

| | | | |
|---|---|---|---|
| 4,769,292 | A | 9/1988 | Tang et al. |
| 4,772,940 | A | 9/1988 | Wudl et al. |
| 5,061,569 | A | 10/1991 | VanSlyke et al. |
| 5,247,190 | A | 9/1993 | Friend et al. |
| 5,703,436 | A | 12/1997 | Forrest et al. |
| 5,707,745 | A | 1/1998 | Forrest et al. |
| 5,834,893 | A | 11/1998 | Bulovic et al. |
| 5,844,363 | A | 12/1998 | Gu et al. |
| 6,013,982 | A | 1/2000 | Thompson et al. |
| 6,087,196 | A | 7/2000 | Sturm et al. |
| 6,091,195 | A | 7/2000 | Forrest et al. |
| 6,097,147 | A | 8/2000 | Baldo et al. |
| 6,294,398 | B1 | 9/2001 | Kim et al. |
| 6,303,238 | B1 | 10/2001 | Thompson et al. |
| 6,337,102 | B1 | 1/2002 | Forrest et al. |
| 6,468,819 | B1 | 10/2002 | Kim et al. |
| 6,528,187 | B1 | 3/2003 | Okada |
| 6,687,266 | B1 | 2/2004 | Ma et al. |
| 6,835,469 | B2 | 12/2004 | Kwong et al. |
| 6,916,554 | B2 | 7/2005 | Ma et al. |
| 6,921,915 | B2 | 7/2005 | Takiguchi et al. |
| 7,087,321 | B2 | 8/2006 | Kwong et al. |
| 7,090,928 | B2 | 8/2006 | Thompson et al. |
| 7,154,114 | B2 | 12/2006 | Brooks et al. |

(Continued)

FOREIGN PATENT DOCUMENTS

| | | |
|---|---|---|
| EP | 0650955 | 5/1995 |
| EP | 0742197 | 11/1996 |

(Continued)

OTHER PUBLICATIONS

Notice of Reasons for Rejection issued Dec. 21, 2015 in corresponding Japanese Patent Application No. 2014-18814.
Adachi, Chihaya et al., "Organic Electroluminescent Device Having a Hole Conductor as an Emitting Layer," Appl. Phys. Lett., 55(15): 1489-1491 (1989).
Adachi, Chihaya et al., "Nearly 100% Internal Phosphorescence Efficiency in an Organic Light Emitting Device," J. Appl. Phys., 90(10): 5048-5051 (2001).
Adachi, Chihaya et al., "High-Efficiency Red Electrophosphorescence Devices," Appl. Phys. Lett., 78(11)1622-1624 (2001).

(Continued)

*Primary Examiner* — Golam M M Shameem
(74) *Attorney, Agent, or Firm* — Duane Morris LLP

(57) ABSTRACT

Triphenylene containing benzo-fused thiophene compounds are provided. Additionally, triphenylene containing benzo-fused furan compounds are provided. The compounds may be useful in organic light emitting devices, particularly as hosts in the emissive layer of such devices, or as materials for enhancement layers in such devices, or both.

19 Claims, 3 Drawing Sheets

(56) References Cited

U.S. PATENT DOCUMENTS

| | | |
|---|---|---|
| 7,250,226 B2 | 7/2007 | Tokito et al. |
| 7,279,704 B2 | 10/2007 | Walters et al. |
| 7,332,232 B2 | 2/2008 | Ma et al. |
| 7,338,722 B2 | 3/2008 | Thompson et al. |
| 7,393,599 B2 | 7/2008 | Thompson et al. |
| 7,396,598 B2 | 7/2008 | Takeuchi et al. |
| 7,431,968 B1 | 10/2008 | Shtein et al. |
| 7,445,855 B2 | 11/2008 | Mackenzie et al. |
| 7,534,505 B2 | 5/2009 | Lin et al. |
| 8,367,850 B2 | 2/2013 | Ma et al. |
| 8,822,708 B2 | 9/2014 | Ma et al. |
| 8,968,887 B2 | 3/2015 | Ma et al. |
| 9,153,786 B2 * | 10/2015 | Ma .................. C07D 307/91 |
| 2002/0034656 A1 | 3/2002 | Thompson et al. |
| 2002/0064679 A1 | 5/2002 | Ishiskawa et al. |
| 2002/0134984 A1 | 9/2002 | Igarashi |
| 2002/0158242 A1 | 10/2002 | Son et al. |
| 2003/0105343 A1 | 6/2003 | Taylor et al. |
| 2003/0138657 A1 | 7/2003 | Li et al. |
| 2003/0151042 A1 | 8/2003 | Hueschen |
| 2003/0152802 A1 | 8/2003 | Tsuboyama et al. |
| 2003/0175553 A1 | 9/2003 | Thompson et al. |
| 2003/0230980 A1 | 12/2003 | Forrest et al. |
| 2004/0036077 A1 | 2/2004 | Ise |
| 2004/0076852 A1 | 4/2004 | Cheng et al. |
| 2004/0137267 A1 | 7/2004 | Igarashi et al. |
| 2004/0137268 A1 | 7/2004 | Igarashi et al. |
| 2004/0174116 A1 | 9/2004 | Lu et al. |
| 2005/0025993 A1 | 2/2005 | Thompson et al. |
| 2005/0112407 A1 | 5/2005 | Ogasawara et al. |
| 2005/0238919 A1 | 10/2005 | Ogasawara |
| 2005/0244673 A1 | 11/2005 | Satoh et al. |
| 2005/0260441 A1 | 11/2005 | Thompson et al. |
| 2005/0260449 A1 | 11/2005 | Walters et al. |
| 2006/0008670 A1 | 1/2006 | Lin et al. |
| 2006/0057426 A1 | 3/2006 | Itoh |
| 2006/0088728 A1 | 4/2006 | Kwong et al. |
| 2006/0202194 A1 | 9/2006 | Jeong et al. |
| 2006/0240279 A1 | 10/2006 | Adamovich et al. |
| 2006/0251923 A1 | 11/2006 | Lin et al. |
| 2006/0263635 A1 | 11/2006 | Ise |
| 2006/0280965 A1 | 12/2006 | Kwong et al. |
| 2007/0141387 A1 | 6/2007 | Nakano et al. |
| 2007/0190359 A1 | 8/2007 | Knowles et al. |
| 2007/0278938 A1 | 12/2007 | Yabunouchi et al. |
| 2008/0015355 A1 | 1/2008 | Schafer et al. |
| 2008/0018221 A1 | 1/2008 | Egen et al. |
| 2008/0106190 A1 | 5/2008 | Yabunouchi et al. |
| 2008/0124572 A1 | 5/2008 | Mizuki et al. |
| 2008/0220265 A1 | 9/2008 | Xia et al. |
| 2008/0297033 A1 | 12/2008 | Knowles et al. |
| 2009/0008605 A1 | 1/2009 | Kawamura et al. |
| 2009/0009065 A1 | 1/2009 | Nishimura et al. |
| 2009/0017330 A1 | 1/2009 | Iwakuma et al. |
| 2009/0030202 A1 | 1/2009 | Iwakuma et al. |
| 2009/0039776 A1 | 2/2009 | Yamada et al. |
| 2009/0045730 A1 | 2/2009 | Nishimura et al. |
| 2009/0045731 A1 | 2/2009 | Nishimura et al. |
| 2009/0101870 A1 | 4/2009 | Prakash et al. |
| 2009/0108737 A1 | 4/2009 | Kwong et al. |
| 2009/0115316 A1 | 5/2009 | Zheng et al. |
| 2009/0165846 A1 | 7/2009 | Johannes et al. |
| 2009/0167162 A1 | 7/2009 | Lin et al. |
| 2009/0179554 A1 | 7/2009 | Kuma et al. |

FOREIGN PATENT DOCUMENTS

| | | |
|---|---|---|
| EP | 1725079 | 11/2006 |
| EP | 1894923 | 3/2008 |
| EP | 1962354 | 8/2008 |
| EP | 2034538 | 3/2009 |
| JP | H05-109485 | 4/1993 |
| JP | H11-354281 | 12/1999 |
| JP | 2000156289 | 6/2000 |
| JP | 2000273055 | 10/2000 |
| JP | 201196182 | 7/2001 |
| JP | 2003109763 | 4/2003 |
| JP | 3424812 | 7/2003 |
| JP | 2004018665 | 1/2004 |
| JP | 200511610 | 1/2005 |
| JP | 2005047868 | 2/2005 |
| JP | 2005071983 | 3/2005 |
| JP | 2005259472 | 9/2005 |
| JP | 2006076995 | 3/2006 |
| JP | 2006143845 | 6/2006 |
| JP | 2006151844 | 6/2006 |
| JP | 2007027356 | 2/2007 |
| JP | 2007123392 | 5/2007 |
| JP | 2007126403 | 5/2007 |
| JP | 2007189001 | 7/2007 |
| JP | 2007254297 | 10/2007 |
| JP | 2008074939 | 4/2008 |
| WO | 0139234 | 5/2001 |
| WO | 0202714 | 1/2002 |
| WO | 0215645 | 2/2002 |
| WO | 03040257 | 5/2003 |
| WO | 03060956 | 7/2003 |
| WO | 2004093207 | 10/2004 |
| WO | 2004107822 | 12/2004 |
| WO | 2005014551 | 2/2005 |
| WO | 2005019373 | 3/2005 |
| WO | 2005030900 | 4/2005 |
| WO | 2005089025 | 9/2005 |
| WO | 2005123873 | 12/2005 |
| WO | 2006009024 | 1/2006 |
| WO | 2006056418 | 6/2006 |
| WO | 2006072002 | 7/2006 |
| WO | 2006082742 | 8/2006 |
| WO | 2006098120 | 9/2006 |
| WO | 2006100298 | 9/2006 |
| WO | 2006103874 | 10/2006 |
| WO | 2006114966 | 11/2006 |
| WO | 2006128800 | 12/2006 |
| WO | 2006130598 | 12/2006 |
| WO | 2006132173 | 12/2006 |
| WO | 2006137210 | 12/2006 |
| WO | 2007002683 | 1/2007 |
| WO | 2007004380 | 1/2007 |
| WO | 2007063754 | 6/2007 |
| WO | 2007063796 | 6/2007 |
| WO | 2008056746 | 5/2008 |
| WO | 2008101842 | 8/2008 |
| WO | 2008132085 | 11/2008 |
| WO | 2009000673 | 12/2008 |
| WO | 2009003898 | 1/2009 |
| WO | 2009008311 | 1/2009 |
| WO | 2009018009 | 2/2009 |
| WO | 2009050290 | 4/2009 |
| WO | 2009021126 | 5/2009 |
| WO | 2009062578 | 5/2009 |
| WO | 2009063833 | 5/2009 |
| WO | 2009066778 | 5/2009 |
| WO | 2009066779 | 5/2009 |
| WO | 2009086028 | 7/2009 |
| WO | 2009100991 | 8/2009 |

OTHER PUBLICATIONS

Aonuma, Masaki et al., "Material Design of Hole Transport Materials Capable of Thick-Film Formation in Organic Light Emitting Diodes," Appl. Phys. Lett., 90:183503-1-183503-3.

Baldo et al., Highly Efficient Phosphorescent Emission from Organic Electroluminescent Devices, Nature, vol. 395, 151-154, (1998).

Baldo et al., Very high-efficiency green organic light-emitting devices based on electrophosphorescence, Appl. Phys. Lett., vol. 75, No. 3, 4-6 (1999).

Gao, Zhicliang et al., "Bright-Blue Electroluminescence From a Silyl-Substituted ter-(phenylene-vinylene) derivative," Appl. Phys. Lett., 74(6): 865-867 (1999).

Guo, Tzung-Fang et al., "Highly Efficient Electrophosphorescent Polymer Light-Emitting Devices," Organic Electronics, 115-20 (2000).

(56) References Cited

OTHER PUBLICATIONS

Hamada, Yuji et al., "High Luminance in Organic Electroluminescent Devices with Bis(10-hydroxybenzo[h]quinolinato) beryllium as an Emitter," Chem. Lett., 905-906 (1993).
Holmes, R.J. et al., "Blue Organic Electrophosphorescence Using Exothermic Host-Guest Energy Transfer," Appl. Phys. Lett., 82(15):2422-2424 (2003).
Hu, Nan-Xing et al., "Novel High Tg Hole-Transport Molecules Based on Indolo[3,2-b]carbazoles for Organic Light-Emitting Devices," Synthetic Metals, 111-112:421-424 (2000).
Huang, Jinsong et al., "Highly Efficient Red-Emission Polymer Phosphorescent Light-Emitting Diodes Based on Two Novel Tris(1-phenylisoquinolinato-C2,N)iridium(III) Derivates," Adv. Mater., 19:739-743 (2007).
Huang, Wei-Sheng et al., "Highly Phosphorescent Bis-Cyclometalated Iridium Complexes Containing Benzoimidazole-Based Ligands," Chem. Mater., 16(12):2480-2488 (2004).
Hung, L.S. et al., "Anode Modification in Organic Light-Emitting Diodes by Low-Frequency Plasma Polymerization of CHF3," Appl. Phys. Lett., 78(5):673-675 (2001).
Ikai, Masamichi and Tokito, Shizuo, "Highly Efficient Phosphorescence From Organic Light-Emitting Devices with an Exciton-Block Layer," Appl. Phys. Lett., 79(2):156-158 (2001).
Ikeda, Hisao et al., "P-185 Low-Drive-Voltage OLEDs with a Buffer Layer Having Molybdenum Oxide," SID Symposium Digest, 37:923-926 (2006).
Inada, Hiroshi and Shirota, Yasuhiko, "1,3,5-Tris[4-(diphenylamino)phenyl]benzene and its Methylsubstituted Derivatives as a Novel Class of Amorphous Molecular Materials," J. Mater. Chem., 3(3):319-320 (1993).
Kanno, Hiroshi et al., "Highly Efficient and Stable Red Phosphorescent Organic Light-Emitting Device Using bis[2-(2-benzothiazoyl)phenolato]zinc(II) as host material," Appl. Phys. Lett., 90:123509-1-123509-3 (2007).
Kido, Junji et al., 1,2,4-Triazole Derivative as an Electron Transport Layer in Organic Electroluminescent Devices, Jpn. J. Appl. Phys., 32:L917-L920 (1993).
Kuwabara, Yoshiyuki et al., "Thermally Stable Multilayered Organic Electroluminescent Devices Using Novel Starburst Molecules, 4,4',4"-Tri(N-carbazolyl)triphenylamine (TCTA) and 4,4',4"-Tris(3-methylphenylphenyl-amino) triphenylamine (m-MTDATA), as Hole-Transport Materials," Adv. Mater., 6(9):677-679 (1994).
Kwong, Raymond C. et al., "High Operational Stability of Electrophosphorescent Devices," Appl. Phys. Lett., 81(1) 162-164 (2002).
Lamansky, Sergey et al., "Synthesis and Characterization of Phosphorescent Cyclometalated Iridium Complexes," Inorg. Chem., 40(7):1704-1711 (2001).
Lee, Chang-Lyoul et al., "Polymer Phosphorescent Light-Emitting Devices Doped with Tris(2-phenylpyridine) Iridium as a Triplet Emitter," Appl. Phys. Lett., 77(15):2280-2282 (2000).
Lo, Shih-Chun et al., "Blue Phosphorescence from Iridium(III) Complexes at Room Temperature," Chem. Mater., 18(21)5119-5129 (2006).
Ma, Yuguang et al., "Triplet Luminescent Dinuclear-Gold(I) Complex-Based Light-Emitting Diodes with Low Turn-On voltage," Appl. Phys. Lett., 74(10):1361-1363 (1999).
Mi, Bao-Xiu et al., "Thermally Stable Hole-Transporting Material for Organic Light-Emitting Diode an Isoindole Derivative," Chem. Mater., 15(16):3148-3151 (2003).
Nishida, Jun-ichi et al., "Preparation, Characterization, and Electroluminescence Characteristics of α-Diimine-type Platinum(II) Complexes with Perfluorinated Phenyl Groups as Ligands," Chem. Lett., 34(4): 592-593 (2005).
Niu, Yu-Hua et al., "Highly Efficient Electrophosphorescent Devices with Saturated Red Emission from a Neutral Osmium Complex," Chem. Mater., 17(13):3532-3536 (2005).
Noda, Tetsuya and Shirota,Yasuhiko, "5,5'-Bis(dimesitylboryl)-2,2"-bithiophene and 5,5"-Bis (dimesitylboryl)-2,2'5',2"-terthiophene as a Novel Family of Electron-Transporting Amorphous Molecular Materials," J. Am. Chem. Soc., 120 (37):9714-9715 (1998).
Okumoto, Kenji et al., "Green Fluorescent Organic Light-Emitting Device with External Quantum Efficiency of Nearly 10%," Appl. Phys. Lett., 89:063504-1-063504-3 (2006).
Palilis, Leonidas C., "High Efficiency Molecular Organic Light-Emitting Diodes Based on Silole Derivatives and Their Exciplexes," Organic Electronics, 4:113-121 (2003).
Paulose, Betty Marie Jennifer S. et al., "First Examples of Alkenyl Pyridines as Organic Ligands for Phosphorescent Iridium Complexes," Adv. Mater., 16(22):2003-2007 (2004).
Ranjan, Sudhir et al., "Realizing Green Phosphorescent Light-Emitting Materials from Rhenium(I) Pyrazolato Diimine Complexes," Inorg. Chem., 42(4):1248-1255 (2003).
Sakamoto, Youichi et al., "Synthesis, Characterization, and Electron-Transport Property of Perfluorinated Phenylene Dendrimers," J. Am. Chem. Soc., 122(8):1832-1833 (2000).
Salbeck, J. et al., "Low Molecular Organic Glasses for Blue Electroluminescence," Synthetic Metals, 91209-215 (1997).
Shirota, Yasuhiko et al., "Starburst Molecules Based on p-Electron Systems as Materials for Organic Electroluminescent Devices," Journal of Luminescence, 72-74:985-991 (1997).
Sotoyama, Wataru et al., "Efficient Organic Light-Emitting Diodes with Phosphorescent Platinum Complexes Containing N^C^ N-Coordinating Tridentate Ligand," Appl. Phys. Lett., 86:153505-1-153505-3 (2005).
Sun, Yiru and Forrest, Stephen R., "High-Efficiency White Organic Light Emitting Devices with Three Separate Phosphorescent Emission Layers," Appl. Phys. Lett., 91:263503-1-263503-3 (2007).
T. Östergård et al., "Langmuir-Blodgett Light-Emitting Diodes of Poly(3-Hexylthiophene) Electro-Optical Characteristics Related to Structure," Synthetic Metals, 87:171-177 (1997).
Takizawa, Shin-ya et al., "Phosphorescent Iridium Complexes Based on 2-Phenylimidazo[1,2- α]pyridine Ligands Tuning of Emission Color toward the Blue Region and Application to Polymer Light-Emitting Devices," Inorg. Chem., 46(10):4308-4319 (2007).
Tang, C.W. and VanSlyke, S.A., "Organic Electroluminescent Diodes," Appl. Phys. Lett., 51(12):913-915 (1987).
Tung, Yung-Liang et al., "Organic Light-Emitting Diodes Based on Charge-Neutral Ru II PHosphorescent Emitters," Adv. Mater., 17(8)1059-1064 (2005).
Van Slyke, S. A. et al., "Organic Electroluminescent Devices with Improved Stability," Appl. Phys. Lett., 69(15):2160-2162 (1996).
Wang, Y. et al., "Highly Efficient Electroluminescent Materials Based on Fluorinated Organometallic Iridium Compounds," Appl. Phys. Lett., 79(4):449-451 (2001).
Wong, Keith Man-Chung et al., A Novel Class of Phosphorescent Gold(III) Alkynyl-Based Organic Light-Emitting Devices with Tunable Colour, Chem. Commun., 2906-2908 (2005).
Wong, Wai-Yeung, "Multifunctional Iridium Complexes Based on Carbazole Modules as Highly Efficient Electrophosphors," Angew. Chem. Int. Ed., 45:7800-7803 (2006).
Government of India Patent Office, First Examination Report regarding corresponding Indian Application No. 1488/DELNP/2010 issued Apr. 30, 2015, pp. 1-2.
U.S. Appl. No. 60/963,944, filed Aug. 8, 2007.
U.S. Appl. No. 61/017,506, filed Dec. 28, 2007.
U.S. Appl. No. 61/017,391, filed Dec. 28, 2007.
Decision of Rejection issued on Jun. 27, 2016 for corresponding JP Application No. 2014-191683.
Office Action issued Aug. 9, 2016 in corresponding Korean Patent Application No. 10-2015-7008181.

* cited by examiner

Formula (IV)  Formula (V)  Formula (VI)

ORGANIC ELECTROLUMINESCENT MATERIALS AND DEVICES

This application is a continuation of U.S. application Ser. No. 14/335,076, filed Jul. 18, 2014, which is a continuation of U.S. application Ser. No. 13/714,872, filed Dec. 14, 2012, now U.S. Pat. No. 8,822,708, which is a divisional application of U.S. application Ser. No. 12/672,198, filed May 26, 2010, now U.S. Pat. No. 8,367,850, which is a §371 National Stage Entry of International Application Serial No. PCT/US2008/072499, filed Aug. 7, 2008, which claims priority to U.S. Provisional Application Ser. No. 60/963,944, filed Aug. 8, 2007, U.S. Provisional Application Ser. No. 61/017,506, filed Dec. 28, 2007, and U.S. Provisional Application Ser. No. 61/017,391, filed Dec. 28, 2007, the disclosures of which are expressly incorporated herein by reference in their entirety.

JOINT RESEARCH AGREEMENT

The claimed invention was made by, on behalf of, and/or in connection with one or more of the following parties to a joint university corporation research agreement: The Regents of the University of Michigan, Princeton University, University of Southern California, and Universal Display Corporation. The agreement was in effect on and before the date the claimed invention was made, and the claimed invention was made as a result of activities undertaken within the scope of the agreement.

FIELD OF THE INVENTION

The present invention relates to novel organic materials having a benzo-fused thiophene and/or a benzo-fused furan and a triphenylene. In particular, the materials have a dibenzothiophene and/or benzofuran and a triphenylene. The materials may be useful in light emitting devices (OLEDs).

BACKGROUND

Opto-electronic devices that make use of organic materials are becoming increasingly desirable for a number of reasons. Many of the materials used to make such devices are relatively inexpensive, so organic opto-electronic devices have the potential for cost advantages over inorganic devices. In addition, the inherent properties of organic materials, such as their flexibility, may make them well suited for particular applications such as fabrication on a flexible substrate. Examples of organic opto-electronic devices include organic light emitting devices (OLEDs), organic phototransistors, organic photovoltaic cells, and organic photodetectors. For OLEDs, the organic materials may have performance advantages over conventional materials. For example, the wavelength at which an organic emissive layer emits light may generally be readily tuned with appropriate dopants.

OLEDs make use of thin organic films that emit light when voltage is applied across the device. OLEDs are becoming an increasingly interesting technology for use in applications such as flat panel displays, illumination, and backlighting. Several OLED materials and configurations are described in U.S. Pat. Nos. 5,844,363, 6,303,238, and 5,707,745, which are incorporated herein by reference in their entirety.

One application for phosphorescent emissive molecules is a full color display. Industry standards for such a display call for pixels adapted to emit particular colors, referred to as "saturated" colors. In particular, these standards call for saturated red, green, and blue pixels. Color may be measured using CIE coordinates, which are well known to the art.

One example of a green emissive molecule is tris(2-phenylpyridine) iridium, denoted Ir(ppy)$_3$, which has the structure:

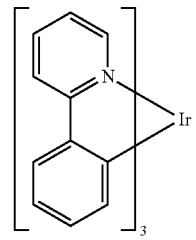

In this, and later figures herein, we depict the dative bond from nitrogen to metal (here, Ir) as a straight line.

As used herein, the term "organic" includes polymeric materials as well as small molecule organic materials that may be used to fabricate organic opto-electronic devices. "Small molecule" refers to any organic material that is not a polymer, and "small molecules" may actually be quite large. Small molecules may include repeat units in some circumstances. For example, using a long chain alkyl group as a substituent does not remove a molecule from the "small molecule" class. Small molecules may also be incorporated into polymers, for example as a pendent group on a polymer backbone or as a part of the backbone. Small molecules may also serve as the core moiety of a dendrimer, which consists of a series of chemical shells built on the core moiety. The core moiety of a dendrimer may be a fluorescent or phosphorescent small molecule emitter. A dendrimer may be a "small molecule," and it is believed that all dendrimers currently used in the field of OLEDs are small molecules.

As used herein, "top" means furthest away from the substrate, while "bottom" means closest to the substrate. Where a first layer is described as "disposed over" a second layer, the first layer is disposed further away from substrate. There may be other layers between the first and second layer, unless it is specified that the first layer is "in contact with" the second layer. For example, a cathode may be described as "disposed over" an anode, even though there are various organic layers in between.

As used herein, "solution processible" means capable of being dissolved, dispersed, or transported in and/or deposited from a liquid medium, either in solution or suspension form.

A ligand is referred to as "photoactive" when it is believed that the ligand contributes to the photoactive properties of an emissive material.

More details on OLEDs, and the definitions described above, can be found in U.S. Pat. No. 7,279,704, which is incorporated herein by reference in its entirety.

SUMMARY OF THE INVENTION

Triphenylene containing benzo-fused thiophene compounds are provided. The compounds may be useful in organic light emitting devices. The compounds may be particularly useful as the host of an emissive layer of an organic light emitting device, as a material for an enhancement layer, or both.

Examples of triphenylene-containing benzo-fused thiophenes include compounds having the structure of Formula (I), Formula (II), and Formula (III):

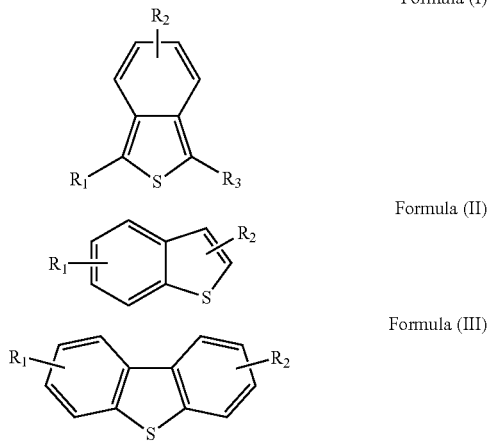

$R_1$, $R_2$ and $R_3$ are independently selected from alkyl, alkoxy, amino, alkenyl, alkynyl, arylkyl, aryl, heteroaryl and hydrogen. Each of $R_1$, $R_2$ and $R_3$ may represent multiple substituents. At least one of $R_1$, $R_2$ and $R_3$ includes a triphenylene group. The triphenylene group may be linked directly to the structure of Formula (I), (II) or (III), but there may also be a "spacer" in between the triphenylene group and the structure of Formula (I), (II) or (III).

Examples of triphenylene containing benzo-fused thiophenes or benzo-fused furans include compounds having the structure:

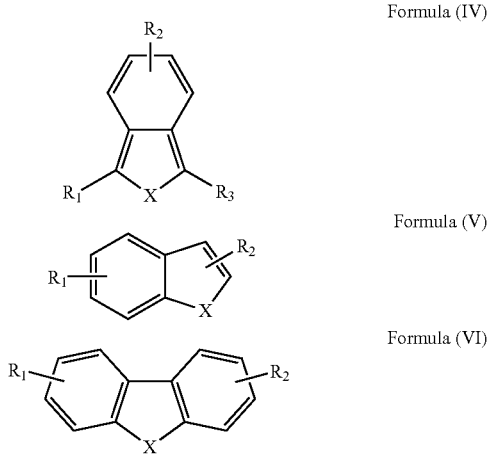

X is S or O. Preferably, $R_1$, $R_2$, and $R_3$ are unfused substituents that are independently selected from $C_nH_{2n+1}$, $OC_nH_{2n+1}$, $OAr_1$, $N(C_nH_{2n+1})_2$, $N(Ar_1)(Ar_2)$, $CH=CH-C_nH_{2n+1}$, $C≡CC_nH_{2n+1}$, $Ar_1$, $Ar_1-Ar_2$, $C_nH_{2n}-Ar_1$, or no substitution. Each of $R_1$, $R_2$, and $R_3$ may represent mono, di, tri, or tetra substitutions. n is 1, 2, 3, 4, 5, 6, 7, 8, 9, or 10. $Ar_1$ and $Ar_2$ are independently selected from the group consisting of benzene, biphenyl, naphthalene, triphenylene, carbazole, and heteroaromatic analogs thereof. At least one of $R_1$, $R_2$, and $R_3$ includes a triphenylene group.

More specific examples of useful triphenylene containing benzo-fused thiophene compounds and triphenylenes containing benzo-fused furan compounds include Compounds 1G-48G and Compounds 1-48, as disclosed herein. The compounds may be useful as the host of an emissive layer of an organic light emitting device, a enhancement layer material of such a device, or both.

DETAILED DESCRIPTION

Generally, an OLED comprises at least one organic layer disposed between and electrically connected to an anode and a cathode. When a current is applied, the anode injects holes and the cathode injects electrons into the organic layer(s). The injected holes and electrons each migrate toward the oppositely charged electrode. When an electron and hole localize on the same molecule, an "exciton," which is a localized electron-hole pair having an excited energy state, is formed. Light is emitted when the exciton relaxes via a photoemissive mechanism. In some cases, the exciton may be localized on an excimer or an exciplex. Non-radiative mechanisms, such as thermal relaxation, may also occur, but are generally considered undesirable.

The initial OLEDs used emissive molecules that emitted light from their singlet states ("fluorescence") as disclosed, for example, in U.S. Pat. No. 4,769,292, which is incorporated by reference in its entirety. Fluorescent emission generally occurs in a time frame of less than 10 nanoseconds.

More recently, OLEDs having emissive materials that emit light from triplet states ("phosphorescence") have been demonstrated. Baldo et al., "Highly Efficient Phosphorescent Emission from Organic Electroluminescent Devices," Nature, vol. 395, 151-154, 1998; ("Baldo-I") and Baldo et al., "Very high-efficiency green organic light-emitting devices based on electrophosphorescence," Appl. Phys. Lett., vol. 75, No. 3, 4-6 (1999) ("Baldo-II"), which are incorporated by reference in their entireties. Phosphorescence is described in more detail in U.S. Pat. No. 7,279,704 at cols. 5-6, which are incorporated by reference.

Figure 1:
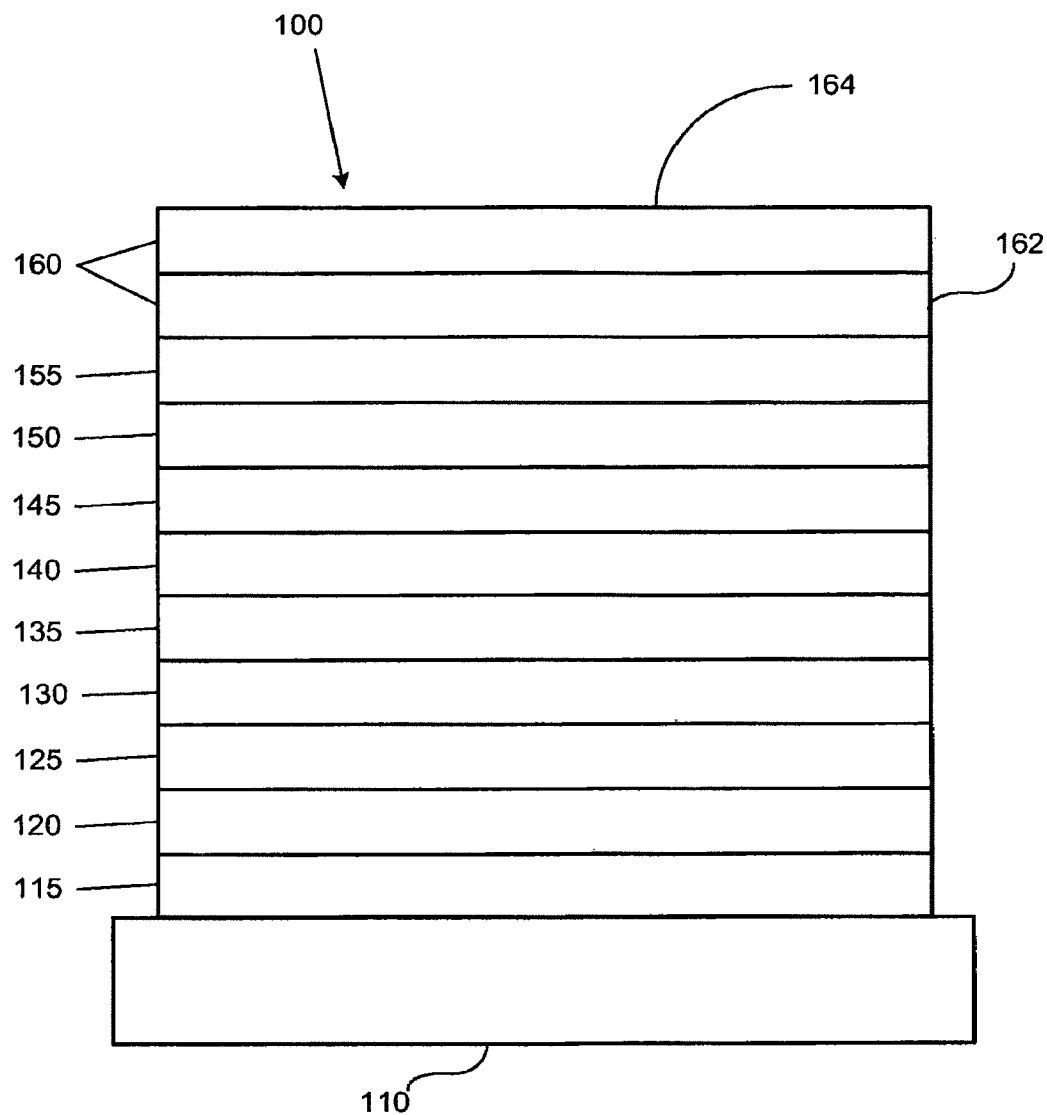
FIG. 1 shows an organic light emitting device.

FIG. 1 shows an organic light emitting device 100. The figures are not necessarily drawn to scale. Device 100 may include a substrate 110, an anode 115, a hole injection layer 120, a hole transport layer 125, an electron blocking layer 130, an emissive layer 135, a hole blocking layer 140, an electron transport layer 145, an electron injection layer 150, a protective layer 155, and a cathode 160. Cathode 160 is a compound cathode having a first conductive layer 162 and a second conductive layer 164. Device 100 may be fabricated by depositing the layers described, in order. The properties and functions of these various layers, as well as example materials, are described in more detail in U.S. Pat. No. 7,279,704 at cols. 6-10, which are incorporated by reference.

More examples for each of these layers are available. For example, a flexible and transparent substrate-anode combination is disclosed in U.S. Pat. No. 5,844,363, which is incorporated by reference in its entirety. An example of a p-doped hole transport layer is m-MTDATA doped with F.sub.4-TCNQ at a molar ratio of 50:1, as disclosed in U.S. Patent Application Publication No. 2003/0230980, which is incorporated by reference in its entirety. Examples of emissive and host materials are disclosed in U.S. Pat. No. 6,303,238 to Thompson et al., which is incorporated by reference in its entirety. An example of an n-doped electron transport layer is BPhen doped with Li at a molar ratio of 1:1, as disclosed in U.S. Patent Application Publication No. 2003/0230980, which is incorporated by reference in its entirety. U.S. Pat. Nos. 5,703,436 and 5,707,745, which are incorporated by reference in their entireties, disclose examples of cathodes including compound cathodes having a thin layer of metal such as Mg:Ag with an overlying transparent, electrically-conductive, sputter-deposited ITO layer. The theory and use of blocking layers is described in more detail in U.S. Pat. No. 6,097,147 and U.S. Patent Application Publication No. 2003/0230980, which are incorporated by reference in their entireties. Examples of injection layers are provided in U.S. Patent Application Publication No. 2004/0174116, which is incorporated by reference in its entirety. A description of protective layers may be found in U.S. Patent Application Publication No. 2004/0174116, which is incorporated by reference in its entirety. An "enhancement layer" occupies the same position in a device as a blocking layer described above, and may have blocking functionality or other functionality that improves device performance.

Figure 2:
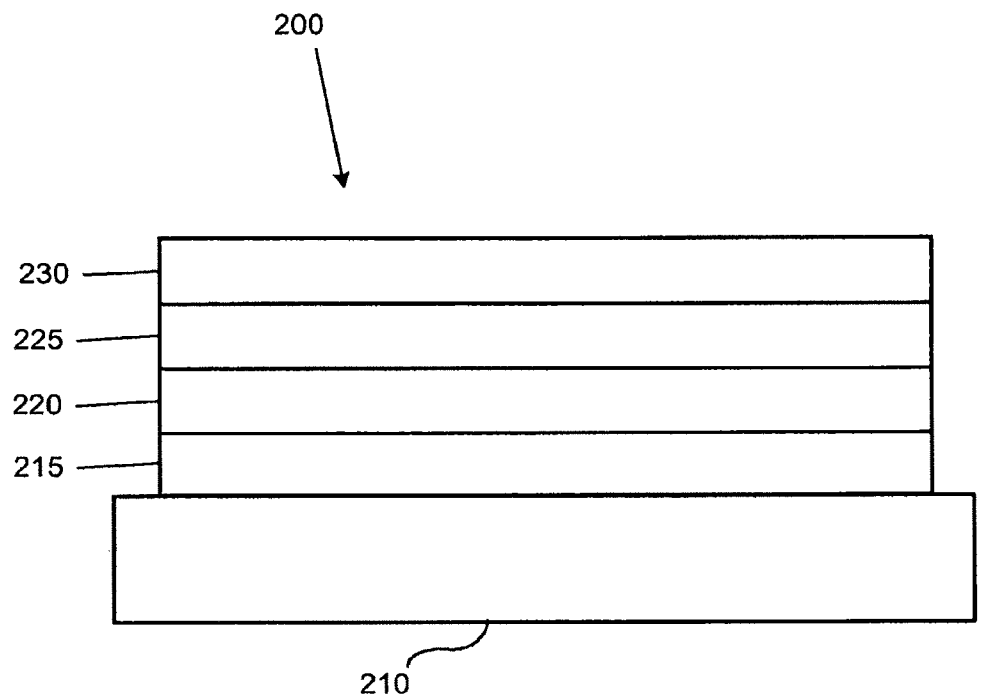
FIG. 2 shows an inverted organic light emitting device that does not have a separate electron transport layer.
Figure 3:
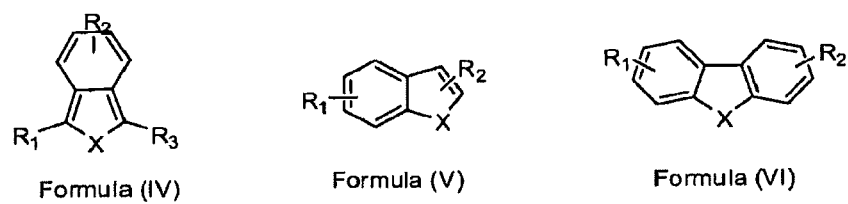
FIG. 3 shows triphenylene-containing benzo-fused thiophene and/or benzo-fused furan compounds.

FIG. 2 shows an inverted OLED 200. The device includes a substrate 210, a cathode 215, an emissive layer 220, a hole transport layer 225, and an anode 230. Device 200 may be fabricated by depositing the layers described, in order. Because the most common OLED configuration has a cathode disposed over the anode, and device 200 has cathode 215 disposed under anode 230, device 200 may be referred to as an "inverted" OLED. Materials similar to those described with respect to device 100 may be used in the corresponding layers of device 200. FIG. 2 provides one example of how some layers may be omitted from the structure of device 100.

The simple layered structure illustrated in FIGS. 1 and 2 is provided by way of non-limiting example, and it is understood that embodiments of the invention may be used in connection with a wide variety of other structures. The specific materials and structures described are exemplary in nature, and other materials and structures may be used. Functional OLEDs may be achieved by combining the various layers described in different ways, or layers may be omitted entirely, based on design, performance, and cost factors. Other layers not specifically described may also be included. Materials other than those specifically described may be used. Although many of the examples provided herein describe various layers as comprising a single material, it is understood that combinations of materials, such as a mixture of host and dopant, or more generally a mixture, may be used. Also, the layers may have various sublayers. The names given to the various layers herein are not intended to be strictly limiting. For example, in device 200, hole transport layer 225 transports holes and injects holes into emissive layer 220, and may be described as a hole transport layer or a hole injection layer. In one embodiment, an OLED may be described as having an "organic layer" disposed between a cathode and an anode. This organic layer may comprise a single layer, or may further comprise multiple layers of different organic materials as described, for example, with respect to FIGS. 1 and 2.

Structures and materials not specifically described may also be used, such as OLEDs comprised of polymeric materials (PLEDs) such as disclosed in U.S. Pat. No. 5,247,190 to Friend et al., which is incorporated by reference in its entirety. By way of further example, OLEDs having a single organic layer may be used. OLEDs may be stacked, for example as described in U.S. Pat. No. 5,707,745 to Forrest et al, which is incorporated by reference in its entirety. The OLED structure may deviate from the simple layered structure illustrated in FIGS. 1 and 2. For example, the substrate may include an angled reflective surface to improve outcoupling, such as a mesa structure as described in U.S. Pat. No. 6,091,195 to Forrest et al., and/or a pit structure as described in U.S. Pat. No. 5,834,893 to Bulovic et al., which are incorporated by reference in their entireties.

Unless otherwise specified, any of the layers of the various embodiments may be deposited by any suitable method. For the organic layers, preferred methods include thermal evaporation, ink-jet, such as described in U.S. Pat. Nos. 6,013,982 and 6,087,196, which are incorporated by reference in their entireties, organic vapor phase deposition (OVPD), such as described in U.S. Pat. No. 6,337,102 to Forrest et al., which is incorporated by reference in its entirety, and deposition by organic vapor jet printing (OVJP), such as described in U.S. patent application Ser. No. 10/233,470, which is incorporated by reference in its entirety. Other suitable deposition methods include spin coating and other solution based processes. Solution based processes are preferably carried out in nitrogen or an inert atmosphere. For the other layers, preferred methods include thermal evaporation. Preferred patterning methods include deposition through a mask, cold welding such as described in U.S. Pat. Nos. 6,294,398 and 6,468,819, which are incorporated by reference in their entireties, and patterning associated with some of the deposition methods such as ink-jet and OVJD. Other methods may also be used. The materials to be deposited may be modified to make them compatible with a particular deposition method. For example, substituents such as alkyl and aryl groups, branched or unbranched, and preferably containing at least 3 carbons, may be used in small molecules to enhance their ability to undergo solution processing. Substituents having 20 carbons or more may be used, and 3-20 carbons is a preferred range. Materials with asymmetric structures may have better solution processibility than those having symmetric structures, because asymmetric materials may have a lower tendency to recrystallize. Dendrimer substituents may be used to enhance the ability of small molecules to undergo solution processing.

Devices fabricated in accordance with embodiments of the invention may be incorporated into a wide variety of consumer products, including flat panel displays, computer monitors, televisions, billboards, lights for interior or exterior illumination and/or signaling, heads up displays, fully transparent displays, flexible displays, laser printers, telephones, cell phones, personal digital assistants (PDAs), laptop computers, digital cameras, camcorders, viewfinders, micro-displays, vehicles, a large area wall, theater or stadium screen, or a sign. Various control mechanisms may be used to control devices fabricated in accordance with the present invention, including passive matrix and active matrix. Many of the devices are intended for use in a temperature range comfortable to humans, such as 18 degrees C. to 30 degrees C., and more preferably at room temperature (20-25 degrees C.).

The materials and structures described herein may have applications in devices other than OLEDs. For example, other optoelectronic devices such as organic solar cells and organic photodetectors may employ the materials and structures. More generally, organic devices, such as organic transistors, may employ the materials and structures.

The terms halo, halogen, alkyl, cycloalkyl, alkenyl, alkynyl, arylkyl, heterocyclic group, aryl, and heteroaryl are known to the art, and are defined in U.S. Pat. No. 7,279,704 at cols. 31-32, which are incorporated herein by reference.

Compounds are provided, comprising a triphenylene-containing benzo-fused thiophene. Triphenylene is a polyaromatic hydrocarbon with high triplet energy, yet high π-conjugation and a relatively small energy difference between the first singlet and first triplet levels. This would indicate that triphenylene has relatively easily accessible HOMO and LUMO levels compared to other aromatic compounds with similar triplet energy (e.g., biphenyl). The advantage of using triphenylene and its derivatives as hosts is that it can accommodate red, green and even blue phosphorescent dopants to give high efficiency without energy quenching. Triphenylene hosts may be used to provide high efficiency and stability PHOLEDs. See Kwong and Alleyene, *Triphenylene Hosts in Phosphorescent Light Emitting Diodes*, 2006, 60 pp, US 2006/0280965 A1. Benzo-fused thiophenes may be used as hole transporting organic conductors. In addition, the triplet energies of benzothiophenes, namely dibenzo[b,d]thiophene (referred to herein as "dibenzothiophene"), benzo[b]thiophene and benzo[c]thiophene are relatively high. A combination of benzo-fused thiophenes and triphenylene as hosts in PHOLED may be beneficial. More specifically, benzo-fused thiophenes are typically more hole transporting than electron transporting, and triphenylene is more electron transporting than hole transporting. Therefore combining these two moieties in one molecule may offer improved charge balance which may improve device performance in terms of lifetime, efficiency and low voltage. Different chemical linkage of the two moieties can be used to tune the properties of the resulting compound to make it the most appropriate for a particular phosphorescent emitter, device architecture, and/or fabrication process. For example, m-phenylene linkage is expected to result in higher triplet energy and higher solubility whereas p-phenylene linkage is expected to result in lower triplet energy and lower solubility.

Similar to the characterization of benzo-fused thiophenes, benzo-fused furans are also typically hole transporting materials having relatively high triplet energy. Examples of benzo-fused furans include benzofuran and dibenzofuran. Therefore, a material containing both triphenylene and benzofuran may be advantageously used as host or hole blocking material in PHOLED. A compound containing both of these two groups may offer improved electron stabilization which may improve device stability and efficiency with low voltage. The properties of the triphenylene containing benzofuran compounds may be tuned as necessary by using different chemical linkages to link the triphenylene and the benzofuran.

The compounds may be substituted with groups that are not necessarily triphenylenes, benzo-fused thiophenes, and benzo-fused furans. Preferably, any group that is used as a substituent of the compound has a triplet energy high enough to maintain the benefit of having triphenylene benzo-fused thiophenes or benzo-fused furans (i.e. the triplet energy of the substituent maintains the high triplet energy of benzo-fused thiophenes, benzo-fused furans and triphenylenes). Examples of such groups that may be used as substituents of the compound may include any substituent selected from $C_nH_{2n+1}$, $OC_nH_{2n+1}$, $OAr_1$, $N(C_nH_{2n+1})_2$, $N(Ar_1)(Ar_2)$, $CH=CH-C_nH_{2n+1}$, $C\equiv CC_nH_{2n+1}$, $Ar_1$, $Ar_1-Ar_2$, $C_nH_{2n}-Ar_1$, or no substitution, wherein n is 1, 2, 3, 4, 5, 6, 7, 8, 9, or 10, and wherein $Ar_1$ and $Ar_2$ are independently selected from the group consisting of benzene, biphenyl, naphthalene, triphenylene, carbazole, and heteroaromatic analogs thereof. The compounds described herein have a high enough triplet energy to be suitable for use in a device having phosphorescent blue emissive materials.

The substituents of the compounds described herein are unfused such that the substituents are not fused to the triphenylene, benzo-fused furan or benzo-fused thiophene moieties of the compound. The substituents may optionally be inter-fused (i.e. fused to each other).

In addition to improved device stability and efficiency, the materials provided herein may also offer improved film formation in the device as fabricated by both vapor deposition and solution processing methods. In particular, materials offering improved fabrication have a central pyridine ring to which the benzo-fused thiophenylene and triphenylene, or benzofuran and triphenylene, are attached. The improved film formation is believed to be a result of the combination of polar and non-polar rings in the compound.

Examples of triphenylene-containing benzo-fused thiophenes include compounds having the structure of Formula (I), Formula (II), and Formula (III):

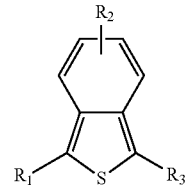

Formula (I)

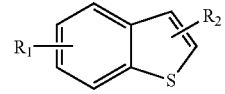

Formula (II)

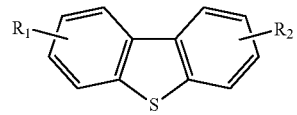

Formula (III)

$R_1$, $R_2$ and $R_3$ are independently selected from alkyl, alkoxy, amino, alkenyl, alkynyl, arylkyl, aryl, heteroaryl and hydrogen. Each of $R_1$, $R_2$ and $R_3$ may represent multiple substituents. At least one of $R_1$, $R_2$ and $R_3$ includes a triphenylene group. The triphenylene group may be linked directly to the structure of Formula (I), (II) or (III), but there may also be a "spacer" in between the triphenylene group and the structure of Formula (I), (II) or (III).

Examples of triphenylene containing benzo-fused thiophenes or benzo-fused furans include compounds having the structure:

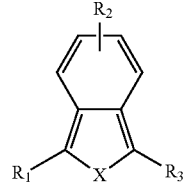

Formula (IV)

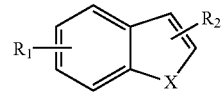

Formula (V)

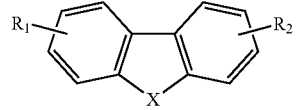

Formula (VI)

X is S or O. Preferably, $R_1$, $R_2$, and $R_3$ are unfused substituents that are independently selected from $C_nH_{2n+1}$, $OC_nH_{2n+1}$, $OAr_1$, $N(C_nH_{2n+1})_2$, $N(Ar_1)(Ar_2)$, $CH=CH-C_nH_{2n+1}$, $C\equiv CC_nH_{2n+1}$, $Ar_1$, $Ar_1-Ar_2$, $C_nH_{2n}-Ar_1$, or no substitution. Each of $R_1$, $R_2$, and $R_3$ may represent mono, di, tri, or tetra substitutions. n is 1, 2, 3, 4, 5, 6, 7, 8, 9, or 10. $Ar_1$ and $Ar_2$ are independently selected from the group consisting of benzene, biphenyl, naphthalene, triphenylene, carbazole, and heteroaromatic analogs thereof. At least one of $R_1$, $R_2$, and $R_3$ includes a triphenylene group.

Examples of compounds having the structure of Formula (I) include:

Compound 11'G

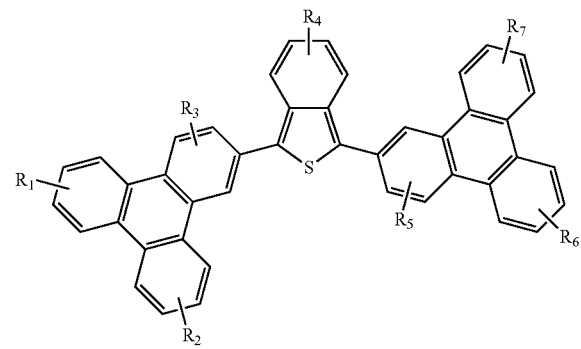

Compound 11'

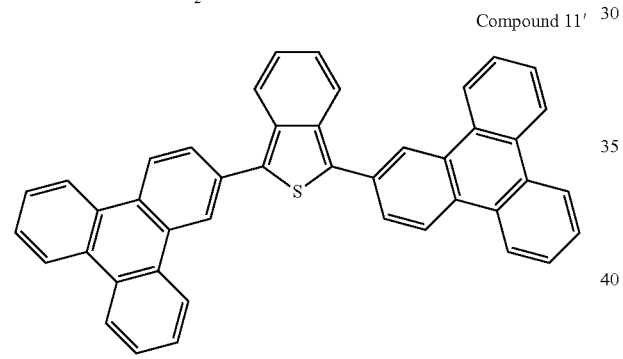

$R_1$ to $R_n$ represents, independently, mono, di, tri or tetra substitutions selected from alkyl, alkoxy, amino, alkenyl, alkynyl, arylkyl, aryl and heteroaryl, or no substitution.

Examples of compounds having the structure of Formula (IV) include:

Compound 11G

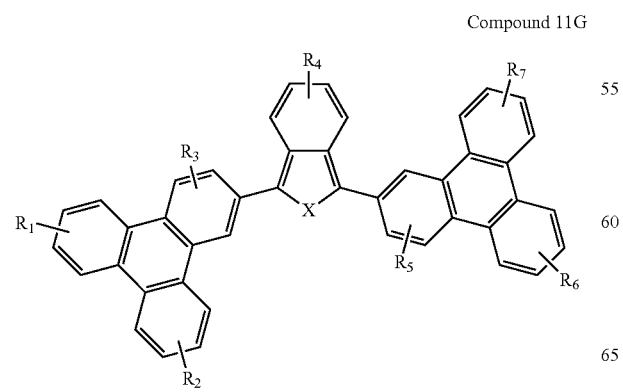

Compound 11

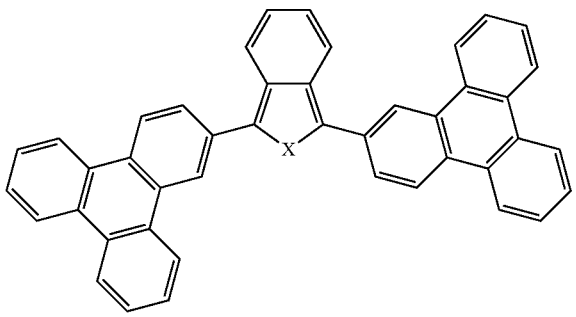

X is S or O. Preferably, X is S. $R_1$ to $R_n$ are independently selected from the group consisting of $C_nH_{2n+1}$, $OC_nH_{2n+1}$, $OAr_1$, $N(C_nH_{2n+1})_2$, $N(Ar_1)(Ar_2)$, $CH=CH-C_nH_{2n+1}$, $C\equiv CC_nH_{2n+1}$, $Ar_1$, $Ar_1-Ar_2$, $C_nH_{2n}-Ar_1$, or no substitution. Each of $R_1$ to $R_n$ may represent mono, di, tri or tetra substitutions. n is 1, 2, 3, 4, 5, 6, 7, 8, 9, or 10. $Ar_1$ and $Ar_2$ are independently selected from the group consisting of benzene, biphenyl, naphthalene, triphenylene, carbazole, and heteroaromatic analogs thereof. At least one of $R_1$, $R_2$, and $R_3$ includes a triphenylene group.

Examples of compounds having the structure of Formula (II) include:

Compound 12'G

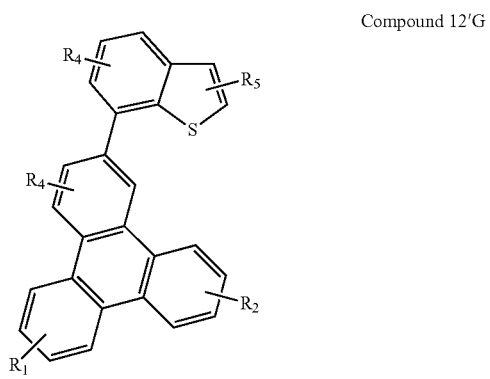

Compound 12'

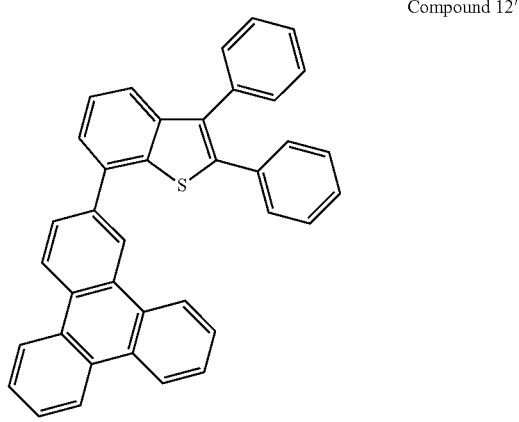

Compound 13′G
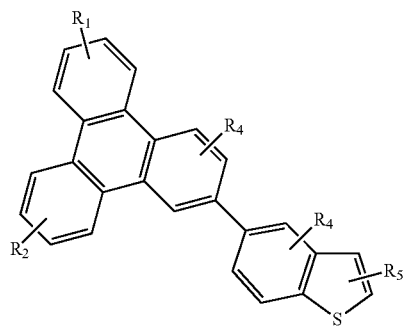
Compound 13′
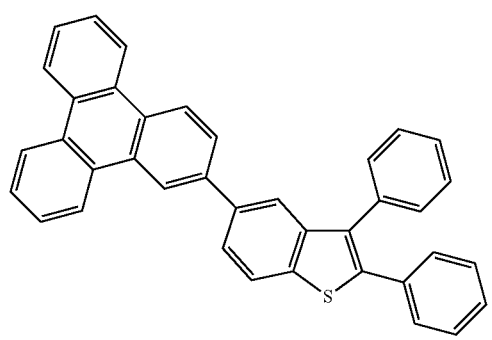
Compound 14′G
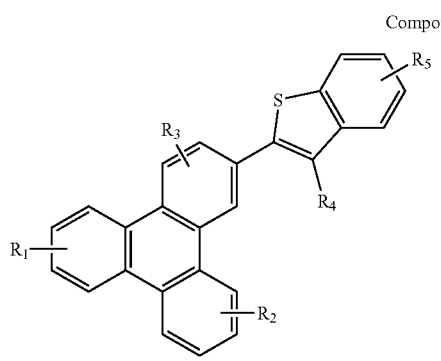
Compound 14′
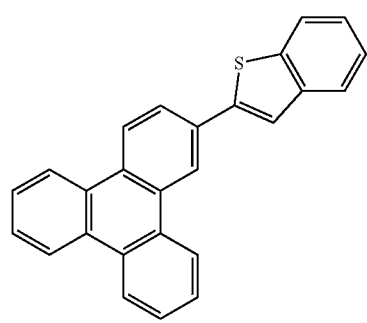
Compound 16′G
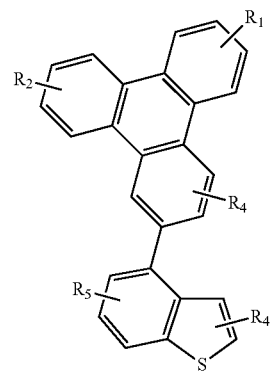
Compound 16′
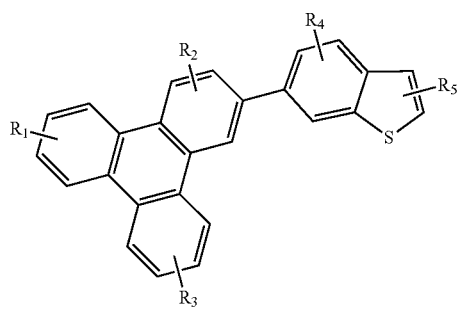
Compound 17′G
Compound 17′
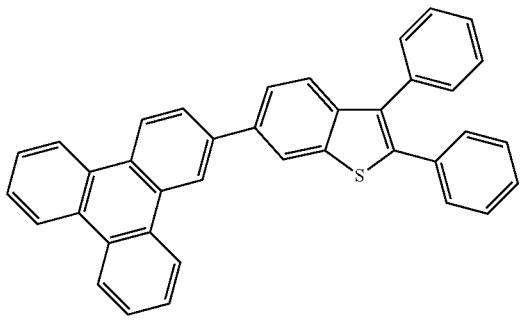

Compound 18′G
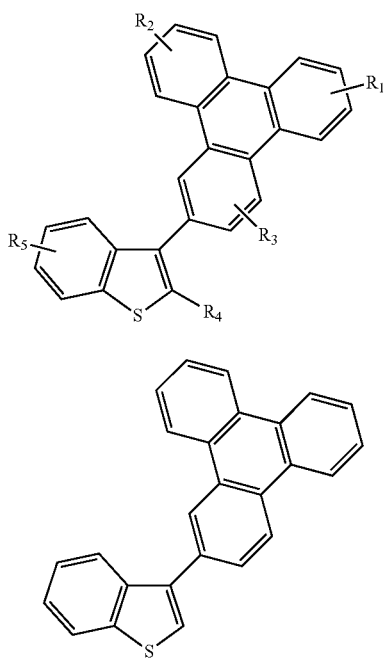
Compound 18′
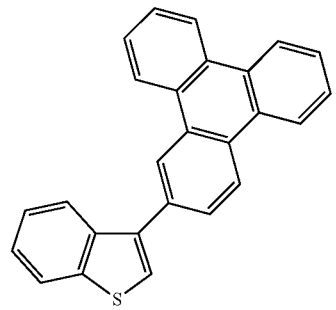
R₁ to Rₙ represents, independently, mono, di, tri or tetra substitutions selected from alkyl, alkoxy, amino, alkenyl, alkynyl, arylkyl, aryl and heteroaryl, or no substitution.
Examples of compounds having the structure of Formula (V) include:
Compound 12G
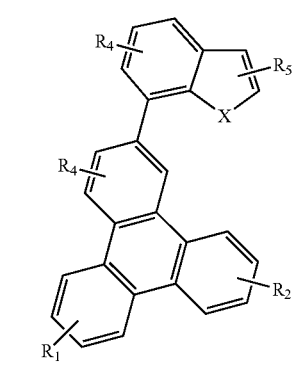
Compound 12
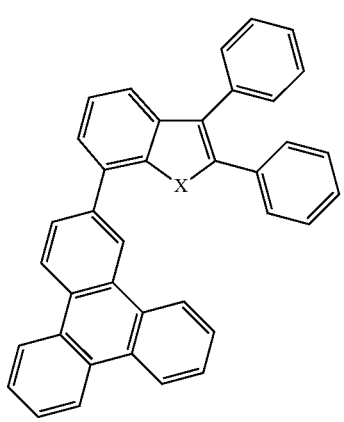
Compound 13G
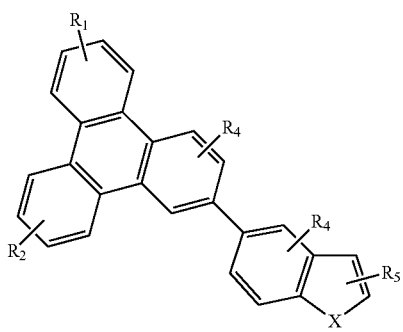
Compound 13
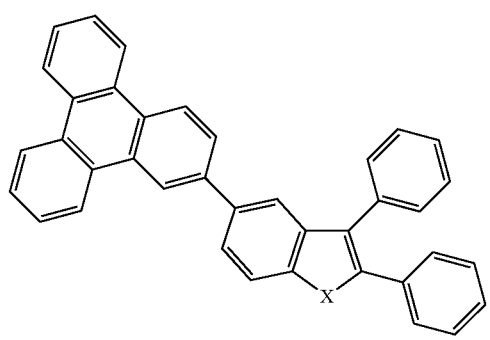
Compound 14G
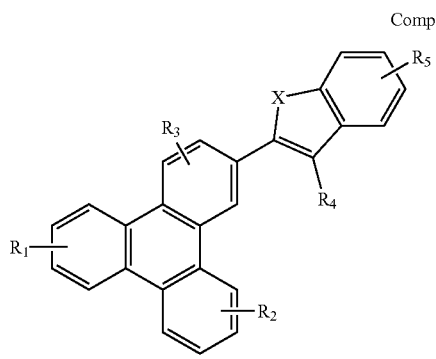
Compound 14
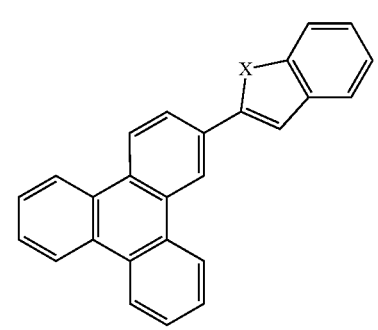

Compound 16G

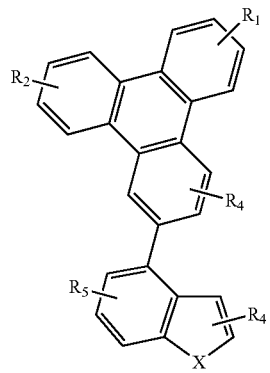

Compound 16

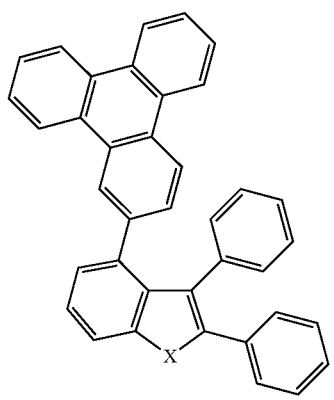

Compound 17G

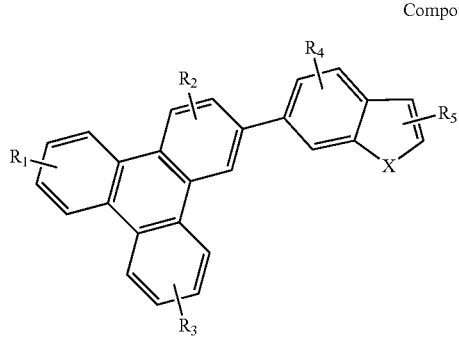

Compound 17

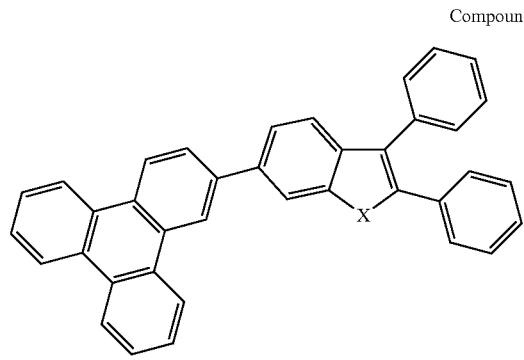

Compound 18G

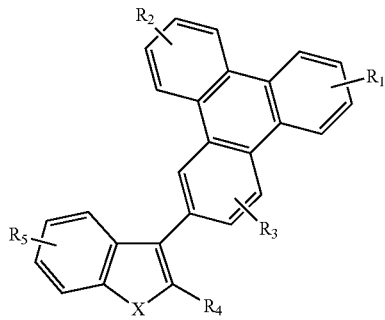

Compound 18

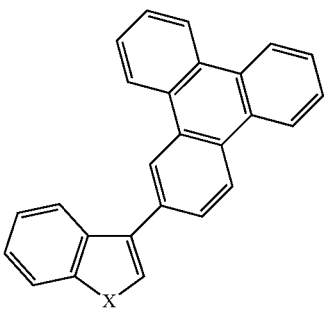

X is S or O. Preferably, X is S. $R_1$ to $R_n$ are independently selected from the group consisting of $C_nH_{2n+1}$, $OC_nH_{2n+1}$, $OAr_1$, $N(C_nH_{2n+1})_2$, $N(Ar_1)(Ar_2)$, $CH=CH-C_nH_{2n+1}$, $C\equiv CC_nH_{2n+1}$, $Ar_1$, $Ar_1-Ar_2$, $C_nH_{2n}-Ar_1$, or no substitution. Each of $R_1$ to $R_n$ may represent mono, di, tri, or tetra substitutions. n is 1, 2, 3, 4, 5, 6, 7, 8, 9, or 10. $Ar_1$ and $Ar_2$ are independently selected from the group consisting of benzene, biphenyl, naphthalene, triphenylene, carbazole, and heteroaromatic analogs thereof. At least one of $R_1$, $R_2$, and $R_3$ includes a triphenylene group.

Examples of compounds having the structure of Formula (III) include:

Compound 1'G

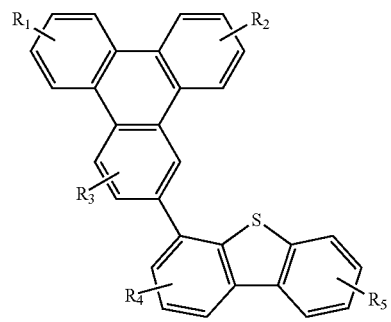

Compound 1'
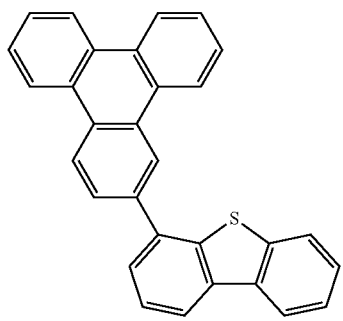
Compound 2'G
Compound 2'
Compound 3'G
Compound 3'
Compound 4'G
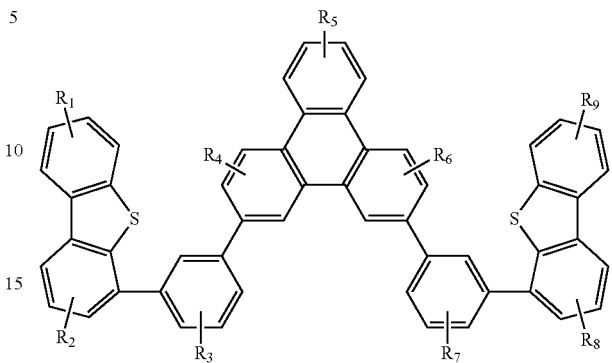
Compound 4'
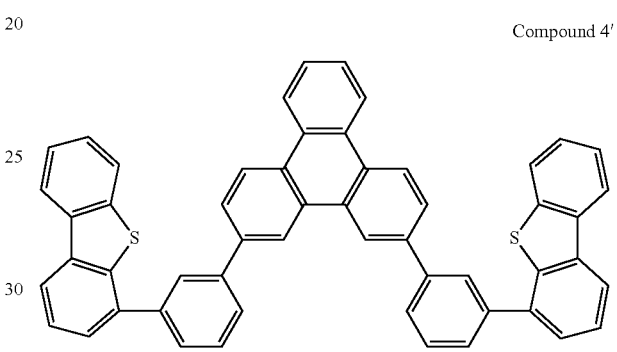
Compound 5'G
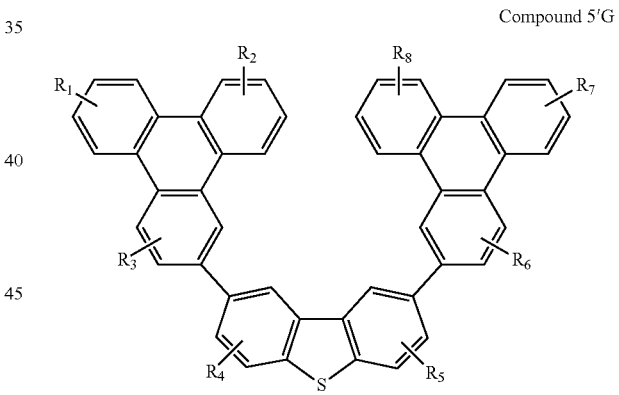
Compound 5'
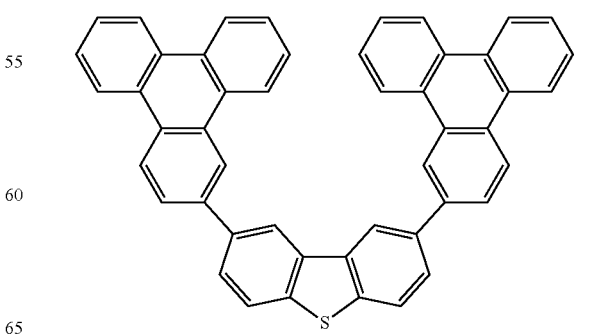

Compound 6'G
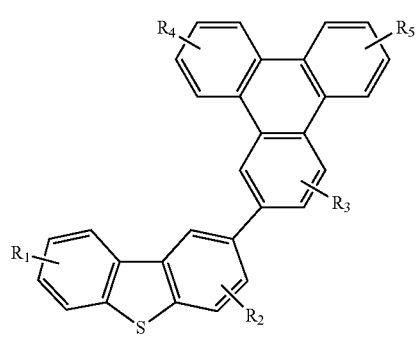
Compound 6'
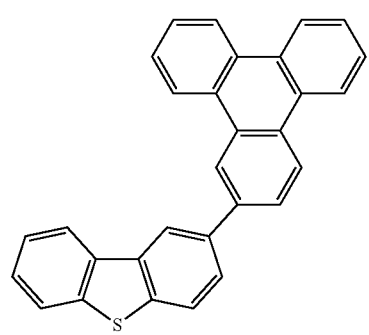
Compound 7'G
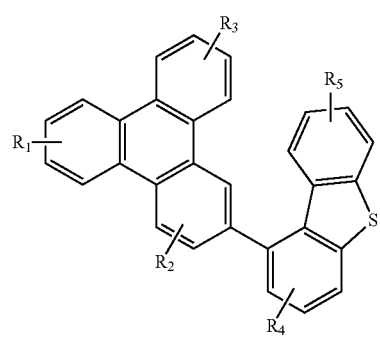
Compound 7'
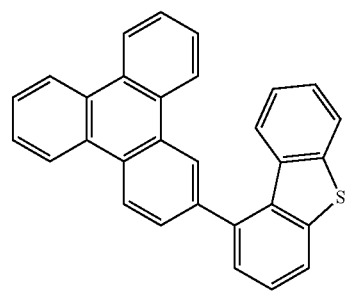
Compound 8'G
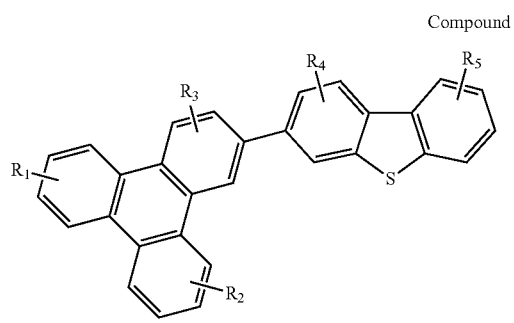
Compound 8'
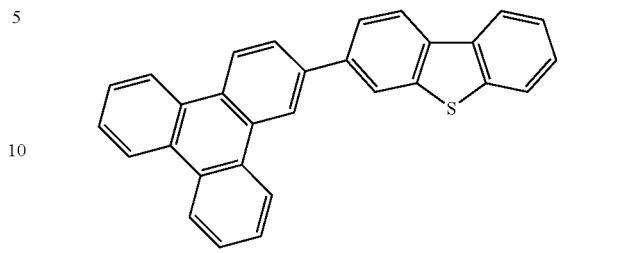
Compound 9'G
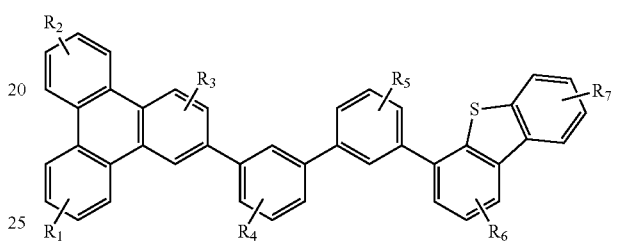
Compound 9'
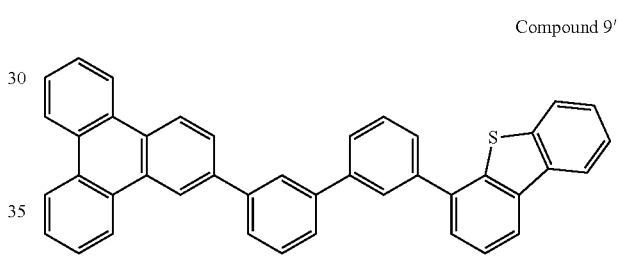
Compound 10'G
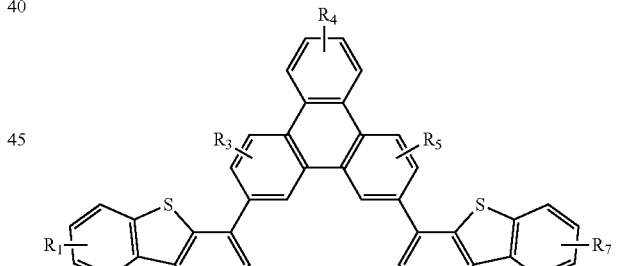
Compound 10'
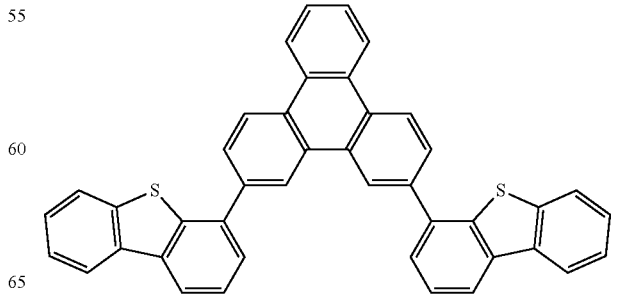

Compound 15'G
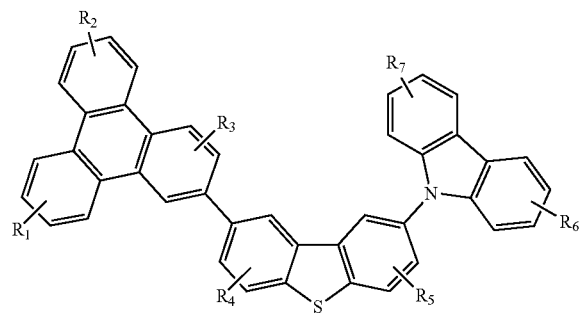
Compound 15'
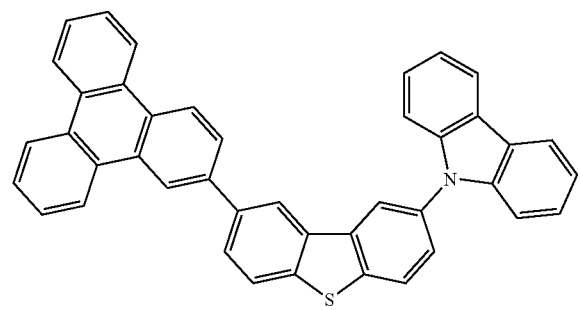
R₁ to Rₙ represents, independently, mono, di, tri or tetra substitutions selected from alkyl, alkoxy, amino, alkenyl, alkynyl, arylkyl, aryl and heteroaryl, or no substitution.
Examples of compounds having the structure of Formula (VI) include:
Compound 1G
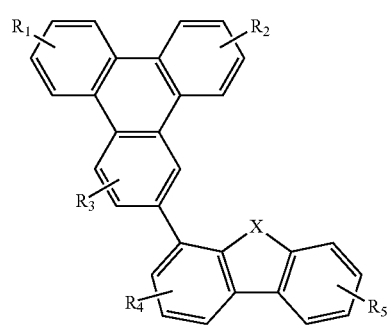
Compound 1
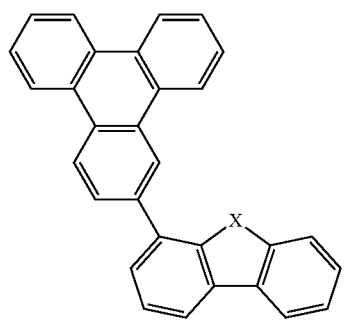
Compound 2G
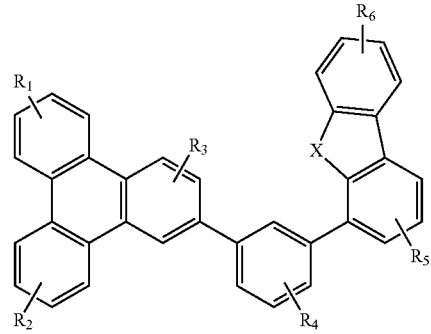
Compound 2
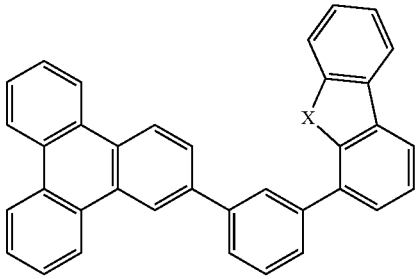
Compound 3G
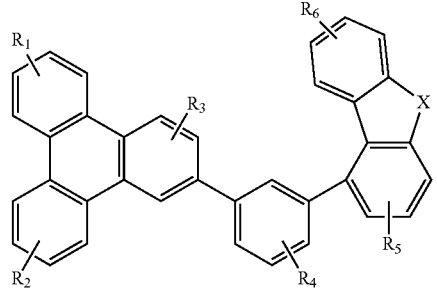
Compound 3
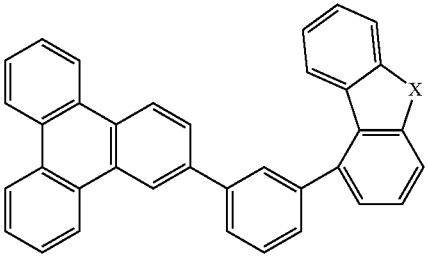
Compound 4G
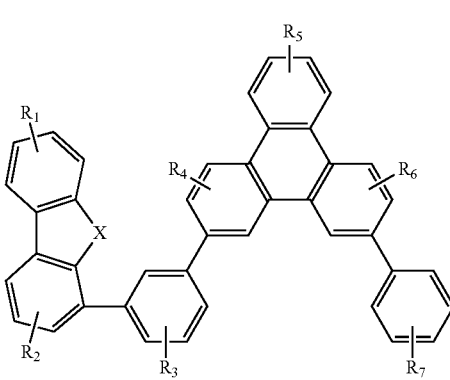

Compound 4
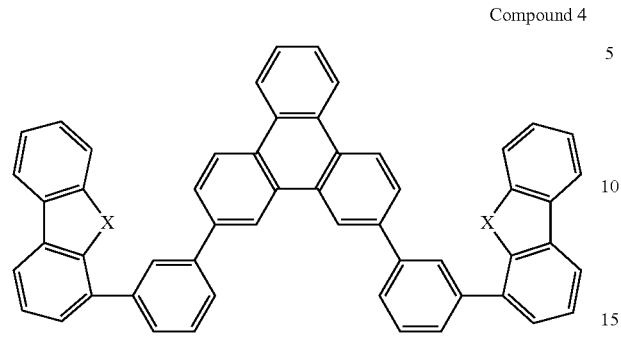
Compound 5G
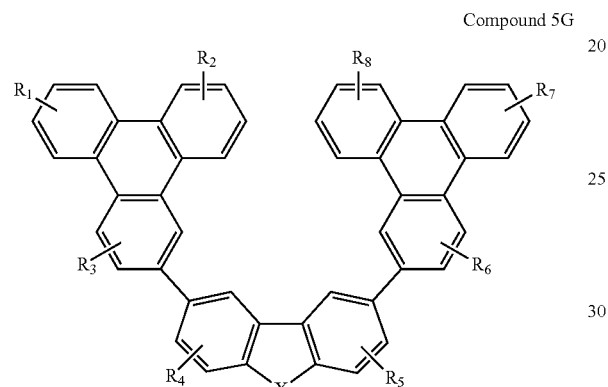
Compound 5
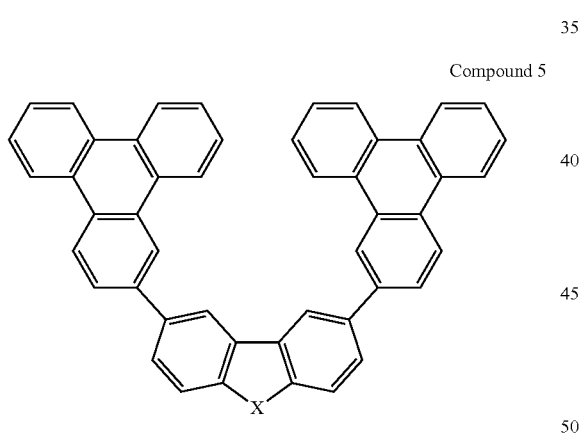
Compound 6G
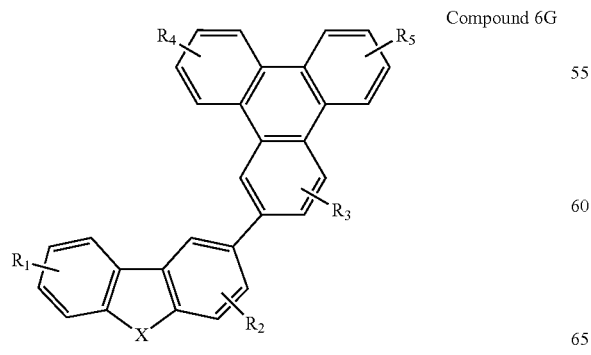
Compound 6
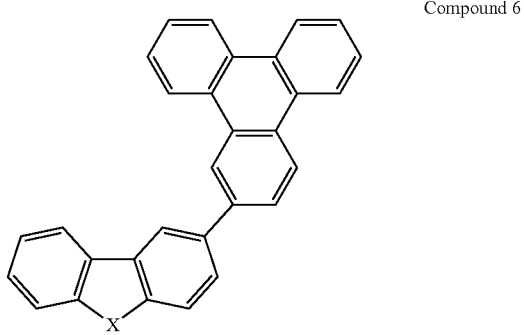
Compound 7G
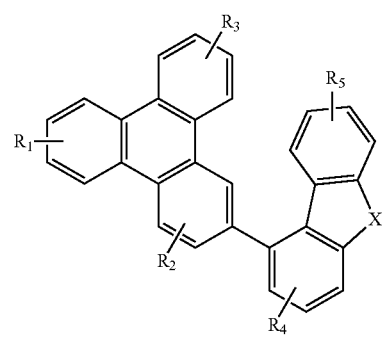
Compound 7
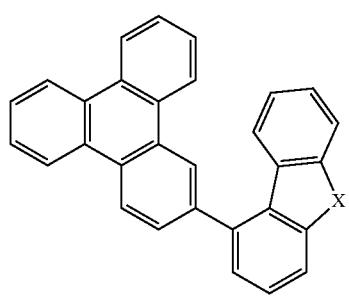
Compound 8G
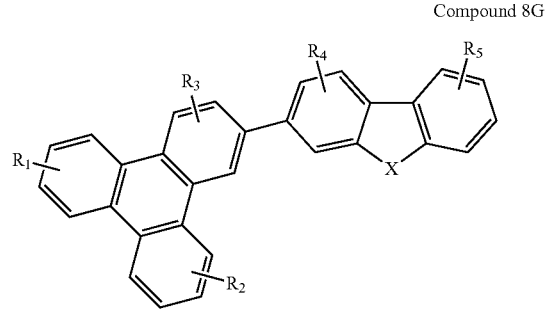
Compound 8
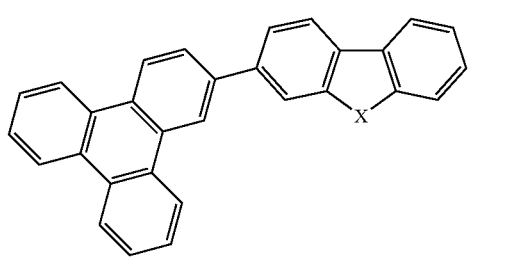

Compound 9G
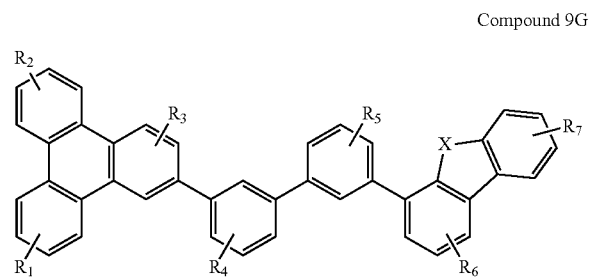
Compound 9
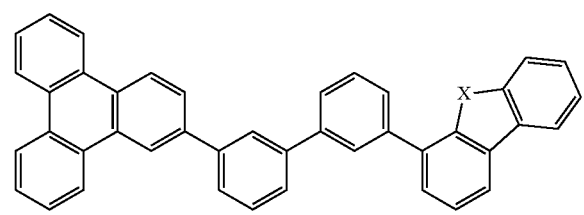
Compound 10G
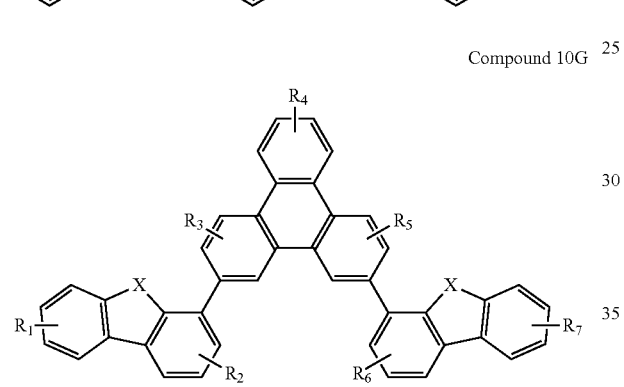
Compound 10
Compound 15G
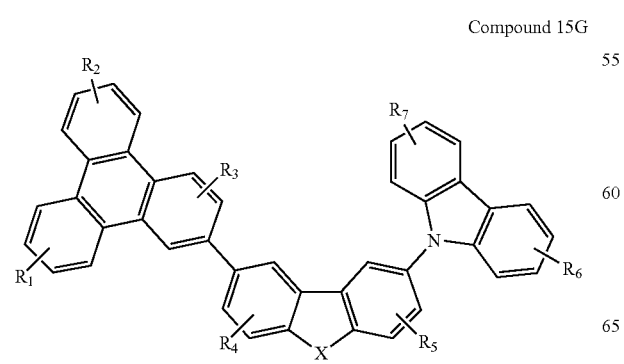
Compound 15
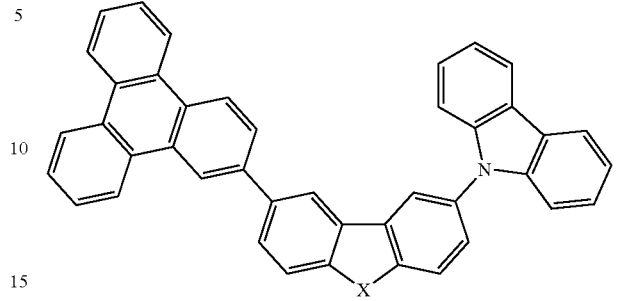
Compound 19 G
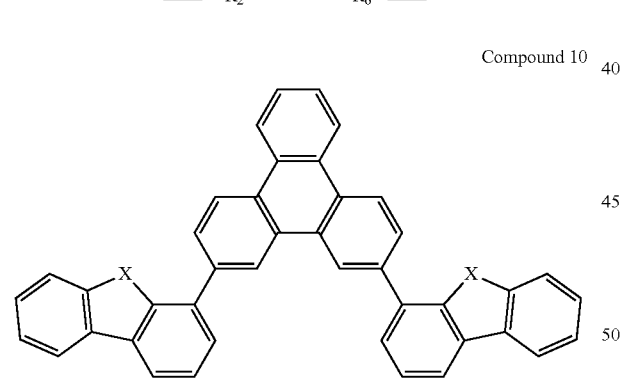
Compound 19
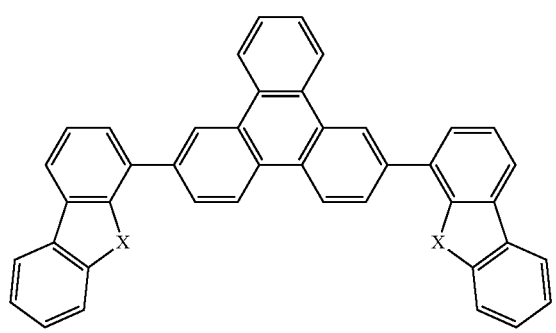
Compound 20 G
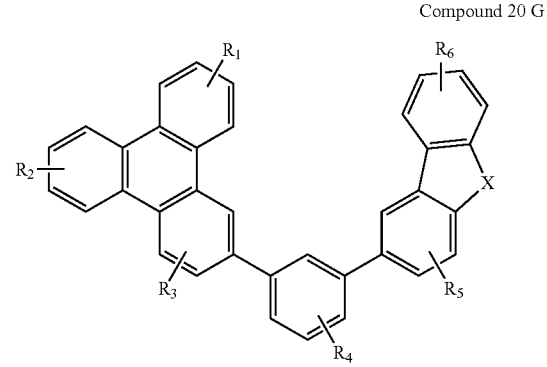

Compound 20
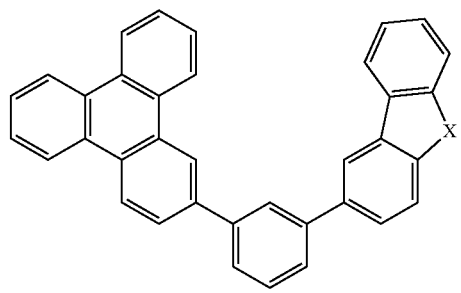
Compound 21 G
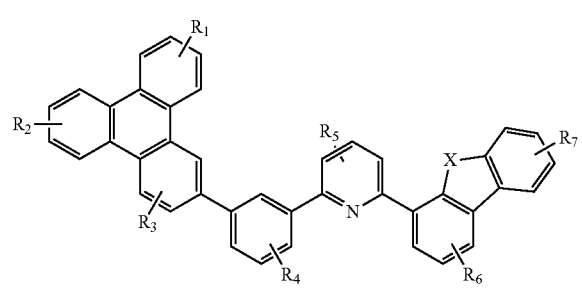
Compound 21
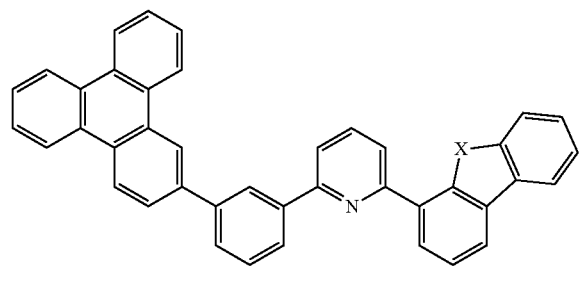
Compound 22 G
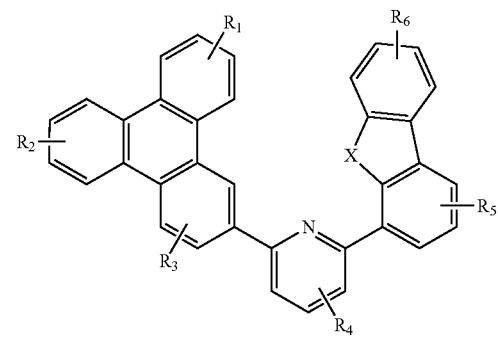
Compound 22
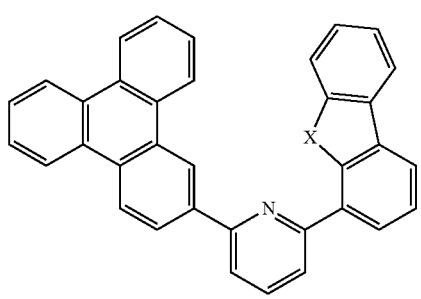
Compound 23 G
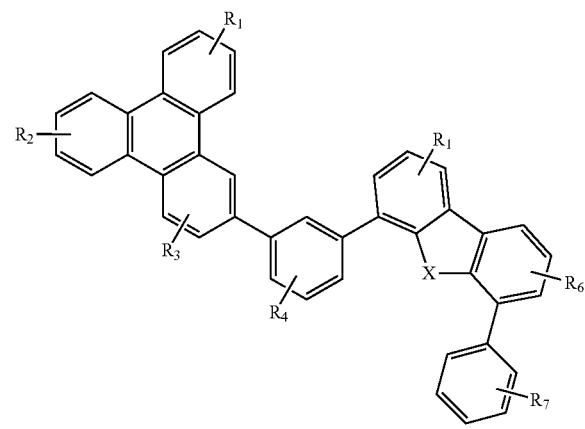
Compound 23
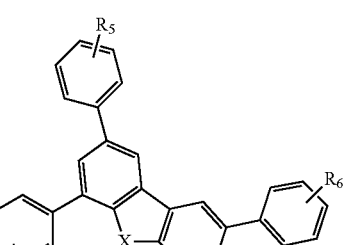
Compound 24 G
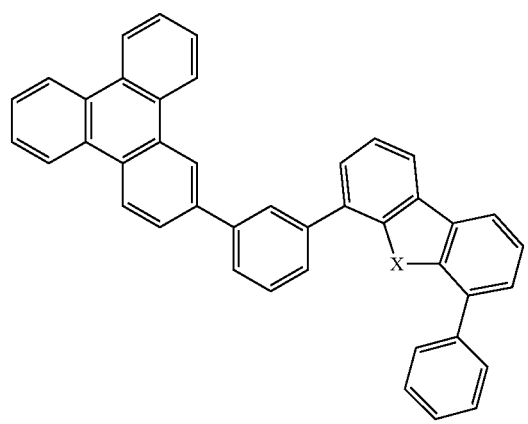
Compound 24

Compound 25 G
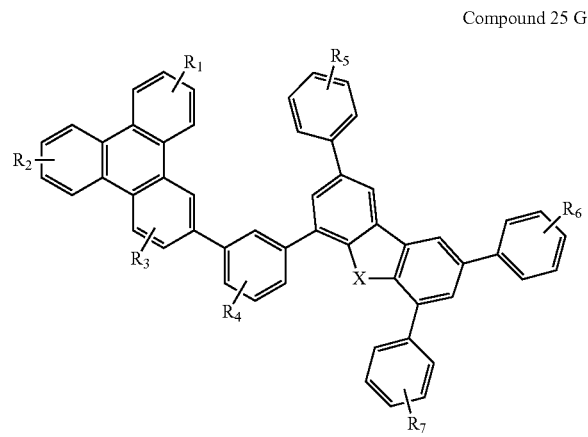
Compound 25
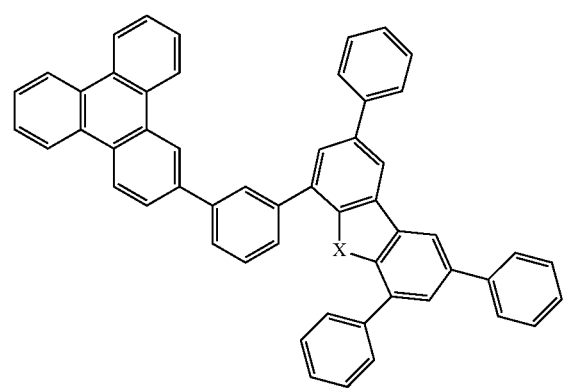
Compound 26G
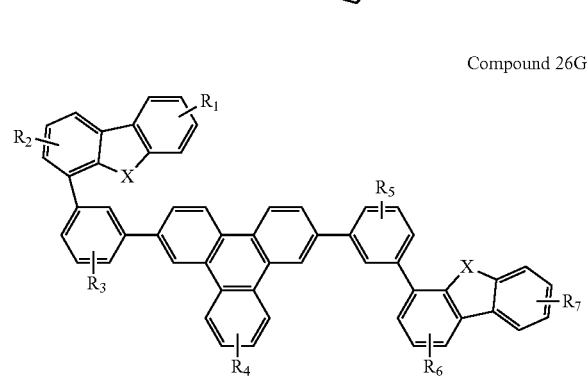
Compound 26
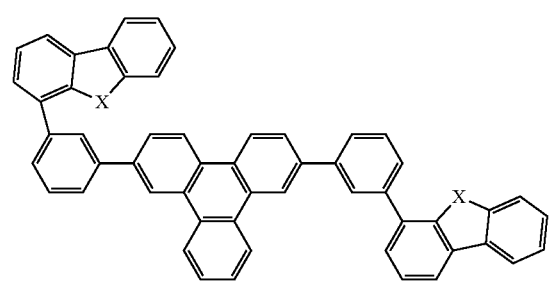
Compound 27 G
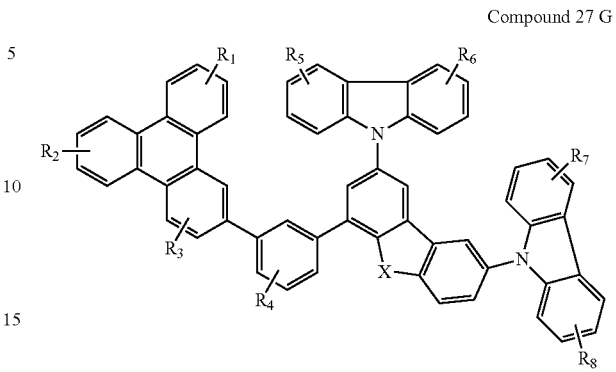
Compound 27
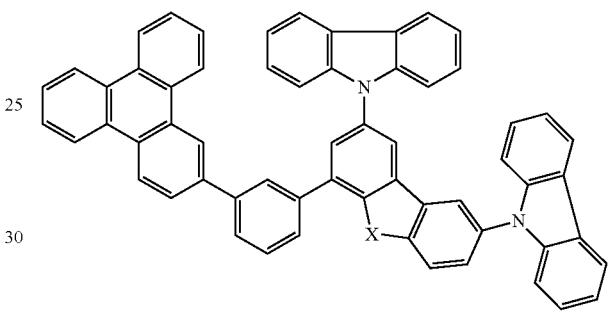
Compound 28 G
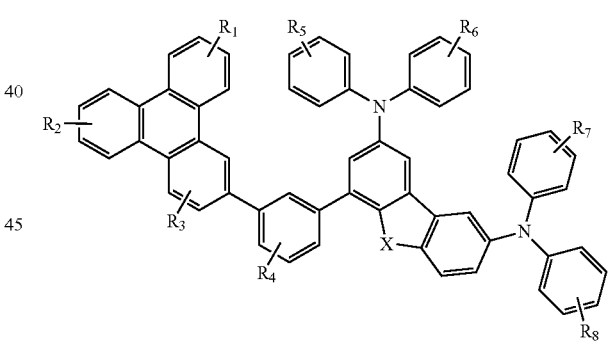
Compound 28
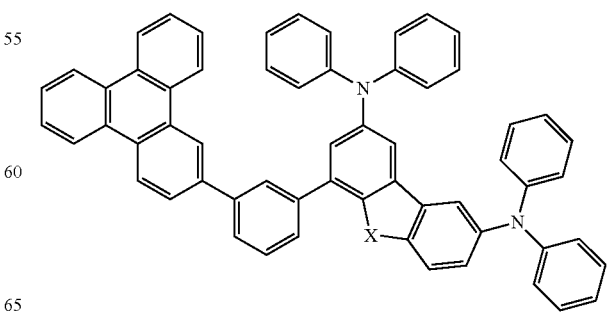

Compound 29G
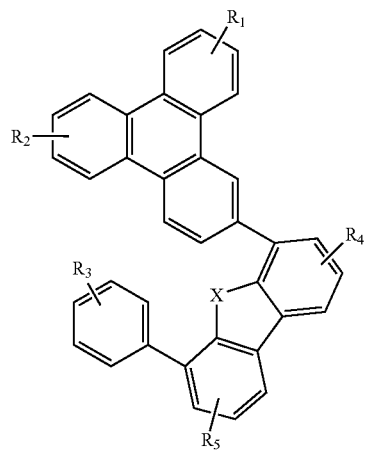
Compound 29
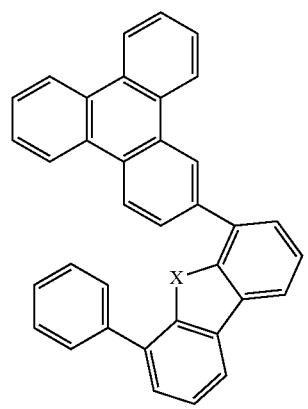
Compound 30 G
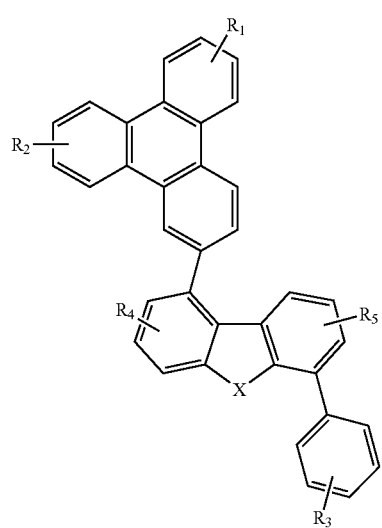
Compound 30
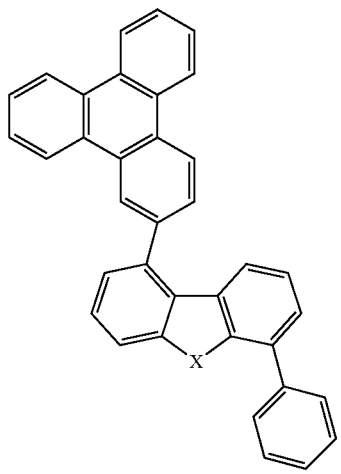
Compound 31 G
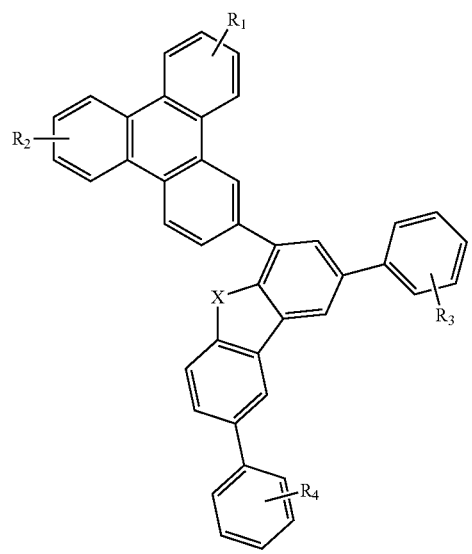
Compound 31
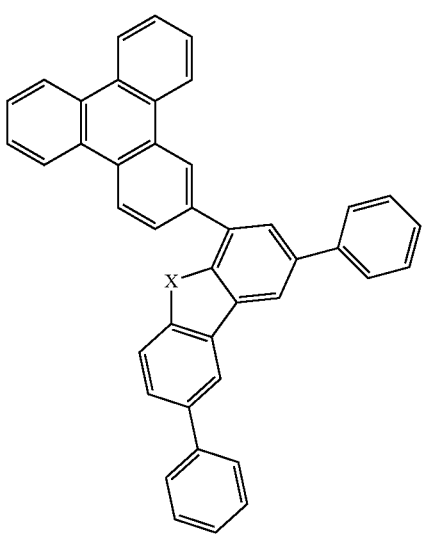

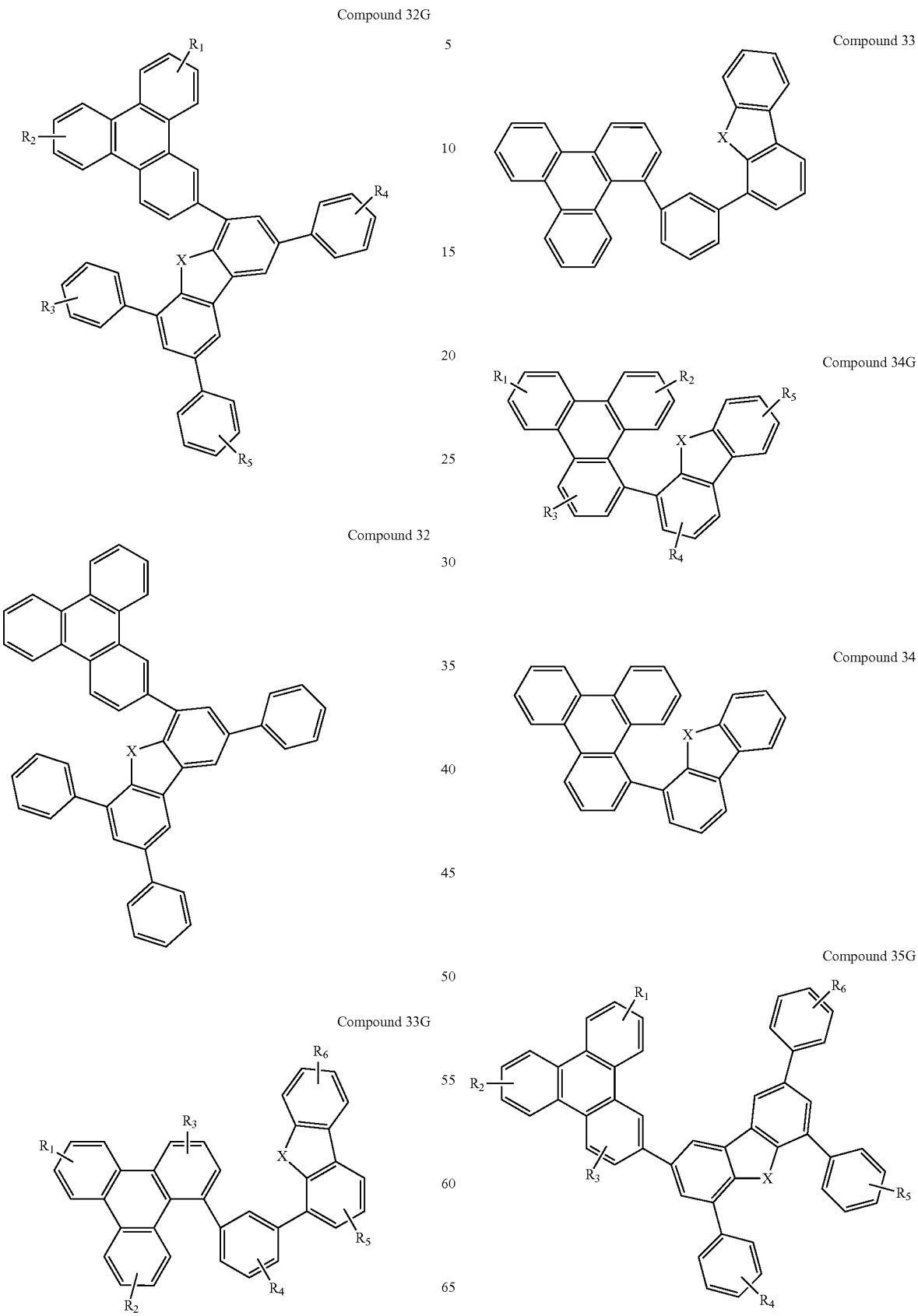

Compound 35
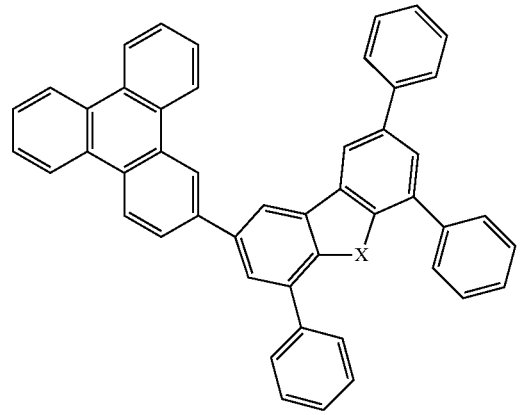
Compound 36G
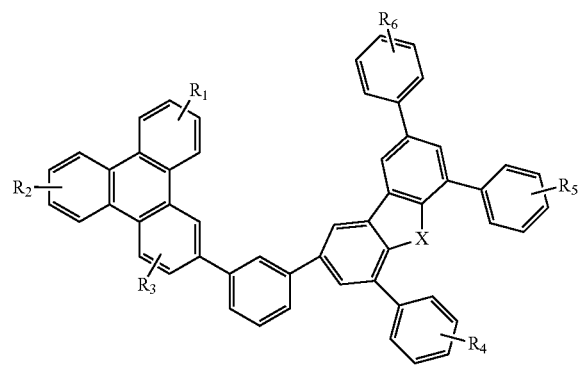
Compound 36
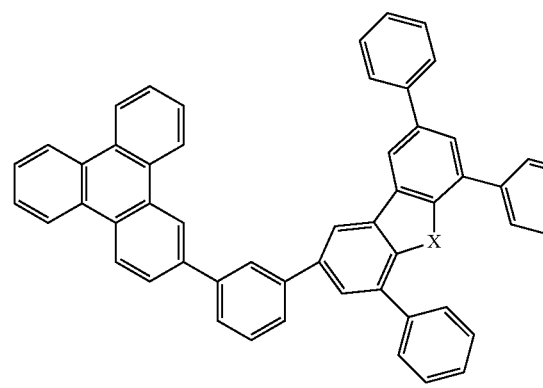
Compound 37G
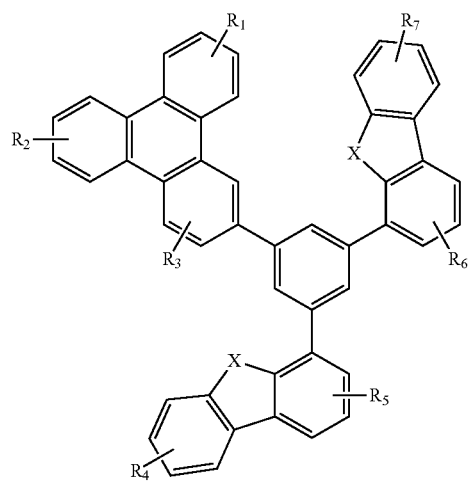
Compound 37
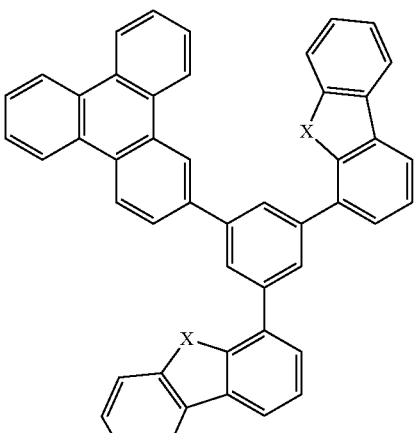
Compound 38G
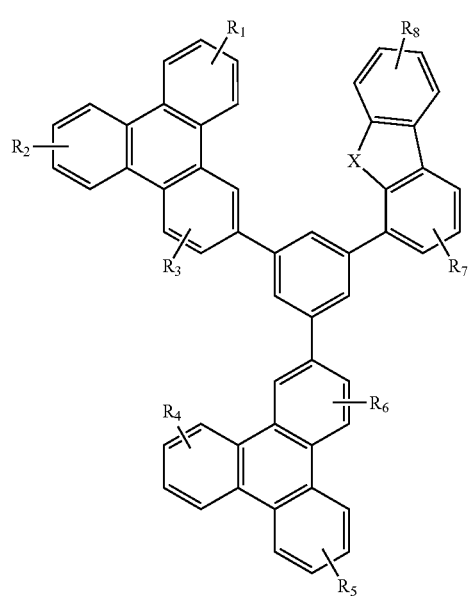

Compound 38
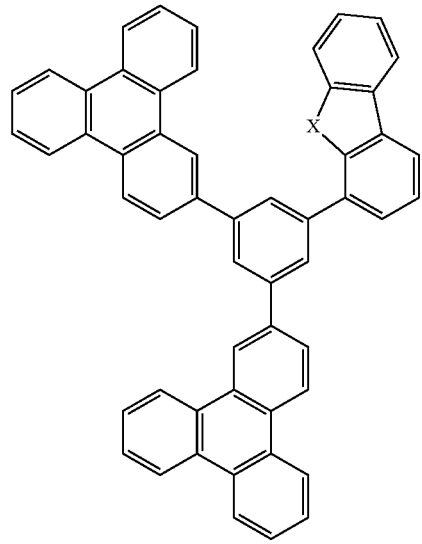
Compound 39G
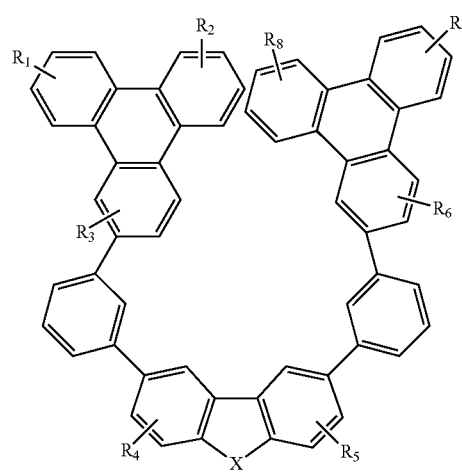
Compound 39
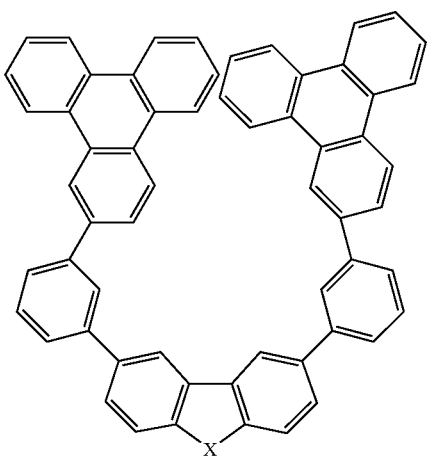
Compound 40G
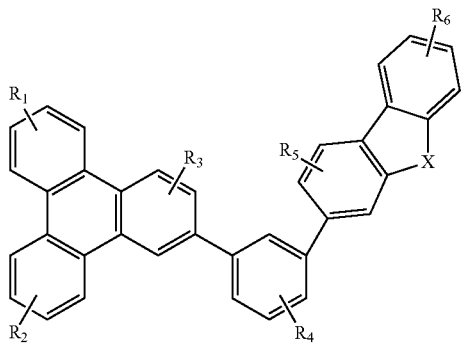
Compound 40
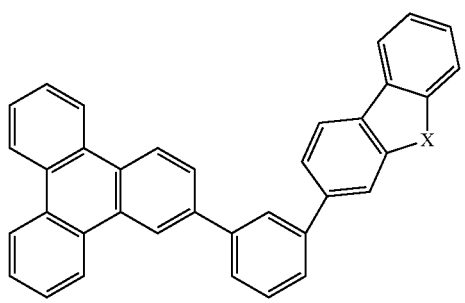
Compound 41G
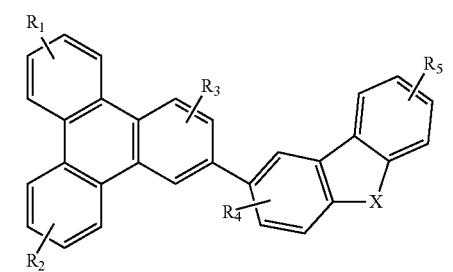
Compound 41
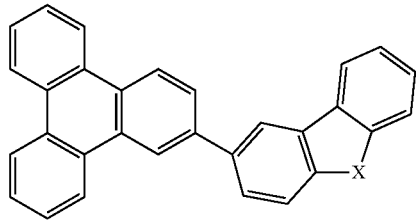
Compound 42G
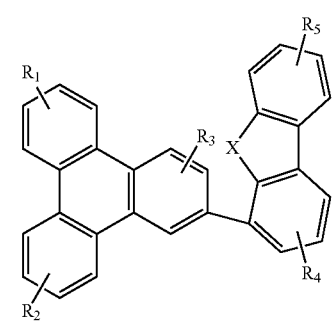

Compound 42
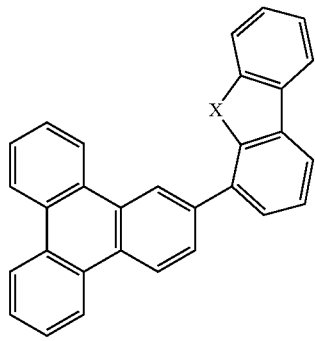
Compound 43 G
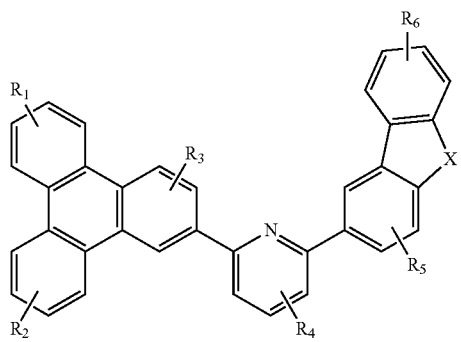
Compound 43
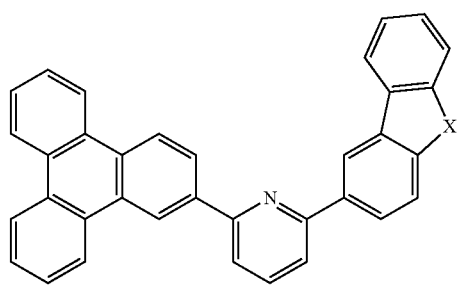
Compound 44 G
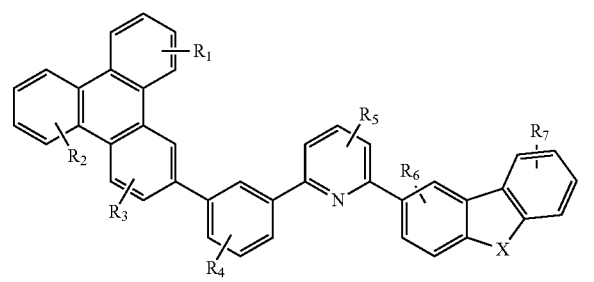
Compound 44
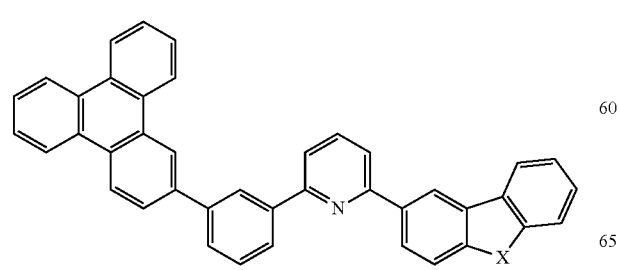
Compound 45G
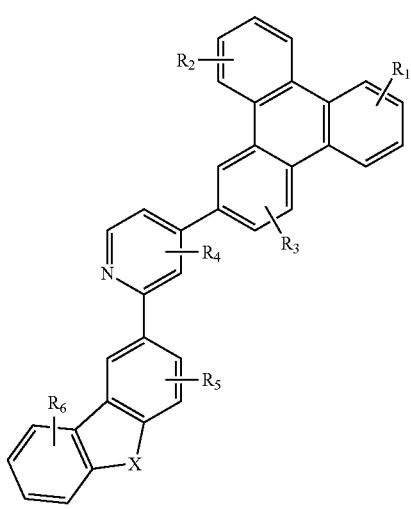
Compound 45
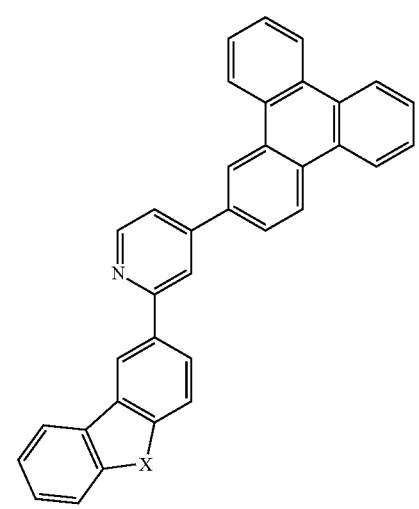
Compound 46 G
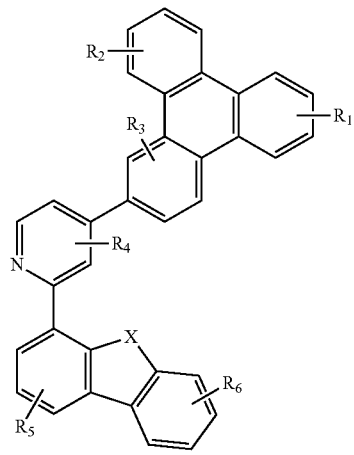

-continued

Compound 46
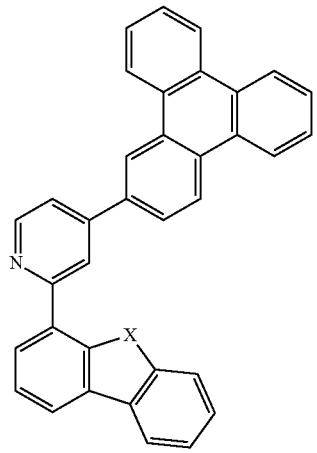

Compound 47 G
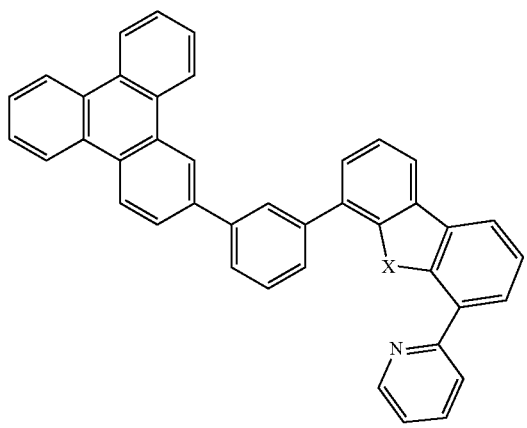

Compound 47

-continued

Compound 48 G
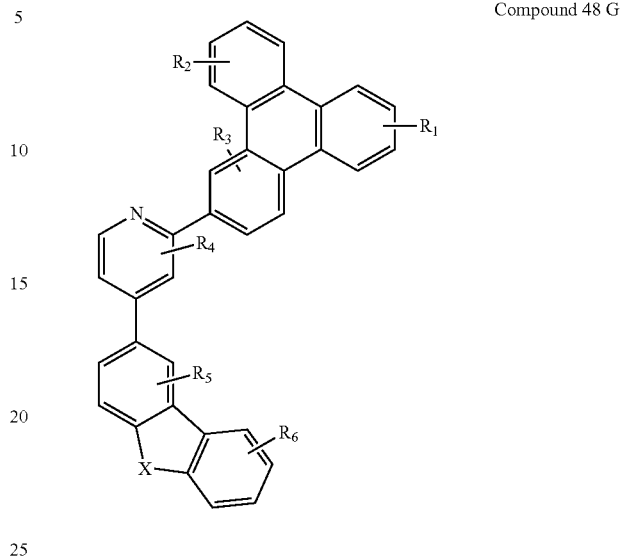

Compound 48
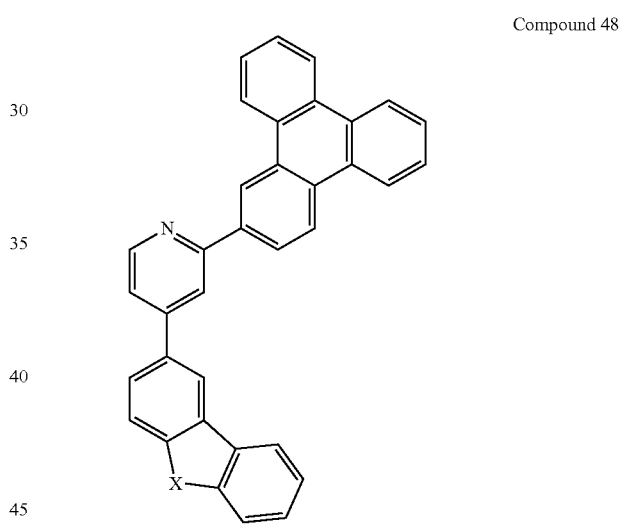

X is S or O. Preferably, X is S. $R_1$ to $R_n$ are independently selected from the group consisting of $C_nH_{2n+1}$, $OC_nH_{2n+1}$, $OAr_1$, $N(C_nH_{2n+1})_2$, $N(Ar_1)(Ar_2)$, $CH=CH-C_nH_{2n+1}$, $C\equiv CC_nH_{2n+1}$, $Ar_1$, $Ar_1-Ar_2$, $C_nH_{2n}-Ar_1$, or no substitution. Each of $R_1$ to $R_n$ may represent mono, di, tri, or tetra substitutions. n is 1, 2, 3, 4, 5, 6, 7, 8, 9, or 10. $Ar_1$ and $Ar_2$ are independently selected from the group consisting of benzene, biphenyl, naphthalene, triphenylene, carbazole, and heteroaromatic analogs thereof. At least one of $R_1$, $R_2$, and $R_3$ includes a triphenylene group.

Each of the triphenylene-containing benzo-fused thiophenes disclosed above may be advantageously used in an organic light emitting device. The compounds are particularly useful for use as the host of an emissive layer in an organic light emissive device, an enhancement layer material of such a device, or both.

EXPERIMENTAL

Compound Examples

Example 1

4-(triphenylen-2-yl)dibenzothiophene (Compound 1S)

1. Synthesis of 2-Bromotriphenylene

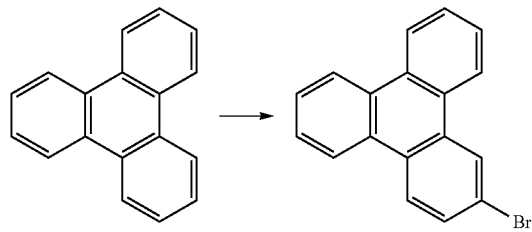

The synthesis of the compound above was described in US20060280965.

2. Synthesis of 4-(triphenylen-2-yl)dibenzothiophene 4.4 g (14.6 mmol) of 2-bromotriphenylene, 4.0 g (17.5 mmol) of 4-dibenzothiopheneboronic acid, 0.51 g (0.44 mmol) of tetrakistriphenylphosphinepalladium, and 4.0 g (43.4 mmol) of potassium carbonate were charged in a 250 mL round bottom flask with solvent 90 mL of toluene and 10 mL of water. The reaction mixture was purged with nitrogen for 30 min and then was heated up to reflux for overnight under nitrogen with stirring. The reaction mixture was cooled and the organic extracts were purified by column chromatography and recrystallization with toluene. 5.1 g (86%) of white solid was obtained as the product which was confirmed by proton NMR.

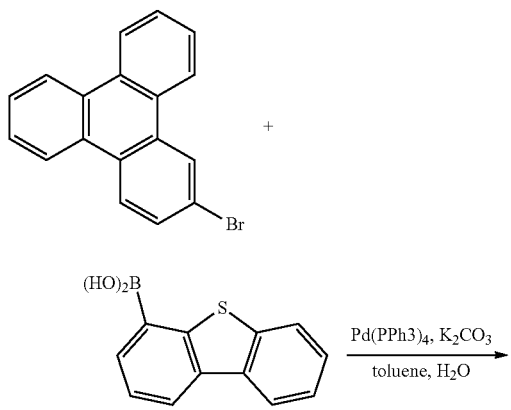

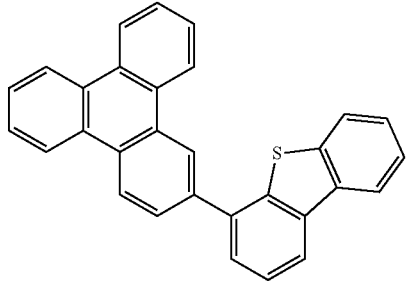

Compound 1S

Example 2

4-(3-(triphenylen-2-yl)phenyl)dibenzothiophene (Compound 2S)

1. Synthesis of 3-(2-triphenylene)phenyl trifluoromethanesulfonate

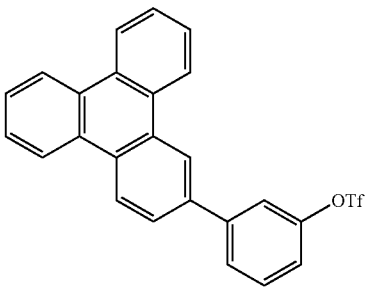 [SMILES: O=S(=O)(Oc1cccc(-c2ccc3c4ccccc4c4ccccc4c3c2)c1)C(F)(F)F]

The synthesis of the above compound was described Provisional Application No: 60/963,944.

2. Synthesis of 4-(3-(triphenylen-2-yl)phenyl)dibenzothiophene 4.52 g (10.0 mmol) of 3-(triphenylen-2-yl)phenyl trifluoromethanesulfonate, 3.0 g (13.0 mmol) of 4-dibenzothiopheneboronic acid, 0.46 g (0.5 mmol) of $Pd_2(dba)_3$, 0.82 g (2.0 mmol) of 2-dicyclohexylphosphino-2',6'-dimethoxybiphenyl, 12.7 g (60.0 mmol) of $K_3PO_4$ and 150 mL of toluene and 15 mL of water were charged in a 250 mL round bottom flask. The reaction mixture was heated up to reflux under nitrogen for overnight. The reaction mixture was cooled and the organic extracts were purified by column chromatography and recrystallization. 4.3 g (88%) of white solid was obtained as product which was confirmed by proton NMR.

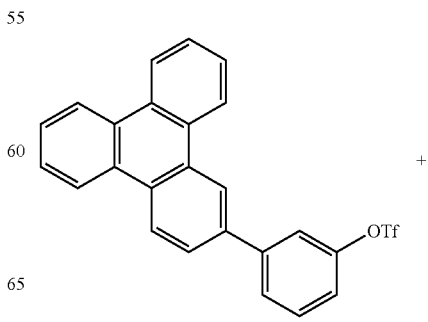

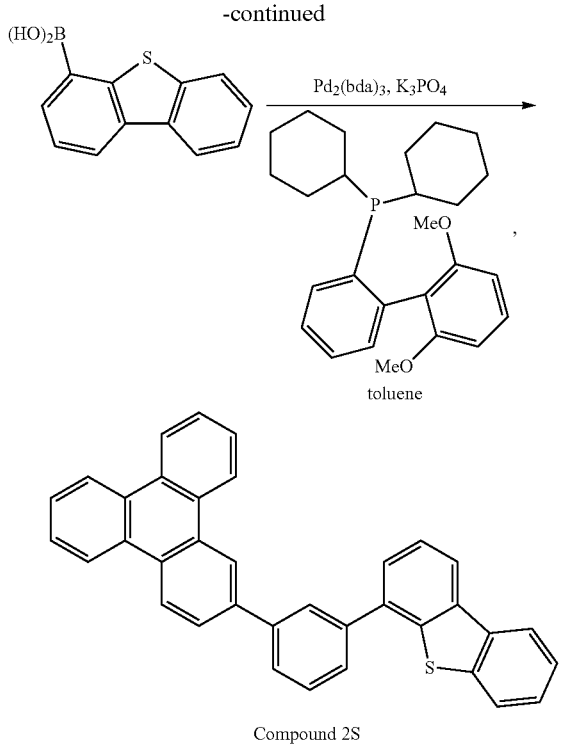

Example 3

2,8-di(triphenylen-2-yl)dibenzothiophene (Compound 5S)

1. Synthesis of 4,4,5,5-tetramethyl-2-(triphenylen-2-yl)-1,3,2-dioxaborolane

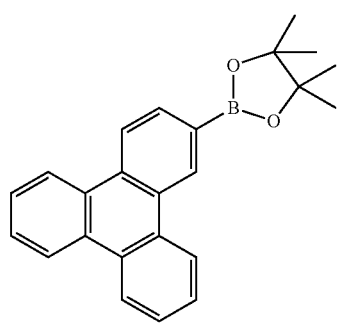 [SMILES: CC1(C)OB(c2ccc3c4ccccc4c4ccccc4c3c2)OC1(C)C]

The synthesis of this compound was described in US2006/0280965.

1. Synthesis of 2,8-di(triphenylen-2-yl)dibenzothiophene 2.25 g (6.3 mmol) of 4,4,5,5-tetramethyl-2-(triphenylen-2-yl)-1,3,2-dioxaborolane, 0.92 g (2.7 mmol) of 2,8-dibromodibenzothiophene, 0.12 g (0.14 mmol) of Pd₂(dba)₃, 0.22 g (0.53 mmol) of 2-dicyclohexylphosphino-2',6'-dimethoxybiphenyl, 3.4 g (16.0 mmol) of K₃PO₄, 100 mL of toluene and 10 mL of water were charged in a 250 mL round bottom flask. The reaction mixture was purged with nitrogen for 20 min and then heated up to reflux for overnight with stirring. The reaction mixture was cooled and filtered. The white solid was washed with methanol 3 times (3×100 mL) and methylene chloride (2×100 mL). 1.6 g of (94% yield) solid was obtained as the product which was further purified by recrystallization with toluene and sublimation. The product was confirmed by solid probe MS.

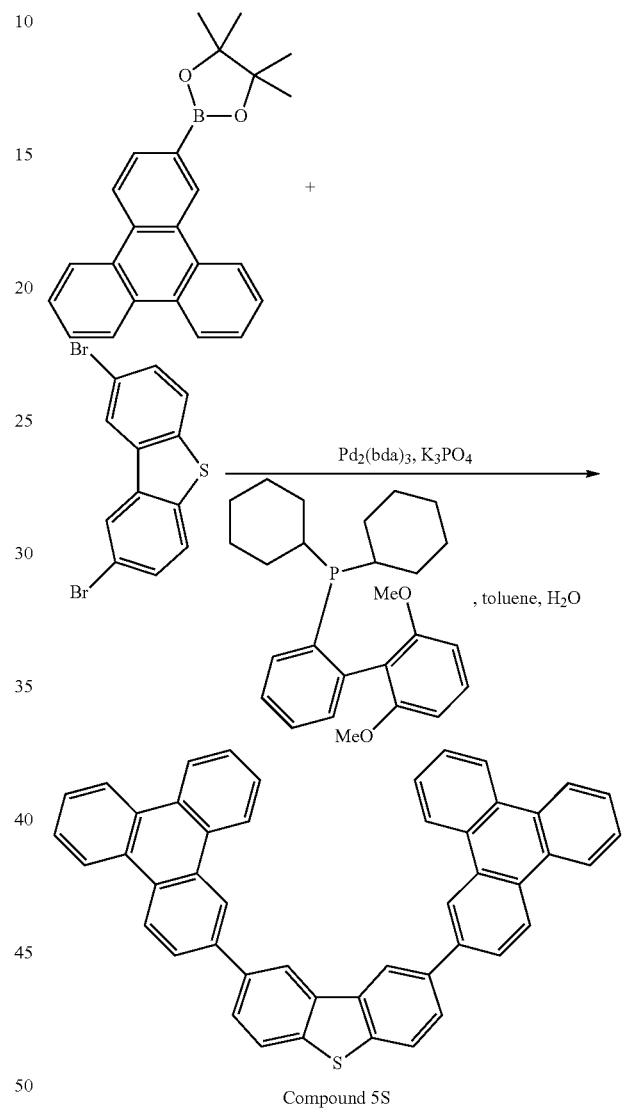

Example 4

Compound 20S

1. Synthesis of 2-bromodibenzothiophene 15 g (79.9 mmol) dibenzothiophene was dissolved in 1.5 L chloroform. To the solution, 12.76 g (79.9 mmol) bromine was added dropwise. The reaction mixture was vigorously stirred for 2 days at room temperature and then treated with sodium sulfite water solution. The organic phase was evaporated to give a white solid which has 48% unreacted dibenzothiophene, 50% 2-bromodibenbzothiophene and ~less 2% 2,8-dibromodibenzothiophene based on GC-MS and HPLC results. The mixture was repeatedly recrystallized with ethyl acetate to get pure 2-bromodibenzothiophene.

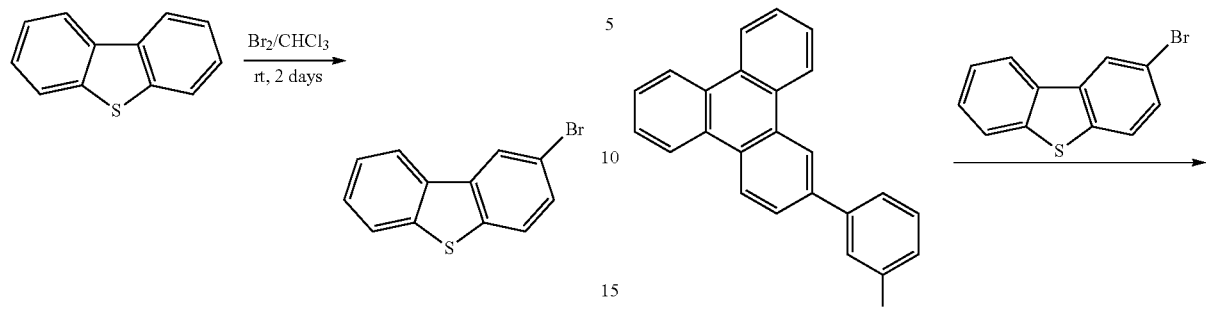

2. Synthesis of Boron Ester Product 8 g (17.5 mmol) 3-(2-triphenylene)phenyl trifluoromethanesulfonate, 9.1 g (35.2 mmol) bis(pinacolato)diboron, 290 mg (0.35 mmol) Pd(dffp)$_2$Cl$_2$, 5.2 g (52.5 mmol) KOAc and 150 mL anhydrous dioxane were charged in a 250 mL three-necked flask. The reaction mixture was heated up to 90° C. under nitrogen for 20 hours. 7.0 g white solid was obtained after column with 30% ethyl acetate in hexane as elute. The product was confirmed by proton NMR.

3. Synthesis of Compound 20S 2 g (7.1 mmol) 2-bromodibenzothiophene, 4.0 g (9.3 mmol) boron ester product in Step 2, 325 mg (0.355 mmol) Pd$_2$(dba)$_3$, 582 g (1.4 mmol) S-phose, 9 g (42 mmol) K$_3$PO$_4$, 90 mL toluene and 10 mL water were charged in a 250 mL flask. The reaction mixture was heated up to reflux under nitrogen for overnight. The reaction mixture was extracted with methylene chloride and the organic extracts were purified by silica gel column chromatography and recrystallization. ~2.9 g (85%) white solid was obtained as product which was confirmed by proton NMR.

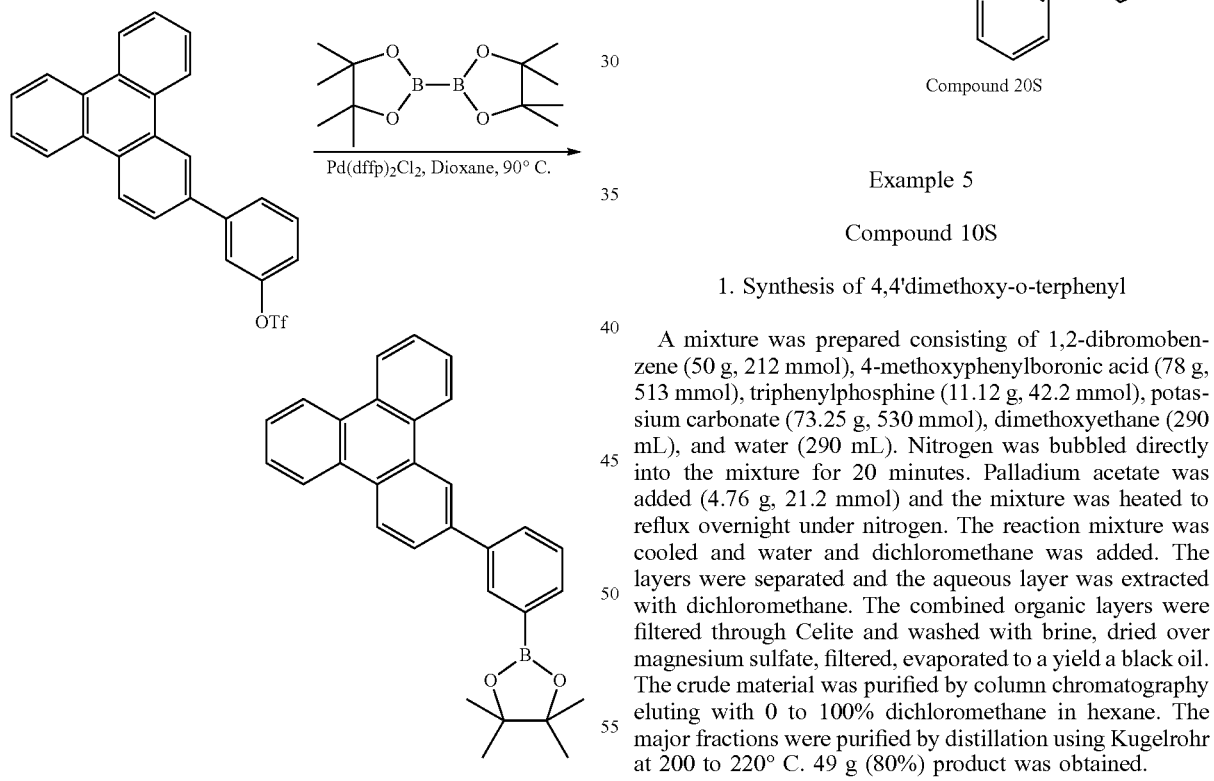

Compound 20S

Example 5

Compound 10S

1. Synthesis of 4,4'dimethoxy-o-terphenyl

A mixture was prepared consisting of 1,2-dibromobenzene (50 g, 212 mmol), 4-methoxyphenylboronic acid (78 g, 513 mmol), triphenylphosphine (11.12 g, 42.2 mmol), potassium carbonate (73.25 g, 530 mmol), dimethoxyethane (290 mL), and water (290 mL). Nitrogen was bubbled directly into the mixture for 20 minutes. Palladium acetate was added (4.76 g, 21.2 mmol) and the mixture was heated to reflux overnight under nitrogen. The reaction mixture was cooled and water and dichloromethane was added. The layers were separated and the aqueous layer was extracted with dichloromethane. The combined organic layers were filtered through Celite and washed with brine, dried over magnesium sulfate, filtered, evaporated to a yield a black oil. The crude material was purified by column chromatography eluting with 0 to 100% dichloromethane in hexane. The major fractions were purified by distillation using Kugelrohr at 200 to 220° C. 49 g (80%) product was obtained.

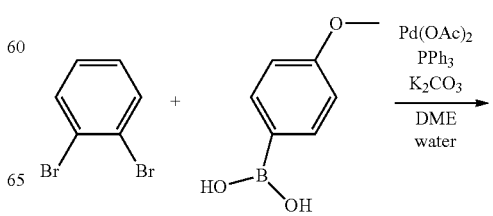

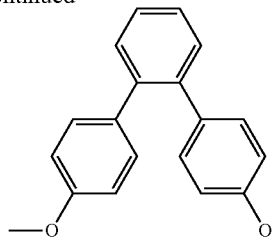

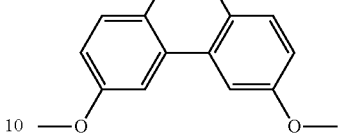

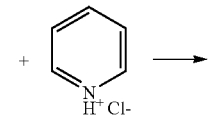

2. Synthesis of 2,11-dimethoxytriphenylene 12.4 g (42.7 mmol) of 4,4'dimethoxy-o-terphenyl and 16 g (63.0 mmol) iodine chips was placed in a 250 mL reaction vessel. 200 mL of toluene was added followed by 30 mL of propylene oxide. The photoreactor was set up with a condenser cooled by a circulating chiller. A 400 W medium pressure mercury lamp was used as the light source. The reaction vessel was placed in a cabinet. The lamp was ignited and the chiller temperature was set such that the water exiting the reactor was maintained at between 20° C. and 25° C. (monitored by a thermocouple attached the exit stream). The reaction was left on for 18 hours. A solid was filtered off and washed with hexanes, only recovered 2.2 g of material. The filtrate was diluted with toluene and washed with sodium sulfate solution. The aqueous layer was back extracted with toluene and the organic layers were dried over magnesium sulfate, filtered, and evaporated. Material was dissolved in toluene and added sodium sulfite solution and stirred. The layers were separated, the aqueous layer extracted with toluene and the combined organic layers were dried over magnesium sulfate, filtered, and evaporated. The residue was purified by column chromatography eluting with 0 to 100% ethyl acetate/hexane. 8.8 g material (72%) was obtained.

3. Synthesis of triphenylene-2,11-diol

A mixture of 2,11-dimethoxytriphenylene (8.8 g, 30.5 mmol) and pyridine hydrochloride (31.73 g, 274.6 mmol) was heated to 220° C. for 2 hours. The mixture was cooled and water was added. The resulting solid was filtered off, washed with water, and dried under high vacuum. 7.45 g (94%) desired product was obtained.

4. Synthesis of triphenylene-2,11-diyl bis(trifluoromethanesulfonate)

Triphenylene-2,11-diol (7.45 g, 28.62 mmol) was added to 100 mL dichloromethane and 13 mL pyridine and the solution was cooled in an ice salt bath. Trifluoromethanesulfonic anhydride (19 mL, 114.49 mmol) in 70 mL of dichloromethane was added dropwise to the solution under nitrogen. The reaction was allowed to proceed for 2 hours and quenched by adding by adding methanol and water followed by dilution with dichloromethane. A tan solid was filtered off and washed with dichloromethane and water. The layers in the filtrate were separated and the aqueous layer was extracted with dichloromethane. The organic extracts were dried over magnesium sulfate, filtered, and evaporated to yield a brown solid. The brown solid was purified by column chromatography eluting with 0 to 100% dichloromethane/hexane following sublimation at 170° C. and recrystallization twice from 300 mL boiling toluene. 11.4 g product was obtained (76%).

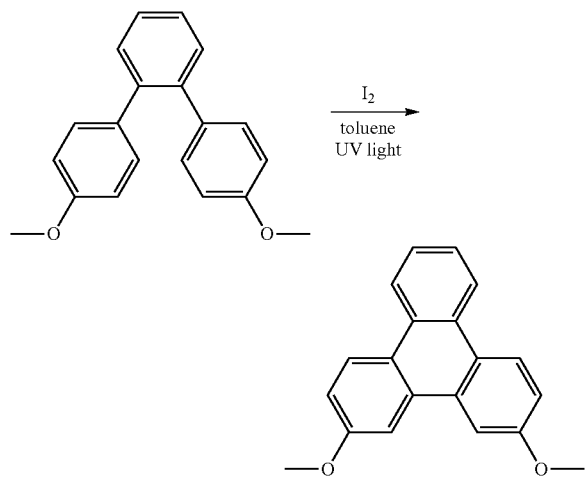

5. Synthesis of Compound 10S

A mixture of triphenylene-2,11-diyl bis(trifluoromethanesulfonate) (1.5 g, 2.9 mmol), dibenzothiophene-4-boronic acid (2.6 g, 11.4 mmol), potassium fluoride (1.1 g, 19 mmol) and THF 50 mL was prepared. Nitrogen was bubbled directly in the mixture for 1 hour. Next potassium acetate (13 mg, 0.06 mmol) and triscyclohexyl phosphine (19 mg, 0.07 mmol) was added, and then nitrogen was bubbled in the mixture for another 30 minutes. The mixture was heated at 50° C. overnight. Then the reaction was cooled to room temperature. The precipitation was collected by filtration. The white solid was put in one soxhlet extractor and washed by refluxing THF overnight. The solid in the extractor was collect to provide 0.9 gram white solid (yield 53%).

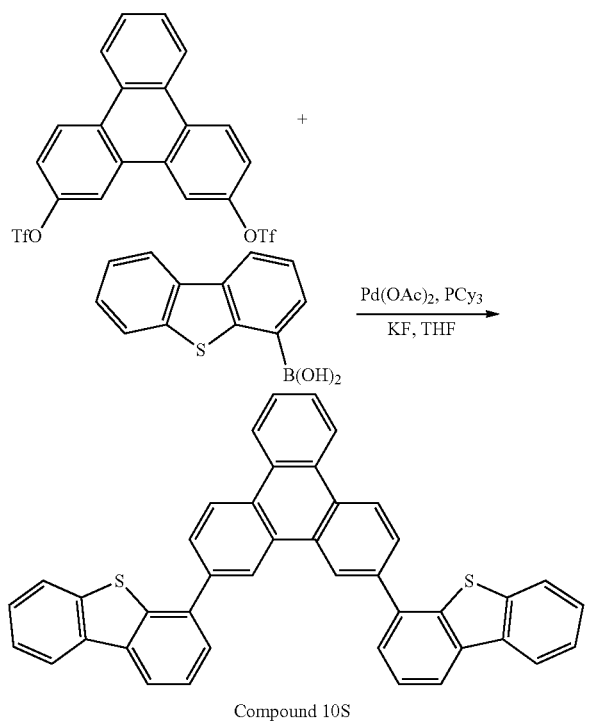

Compound 10S

Example 6

Compound 9S

1. Synthesis of 2-(3'-methoxybiphenyl-3-yl)triphenylene 12.9 g (28.5 mmol) 3-(triphenylen-2-yl)phenyl trifluoromethanesulfonate, 6.5 g (42.8 mmol) 3-methoxyphenylboronic acid, 0.47 g (1.1 mmol) 2-dicyclohexylphosphino-2',6'-dimethoxybiphenyl (SPhos) and 18.2 g (85.5 mmol) potassium phosphate tribasic ($K_3PO_4$) were weighed in a round bottom flask. 150 mL toluene and 80 mL water were added to the flask as solvent. The solution was purged with nitrogen and 0.26 g (0.28 mmol) of tris(dibenzylideneacetone)dipalladium (0) [$Pd_2(dba)_3$] was added. The solution was heated to reflux for twelve hours. Upon cooling, the organic layer was separated, and dried with $MgSO_4$. The product was readily separated by column chromatography using hexane/dichloromethane as eluent (1/0 gradient to 3/2). The solvent was removed by rotary evaporation resulting in 11.7 g (28 mmol) of the product, 2-(3'-methoxybiphenyl-3-yl)triphenylene.

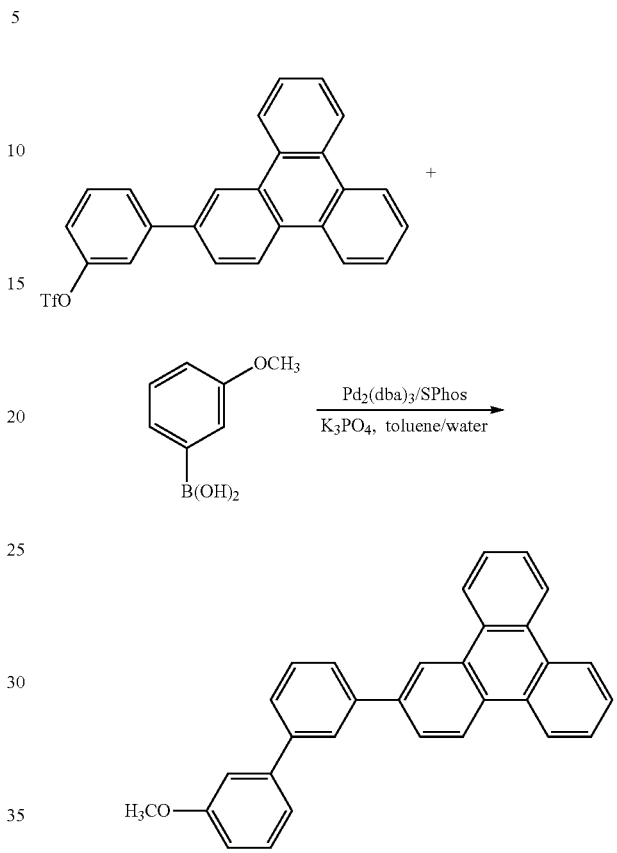

2. Synthesis of 3'-(triphenylen-2-yl)biphenyl-3-ol

In a round bottom flask under nitrogen, 11.5 g (28 mmol) 2-(3'-methoxybiphenyl-3-yl)triphenylene and 21.1 g (183 mmol) pyridine hydrochloride were heated to 204° C. Upon cooling, water was added and extracted with dichloromethane. The combined organic fractions were washed with additional water and the solvent was removed by rotary evaporation. The solid was drypacked on celite and the product purified by column chromatography using hexanes:dichloromethane (1:4) as eluent. The solvent was removed by rotary evaporation resulting in 8.6 g (22 mmol) of the product, 3'-(triphenylen-2-yl)biphenyl-3-ol.

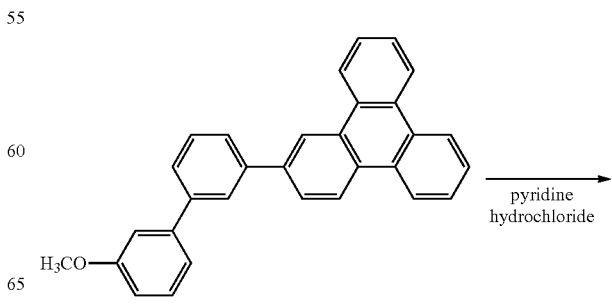

3. Synthesis of 3'-(triphenylen-2-yl)biphenyl-3-yl trifluoromethanesulfonate 8.6 g (22 mmol) of 3'-(triphenylen-2-yl)biphenyl-3-ol was added to a flask under nitrogen with 3.4 g (43.4 mmol) anhydrous pyridine and 450 mL anhydrous dichloromethane. The solution was cooled in an ice bath and 12.2 g (43.4 mmol) trifluoromethanesulfonic anhydride (Tf$_2$O) was added slowly via syringe. The solution was warmed to room temperature and stirred overnight. The solution was washed with water, dried with MgSO$_4$ and solvent was removed by rotary evaporation. The product, 3'-(triphenylen-2-yl)biphenyl-3-yl trifluoromethanesulfonate, was purified by column chromatography using hexane/dichloromethane as eluent (1/0 to 1/1 gradient) resulting in 10.7 g (20.2 mmol).

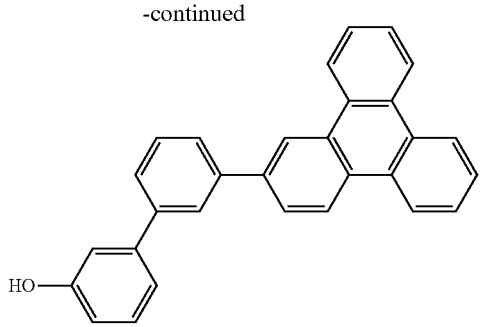

4. Synthesis of Compound 9S 5.5 g (10.4 mmol) product in above Step 3, 3.0 g (13.5 mmol) 4-boronic acid dibenzothiophene, 458 mg (0.5 mmol) Pd$_2$(dba)$_3$, 820 mg (2 mm01) S-phose, 12.7 g (60 mmol) potassium phosphate and 150 mL toluene were added in a 250 flask. The reaction mixture was heated up to reflux under nitrogen overnight. Then it was cooled down and worked up. ~5 g white product was obtained after silica gel column chromatography with 20% methylene chloride in hexane as elute and following with washing with methanol. The product was confirmed by proton NMR.

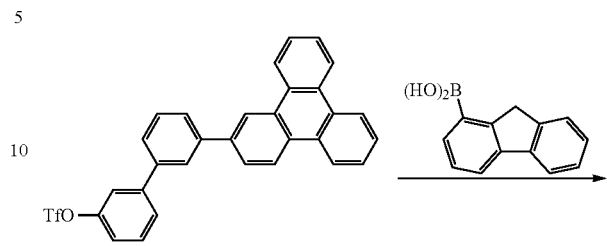

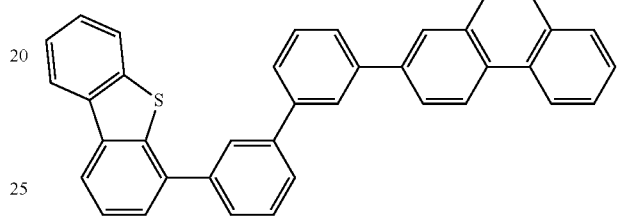

Compound 9S

Example 7

Compound 19S

1. Synthesis of 3,3'-dimethoxy-o-terphenyl 1,2-dibromobenzene (50.0 g, 0.212 mol), 3-methoxyphenylboronic acid (77.3 g, 0.509 mol), palladium acetate (1.2 g, 5.33 mmol), triphenylphosphine (21.4 mmol), sodium carbonate (78.9 g, 0.744 mol) were combined with dimethoxyethane (430 mL) and water (290 mL) in a 2000 mL round-bottom flask equipped with a stir bar, reflux condenser, and a nitrogen inlet and heated at reflux for 4 days. Ethyl acetate (500 mL) was added and the organic layer was separated, dried over magnesium sulfate, and evaporated to dryness to yield 61.3 g (99.7%) of 3,3'-dimethoxy-o-terphenyl as a white solid.

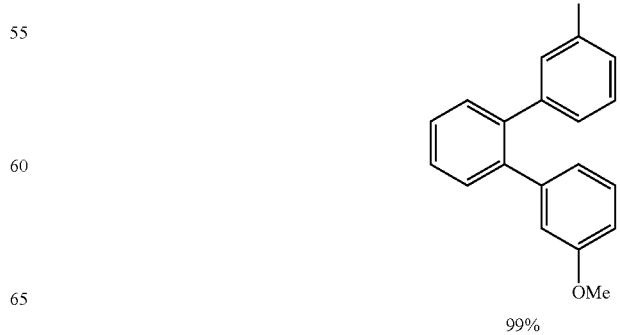

2. Synthesis of 2,9-dimethoxytriphenylene

In a 2000 mL round-bottom flask equipped with a nitrogen inlet and a stir bar, 3,3'-dimethoxy-o-terphenyl (61.3 g, 0.211 mol) was dissolved in anhydrous methylene chloride (1000 mL). Iron (III) chloride (68.6 g, 0.423 mol) was then added, and the mixture was stirred overnight. In the morning an additional two equivalents of iron (III) chloride were added, and the reaction reached completion within one hour. Methanol and water were added to the mixture and the organic layer was separated, dried over magnesium sulfate, and evaporated to dryness. The crude product was purified by silica gel column chromatography with 60/40 methylene chloride/hexane was the eluent to give 50.7 g of a light yellow solid that was recrystallized from 700 mL of acetonitrile to yield 49.1 g of 2,9-dimethoxytriphenylene.

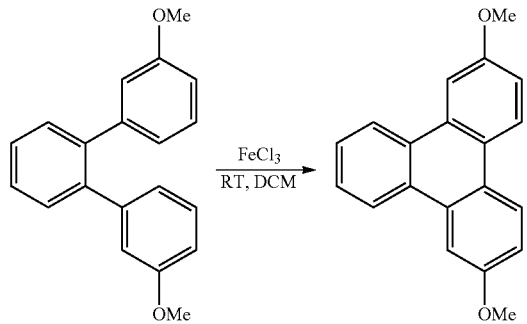

3. Synthesis of 2,9-dihydroxytriphenylene 2,9-dimethoxytriphenylene (49.1 g, 0.170 mol) and pyridine hydrochloride (200 g, 1.70 mol) were placed in a 500 mL round-bottom flask equipped with a stir bar, reflux condenser, and a nitrogen inlet and heated at 220° C. for 90 minutes. The solution was cooled and water was added, resulting in the formation of a white precipitate, which was collected by vacuum filtration, washed with water, and dried in vacuo to yield 43.7 g (96%) of 2,9-dihydroxytriphenylene.

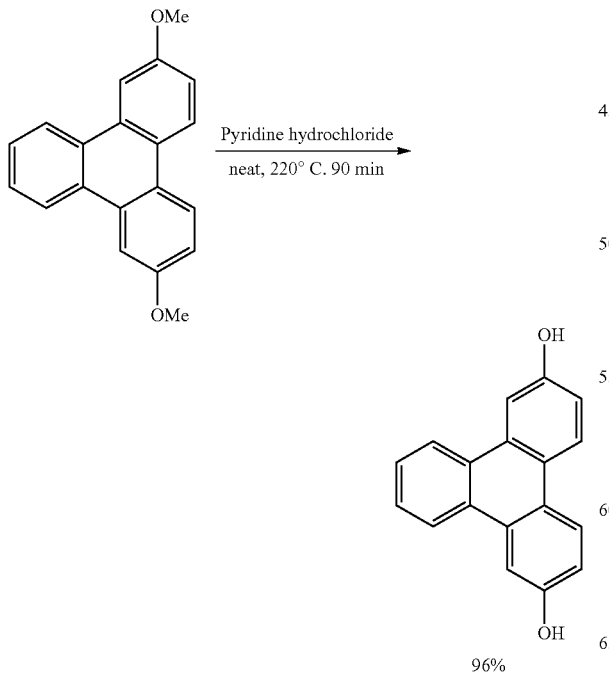

4. Synthesis of triphenylene-2,7-diyl bis(trifluoromethanesulfonate)

To a cooled solution (0° C.) of 2,9-dihydroxytriphenylene (17.5 g, 65 mmol) and pyridine (300 mL) in a 1000 mL round bottom flask equipped with a stir bar and nitrogen inlet was added dropwise trifluoromethanesulfonyl anhydride (38.7 g, 137 mmol). The reaction mixture was allowed to stir overnight at room temperature. After evaporation of the pyridine, the resulting solid was stirred with methanol (500 mL) and collected by vacuum filtration to afford 32 g of a white powder that was recrystallized from 500 mL of 30/70 heptane/dichloroethane, yielding 28.3 g (82%) of 2,9-bis(trifluoromethanesulfonyl)triphenylene.

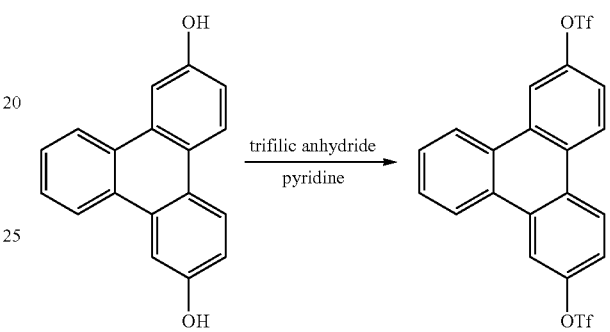

5. Synthesis of Compound 19S

A mixture of triphenylene-2,7-diyl bis(trifluoromethanesulfonate) (2 g, 3.8 mmol), dibenzothiophene-4-boronic acid (3.5 g, 15 mmol), potassium fluoride (1.5 g, 25 mmol) and THF 100 mL was prepared. Nitrogen was bubbled directly in the mixture for 1 hour. Next potassium acetate (17 mg, 0.08 mmol) and triscyclohexyl phosphine (26 mg, 0.09 mmol) were added, and then the nitrogen was bubbled in the mixture for another 30 minutes. The mixture was stirred at room temperature for two days. Then the reaction was cooled to room temperature. The precipitation was collected by filtration. Potassium acetate (17 mg, 0.08 mmol) and triscyclohexyl phosphine (26 mg, 0.09 mmol) were added and then the nitrogen was bubbled in the mixture for another 15 minutes. The mixture was stirred at room temperature for another two days. The grey solid was put in one soxlet extractor and washed by refluxing THF overnight. The solid in the extractor was collect to provide 2.1 gram white solid (yield 92%).

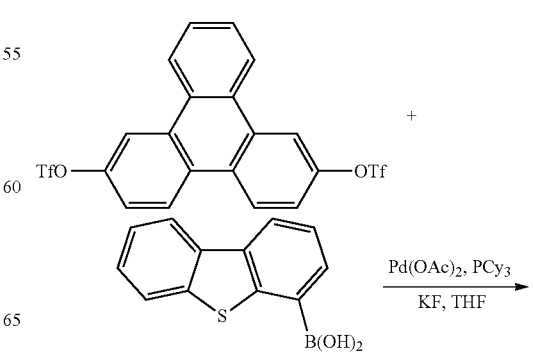

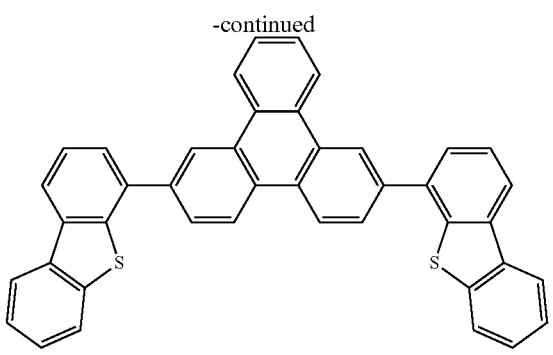

Compound 19S

Example 8

Compound 22S

Step 1

A mixture of 2,6-dichloropyridine (13 g, 88 mmol), dibenzothiophene-4-boronic acid (5 g, 22 mmol), potassium phosphate tribasic (28 g, 132 mmol), toluene 300 mL and water 30 mL was prepared. Nitrogen was bubbled directly in the mixture for 1 hour. Next tris dibenzylideneacetone (0.54 g, 1.3 mmol) was added, and then nitrogen was bubbled into the mixture for another 20 minutes. The mixture was stirred at room temperature for two days. Then the organic layer was collected and the aqueous layer was extracted by dichloromethane. The combined organic layers were dried over magnesium sulfate and concentrated. The crude product was purified by silica gel flash chromatography with up to 10% ethyl acetate in hexanes to give 5 grams of yellow solid. It was further recrystallized from dichloroethane/heptane to obtain 2.5 grams of white sold (39%).

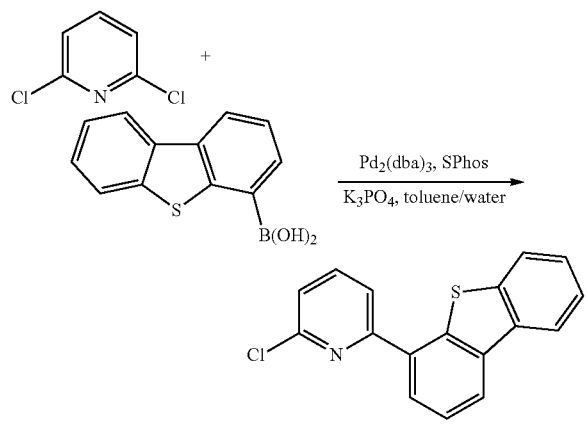

2. Synthesis of Compound 22S

A mixture of 4,4,5,5-tetramethyl-2-(triphenylen-2-yl)-1,3,2-dioxaborolane (2.2 g, 6.1 mmol), 2-chloro-6-(dibenzothiophen-4-yl)pyridine (1.5 g, 5.1 mmol), potassium phosphate tribasic (3.3 g, 15.3 mmol), toluene 150 mL and water 15 mL was prepared. Nitrogen was bubbled directly in the mixture for 40 minutes. Next tris dibenzylideneacetone dipalladium (56 mg, 0.06 mmol) and bis(cyclohexyl)-2-biphenylphosphine (100 mg, 0.24 mmol) were added, and then nitrogen was bubbled in the mixture for another 17 minutes. The reaction mixture was refluxed overnight under nitrogen. The precipitation was collected by filtration and washed by toluene, dichloromethane and methanol. Then the product was dissolved in 250 mL boiling xylene, filtered through a small magnesium sulfate plug. The filtration was heated to reflux to dissolve all the solid and allowed to slowly cool down. The recrystallized product was obtained as 2.3 gram white solid (93%).

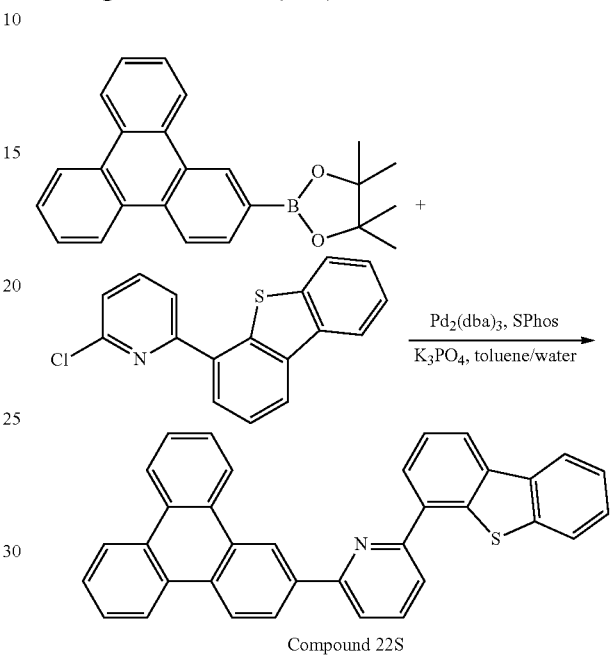

Compound 22S

Example 9

Compound 21S

1. Synthesis of 2-chloro-6-(3-methoxyphenyl)pyridine

A mixture of m-methoxy-phenylboronic acid (10 g, 65.8 mmol), 2,6-dichloropyridine (9.7 g, 65.8 mmol), potassium carbonate (27.3 g, 197.4 mmol), triphenylphosphine (2.07 g, 7.9 mmol), dimethoxyethane 250 mL and water 80 mL was prepared. Nitrogen was bubbled directly in the mixture for 20 minutes. Then palladium acetate was added (0.44 g, 2.0 mmol). Nitrogen was bubbled again in the mixture for another 10 minutes. The mixture was heated to reflux under nitrogen overnight. The reaction mixture was cooled to room temperature. The organic layer was separated and the aqueous layer was extracted with dichloromethane. The combined organic layers were dried over magnesium sulfate, filtered and evaporated. The mixture was purified by silica column with up to 10% ethyl acetate in hexanes to gain 6.5 g colorless oil (45%).

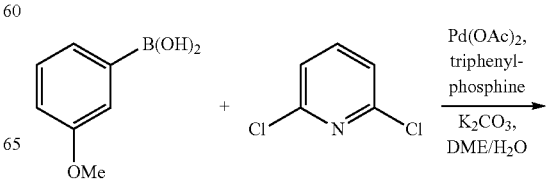

-continued

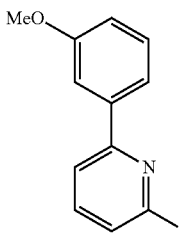

2. Synthesis of 2-(dibenzo[b,d]thiophen-4-yl)-6-(3-methoxyphenyl)pyridine

A mixture of 2-chloro-6-(3-methoxyphenyl)pyridine (3.5 g, 16 mmol), dibenzothiophene-4-boronic acid (4 g, 17.5 mmol), potassium phosphate (10.2 g, 48 mmol), dimethoxyethane 500 mL and water 50 mL was prepared. Nitrogen was bubbled directly in the mixture for 15 minutes. Next tris dibenzylideneacetone dipalladium (147 mg, 0.16 mmol) and 2-dicyclohexylphosphino-2',6'-dimethoxybiphenyl (263 mg, 0.64 mmol) were added, and then nitrogen was bubbled in the mixture for another 15 minutes. The reaction mixture was heated to reflux overnight under nitrogen. The next day the reaction mixture was cooled to room temperature. The organic layer was separated and the aqueous layer was extracted with dichloromethane. The combined organic layers were dried over magnesium sulfate, filtered and evaporated. The mixture was purified by silica column with up to 10% ethyl acetate in hexanes to gain 3.8 g yellow solid (65%).

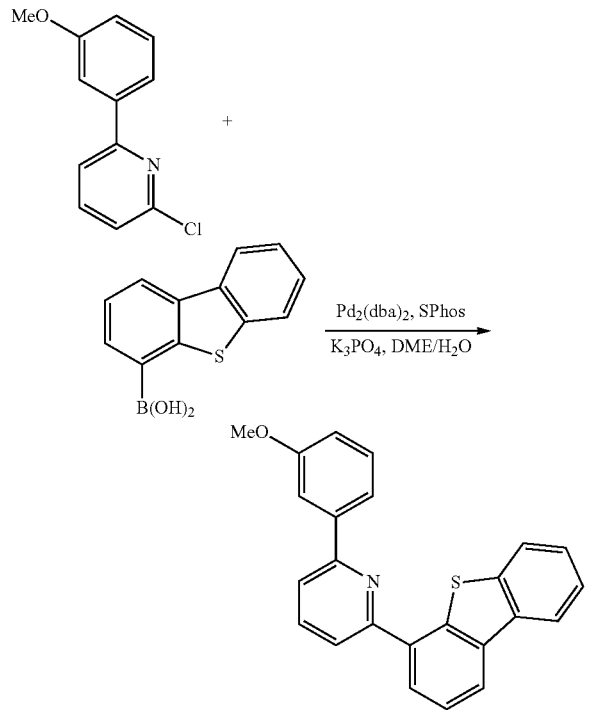

3. Synthesis of 3-(6-(dibenzo[b,d]thiophen-4-yl)pyridin-2-yl)phenol 2-(dibenzo[b,d]thiophen-4-yl)-6-(3-methoxyphenyl)pyridine (3.8 g, 10.3 mmol) was dissolved in 120 mL dichloromethane. The solution was cooled to 0° C. under nitrogen. BBr₃ (22.8 mL, 1M in hexane) was slowly added in at 0° C. and then was slowly brought up to room temperature. The mixture was stirred at room temperature overnight. A brown solid was observed to form. The reaction was quenched by adding 100 mL water slowly. The dichloromethane was removed by rotovap. Then the mixture was refluxed for three hours. Saturated sodium bicarbonate solution was added to neutralize the mixture, which was extracted by dichloromethane and ethyl acetate. The combined organic layers were dried over magnesium sulfate, filtered and concentrated under reduced pressure to obtain 4 gram glassy dark brown solid. The product was used for next step without further purification.

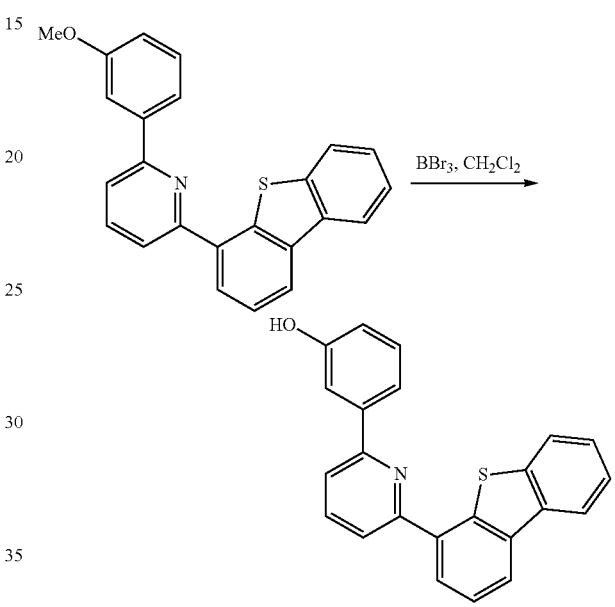

4. Synthesis of 3-(6-(dibenzo[b,d]thiophen-4-yl)pyridin-2-yl)phenyl trifluoromethanesulfonate 3-(6-(dibenzo[b,d]thiophen-4-yl)pyridin-2-yl)phenol (4 g, 11.3 mmol) was suspended in 100 mL pyridine, cooled to −10° C. with acetone/ice bath. Triflate anhydride (2.29 mL, 13.6 mmol) was slowly added under nitrogen. The mixture was stirred at 0° C. for two hours then poured into saturated sodium bicarbonate solution 200 mL. The mixture was extracted by ethyl acetate. The combined organic layers were dried over magnesium sulfate, filtered and evaporated. The mixture was purified by silica column twice with up to 15% ethyl acetate in hexanes. The product was then precipitated from its dichloromethane solution by adding hexanes to gain 1.8 gram white color solid (the combined yield of last two steps is 36%).

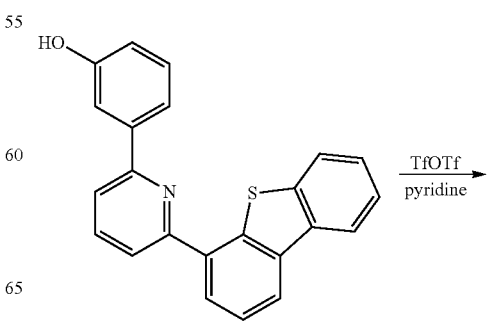

-continued

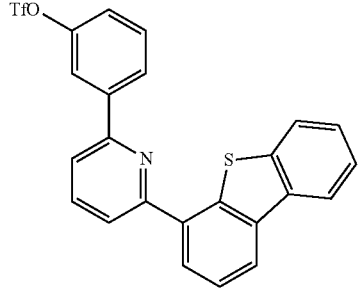

5. Synthesis of Compound 21S

A mixture of 3-(6-(dibenzo[b,d]thiophen-4-yl)pyridin-2-yl)phenyl trifluoromethanesulfonate (1.65 g, 3.4 mmol), 4,4,5,5-tetramethyl-2-(triphenylen-2-yl)-1,3,2-dioxaborolane (1.32 g, 3.7 mmol), potassium phosphate (2.16 g, 10.2 mmol), toluene 100 mL and water 10 mL was prepared. Nitrogen was bubbled directly in the mixture for 25 minutes. Next tris dibenzylideneacetone dipalladium (31 mg, 0.034 mmol) and 2-dicyclohexylphosphino-2',6'-dimethoxybiphenyl (55 mg, 0.14 mmol) were added, and then nitrogen was bubbled in the mixture for another 15 minutes. The reaction mixture was heated to reflux for eight hours under nitrogen. The next day the reaction mixture was cooled to room temperature. The residue was collected by filtration, washed by toluene, dichloromethane and methanol excessively to get 1.8 gram grey solid, which was sublimed at 260° C. twice before used for device fabrication.

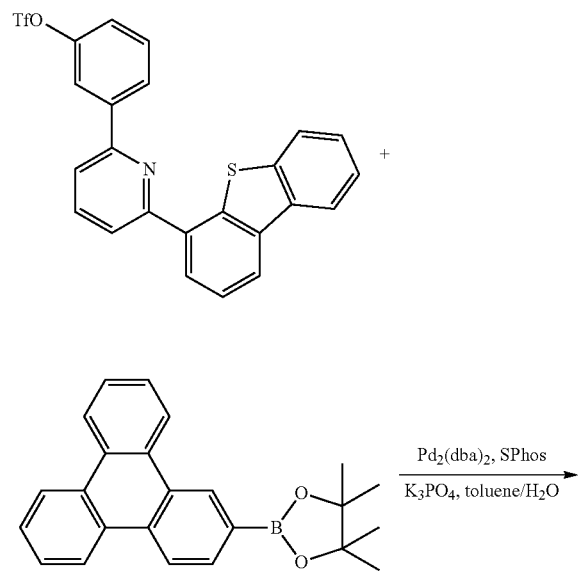

-continued

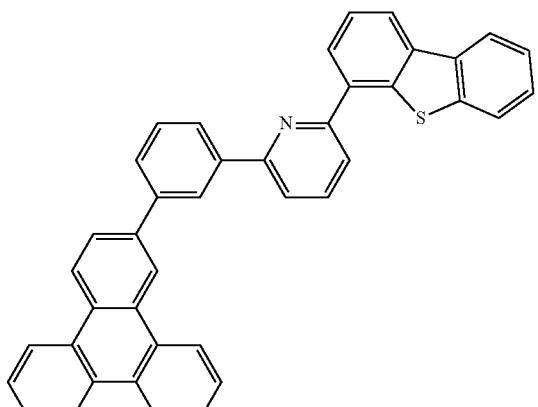

Compound 21S

Example 10

Compound 4S

1. Synthesis of 2,11-bis(3-methoxyphenyl)triphenylenes

A mixture of triphenylene-2,11-diylbis(trifluoromethanesulfonate) (2 g, 3.8 mmol), 3-methoxyphenylboronic acid (2.3 g, 15 mmol), potassium phosphate tribasic (4.8 g, 23 mmol), toluene 100 mL and water 10 mL was prepared. Nitrogen was bubbled directly in the mixture for 30 minutes. Next tris dibenzylideneacetone dipalladium (70 mg, 0.076 mmol) and bis(cyclohexyl)-2-biphenylphosphine (125 mg, 0.30 mmol) were added, and then nitrogen was bubbled in the mixture for another 15 minutes. The reaction was refluxed under nitrogen for three hours. After cooled to room temperature, the organic layer of the reaction mixture was collected, dried over magnesium sulfate, and concentrated under reduced pressure. The crude product was purified by silica gel flash chromatograph to give 1.6 g white solid (yield 95%).

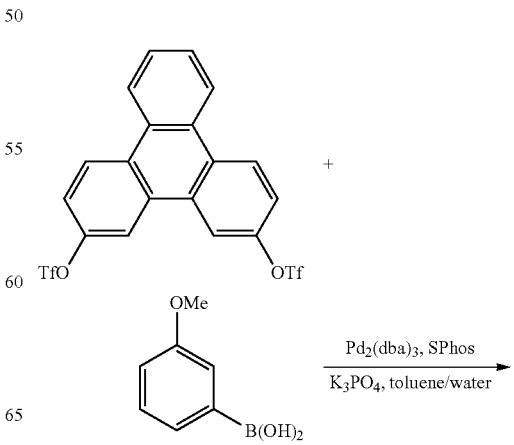

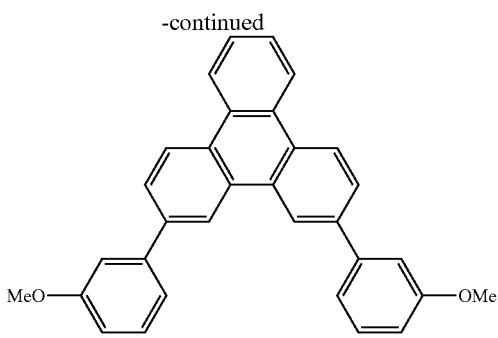

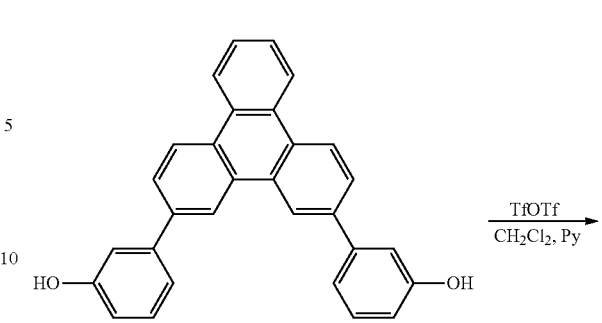

2. Synthesis of 3,3'-(triphenylene-2,11-diyl)diphenole

A mixture of 2,11-bis(3-methoxyphenyl)triphenylene (1.6 g, 3.7 mmol) and pyridine hydrochloride (4.3 g, 37 mmol) was heated to 220° C. under nitrogen for two and half hours. The reaction was cooled to room temperature, and washed with water. The 1.6 g brown residue was collected by filtration, dried under vacuum and was used without further purification for next step.

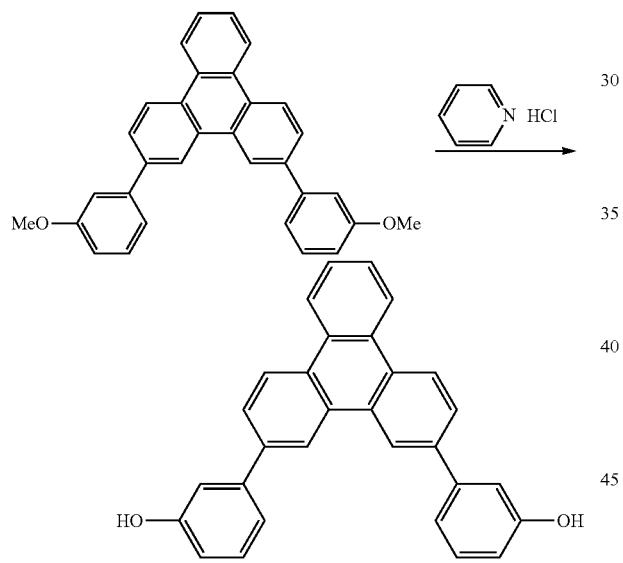

3. Synthesis of 3,3'-(triphenylene-2,11-diyl)bis(3,1-phenylene)bis(trifluoromethanesulfonate)

The 3,3'-(triphenylene-2,11-diyl)diphenole (1.6 g, 3.9 mmol) was suspended in a mixture of 50 mL dichloromethane and 5 mL pyridine. The mixture was cooled to 0° C. by ice/water bath. Triflate anhydride (1.44 mL, 8.5 mmol) was dissolved in 30 mL dichloromethane and slowly added into the reaction mixture under nitrogen at 0° C. Then the reaction was stirred at room temperature under nitrogen overnight. Methanol 20 mL was added to the reaction. The mixture was concentrated by rotovap. The residue was suspended in water then was collected by filtration. After washed with water, the residue was dried under vacuum. The crude product was purified by silica flash chromatograph with up to 30% dichloromethane in hexanes to give white solid 1.6 gram (combined yield of last two steps: 65%).

4. Synthesis of Compound 4S

The mixture of 3,3'-(triphenylene-2,11-diyl)bis(3,1-phenylene)bis(trifluoromethanesulfonate) (1.6 g, 2.4 mmol), dibenzothiophene-4-boronic acid (2.7 g, 12 mmol), potassium phosphate tribasic (3.4 mmol, 16 mmol), toluene 100 mL and water 50 mL was prepared. Nitrogen was bubbled directly in the mixture for 1 hour. Next tris dibenzylideneacetone dipalladium (44 mg, 0.048 mmol) and bis(cyclohexyl)-2-biphenylphosphine (78 mg, 0.19 mmol) were added, and then nitrogen was bubbled in the mixture for another 30 minutes. The reaction was refluxed overnight. After the reaction was cooled to room temperature, the residue was collected by filtration and washed by methanol and dichloromethane to provide final product.

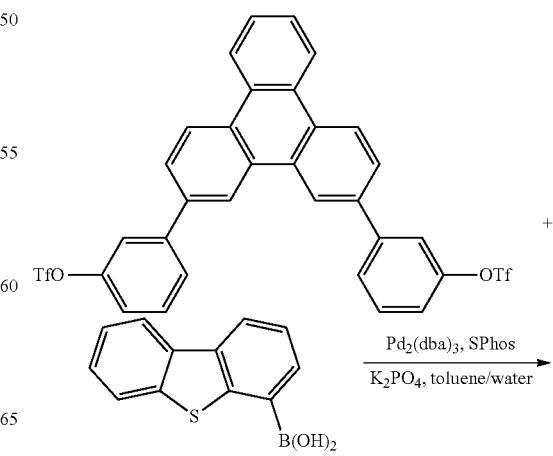

-continued

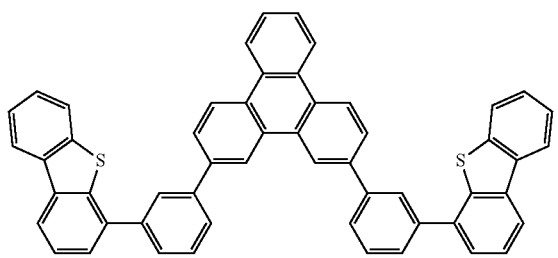

Compound 4S

Example 11

Compound 23S

1. Synthesis of 4-phenyldibenzothiophene 10 g (41.6 mmol) 4-dibenzothiophene boronic acid, 6.25 g (39.6 mmol) bromobenzene, 366 mg (0.39 mmol) Pd$_2$(dba)$_3$, 656 mg (1.6 mmol) S-phose, 25.4 g (120 mmol) K$_3$PO$_4$, 180 mL toluene and 20 mL water were charged in a 500 mL flask. The mixture was heated up to reflux under nitrogen for overnight. The reaction mixture was purified by silica gel column chromatography with pure hexane as elute. ~8.5 g (83%) white solid was obtained as product which was confirmed by MS.

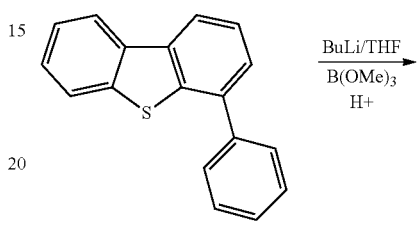

2. Synthesis of 4-phenyldibenzothiophene-6-boronic acid 3.5 g (13.4 mmol) 4-phenyldibenzothiophene was dissolved in ~30 mL anhydrous THF in a three necked 250 mL flask and cooled down to −78° C. To the mixture, 17 mL (27 mmol) 1.6 M BuLi in hexane was added and stirred for 30 minutes. The cooling batch was removed and let reaction kept stirring for overnight. The reaction mixture was cooled down again to −78° C. and 4.5 mL (40 mmol) trimethyl borate was added and stirred at room temperature for 4 hours. ~100.1 M HCl was added and kept stirring for 1 hour. The mixture was extracted by ethyl acetate and the organic extracts were combined. The solvent was evaporated to dryness. The solid was added with ~100 mL 20% ethyl acetate in hexane was stirred for few hours and then filtered. The filtered solid washed by hexane few times. ~2.5 g white solid was obtained as product which was confirmed by proton NMR.

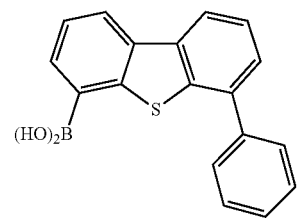

3. Synthesis of Compound 23S 2.4 g (7.89 mmol) above boronic acid, 3.3 g (7.2 mmol) 3-(triphenylen-2-yl)phenyl trifluoromethanesulfonate, 67 mg (0.08 mmol) Pd$_2$(dba)$_3$, 120 mg (0.3 mmol) S-phose, 4.6 g (21.7 mmol) K$_3$PO$_4$, 90 mL toluene and 10 mL water were charged in a 250 mL flask. The mixture was heated up to reflux under nitrogen for 6.5 hours. The reaction mixture was separated with separation funnel and the organic phase was purified by silica gel column chromatography using 20% dichloromethane in hexane as elute and recrystallization from toluene and hexane mixture. ~3.8 g (94%) white solid was obtained as product which was confirmed by proton NMR.

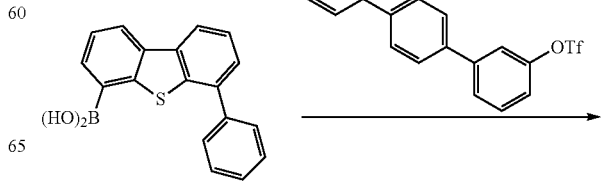

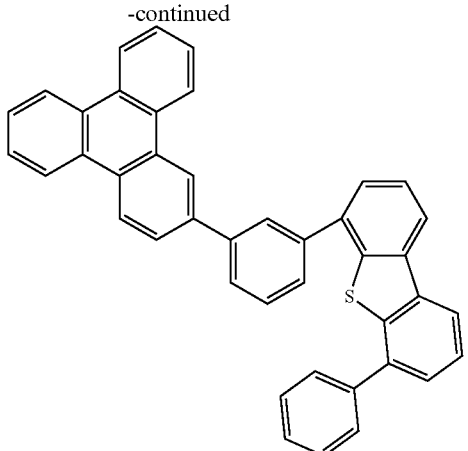

Compound 23S

Example 12

Compound 24S

1. Synthesis of 2,8-diphenylbenzothiophene 7.0 g (20.4 mmol) 2,8-dibromodibenzothiophene, 6.4 g (51.1 mmol) phenylboronic acid, 187 mg (0.2 mmol) Pd$_2$(dba)$_3$, 335 mg (0.8 mmol) S-phose, 13 g (61.2 mmol) K$_3$PO$_4$, 90 mL toluene and 10 mL water were charged in a 250 mL flask. The mixture was heated up to reflux under nitrogen for 4 hours. The reaction mixture was separated with separation funnel and the organic phase was purified by silica gel column chromatography using 20% dichloromethane in hexane as elute. ~6.6 g (96%) white solid was obtained as product which was confirmed by GC-MS.

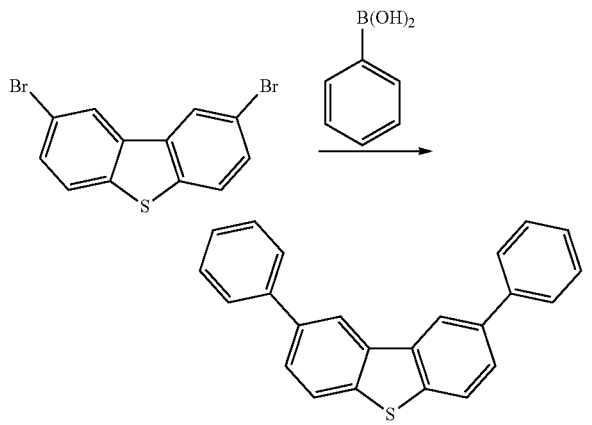

2. Synthesis of 2,8-diphenyldibenzothiophene-4-boronic acid 3.8 g (11.3 mmol) 2,8-diphenylbenzothiophene was dissolved in ~30 mL anhydrous THF in a 250 mL three necked flask. To the mixture, ~18 mL (28.3 mmol) 1.6 M BuLi in hexane was added at −78° C. under nitrogen. The mixture was warmed up to room temperature and kept stirring for 18 hours. The reaction mixture cooled down to −78° C. again and 3.8 mL (34 mmol) trimethyl borate was added and kept mixture stirred for 4 hours at room temperature then added ~60 mL 1M HCl with stirring for 1 hour. The mixture was extracted by ethyl acetate and the organic phases were combined. The solvent was evaporated to dryness. The solid was added with ~100 mL 20% ethyl acetate in hexane. It was stirred for few hours and then filtered. The filtered solid was washed with hexane 3 times. ~2.2 g white solid was obtained as product which was confirmed by proton NMR.

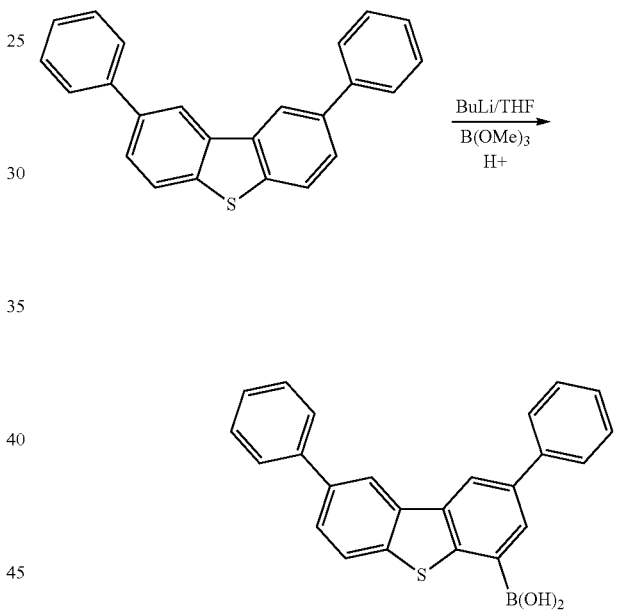

3. Synthesis of Compound 24S 2.0 g (5.26 mmol) 2,8-diphenyldibenzothiophene-4-boronic acid, 2.18 g (4.78 mmol) 3-(triphenylen-2-yl)phenyl trifluoromethanesulfonate, 45 mg (0.05 mmol) Pd$_2$(dba)$_3$, 80 mg (0.19 mmol) S-phose, 3.2 g (14 mmol) K$_3$PO$_4$, 90 mL toluene and 10 mL water were charged in a 250 mL flask. The mixture was heated up to reflux under nitrogen for overnight. The reaction mixture was separated with separation funnel and the organic phase was purified by silica gel column chromatography using 20% dichloromethane in hexane as elute and recrystallization from toluene and hexane mixture. ~2.52 g (84%) white solid was obtained as product which was confirmed by proton NMR.

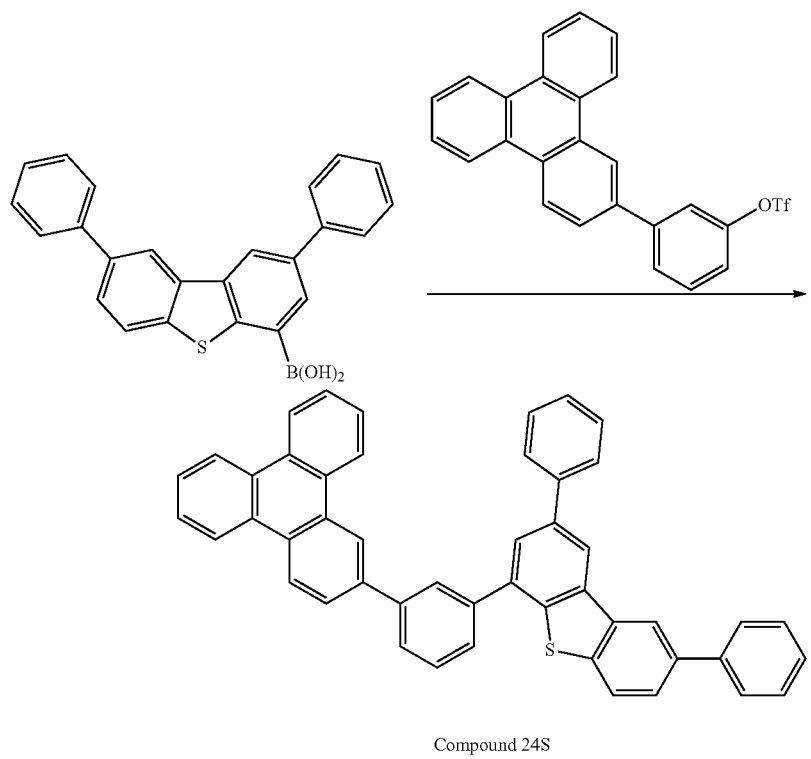

Compound 24S

Example 13

Compound 25S

1. Synthesis of 2,8-diphenylbenzothiophene 7.0 g (20.4 mmol) 2,8-dibromodibenzothiophene, 6.4 g (51.1 mmol) phenylboronic acid, 187 mg (0.2 mmol) $Pd_2(dba)_3$, 335 mg (0.8 mmol) S-phose, 13 g (61.2 mmol) $K_3PO_4$, 90 mL toluene and 10 mL water were charged in a 250 mL flask. The mixture was heated up to reflux under nitrogen for 4 hours. The reaction mixture was separated with separation funnel and the organic phase was purified by silica gel column chromatography using 20% dichloromethane in hexane as elute. ~6.6 g (96%) white solid was obtained as product which was confirmed by GC-MS.

2. Synthesis of 2,8-diphenyldibenzothiophene-4-boronic acid 3.8 g (11.3 mmol) 2,8-diphenylbenzothiophene was dissolved in ~30 mL anhydrous THF in a 250 mL three necked flask. To the mixture, ~18 mL (28.3 mmol) 1.6 M BuLi in hexane was added at −78° C. under nitrogen. The mixture was warmed up to room temperature and was kept stirring for 18 hours. The reaction mixture was cooled down to −78° C. again and 3.8 mL (34 mmol) trimethyl borate was added and the mixture was kept stirring for 4 hours at room temperature. ~60 mL 1M HCl was then added with continuous stirring for 1 hour. The mixture was extracted by ethyl acetate and the organic phases were combined. The solvent was evaporated to dryness. The solid was added with ~100 mL 20% ethyl acetate in hexane was stirred for few hours and then filtered. The filtered solid washed with hexane. ~2.2 g white solid was obtained as product which was confirmed by proton NMR.

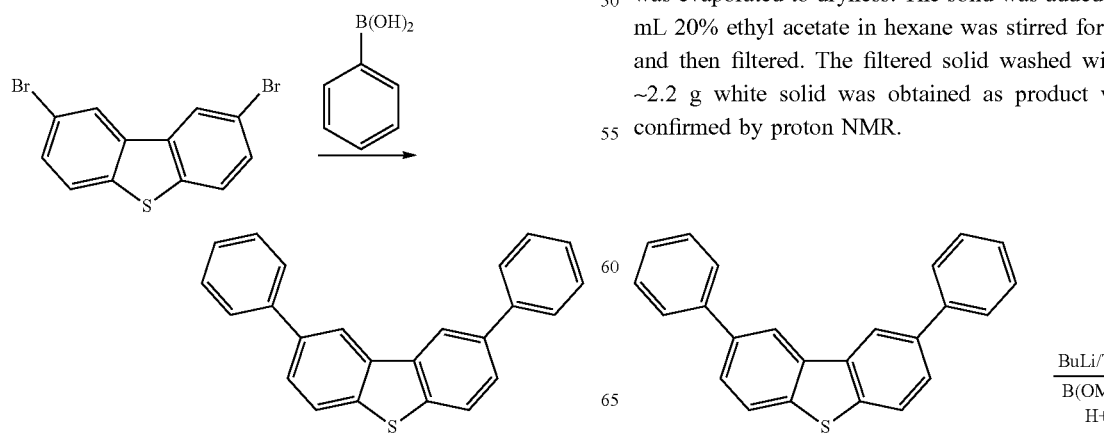

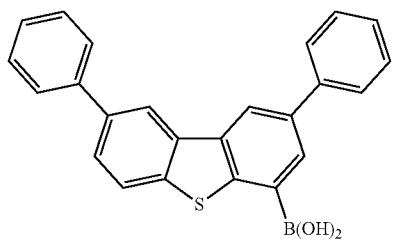

3. Synthesis of 2,4,8-triphenylbenzothiophene 5.5 g (14.5 mmol) 2,8-diphenyldibenzothiophene-4-boronic acid, 2.3 g (14.5 mmol) bromobenzene, 135 mg (0.15 mmol) Pd₂(dba)₃, 238 mg (0.58 mmol) S-phose, 9.2 g (43.2 mmol) K₃PO₄, 180 mL toluene and 20 mL water were charged in a 500 mL flask. The mixture was heated up to reflux under nitrogen for overnight. The reaction mixture was separated with separation funnel and the organic phase was purified by silica gel column chromatography using 20% ethyl acetate in hexane as elute. ~5.1 g 2, 4, 8-triphenylbenzothiophene white solid was obtained as product which was confirmed by proton NMR.

4. Synthesis of 2,4,8-tiphenyldibenzothiophene-6-boronic acid 5.0 g (12.13 mmol) 2,4,8-triphenylbenzothiophene was dissolved in ~100 mL anhydrous THF in a 250 mL three necked flask. To the mixture, ~19 mL (30.3 mmol) 1.6 M BuLi in hexane was added at −78° C. under nitrogen. The mixture was warned up to room temperature and kept stirring for 18 hours. The reaction mixture was cooled down to −78° C. again and 3.8 mL (34 mmol) trimethyl borate was added and kept mixture stirred for 4 hours at room temperature then added ~100 mL 1M HCl with stirring for 1.5 hour. The mixture was extracted by ethyl acetate and the organic phases were combined. The solvent was evaporated to dryness. The solid was added with ~150 mL 20% ethyl acetate in hexane. The mixture was stirred for few hours and then filtered. The filtered solid was washed with hexane 3 times. ~4.5 g white solid was obtained as product which was confirmed by proton NMR.

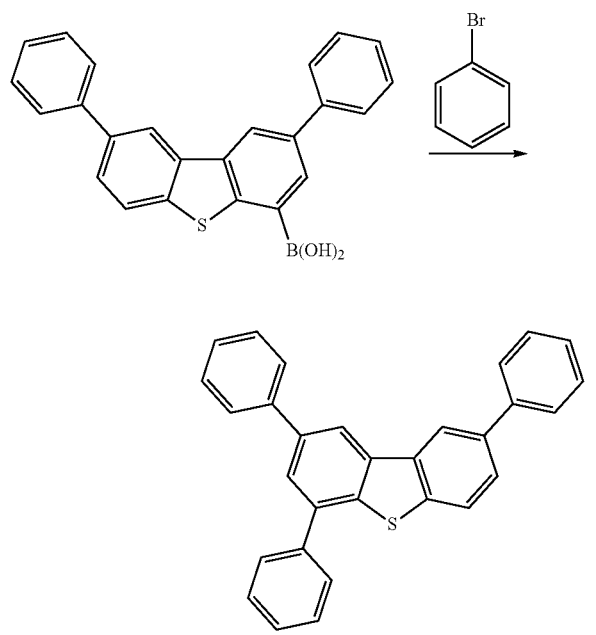

5. Synthesis of Compound 25S 3.5 g (7.67 mmol) 2,4,8-tiphenyldibenzothiophene-6-boronic acid, 3.2 g (6.98 mmol) 3-(triphenylen-2-yl)phenyl trifluoromethanesulfonate, 64 mg (0.077 mmol) Pd₂(dba)₃, 115 mg (0.30 mmol) S-phose, 4.5 g (22 mmol) K₃PO₄, 90 mL toluene and 10 mL water were charged in a 250 mL flask. The mixture was heated up to reflux under nitrogen for overnight. The reaction mixture was separated with separation funnel and the organic phase was purified by silica gel column chromatography using 25% dichloromethane in hexane as elute and recrystallization from toluene and hexane mixture. ~4.5 g (92%) white solid was obtained as product which was confirmed by proton NMR.

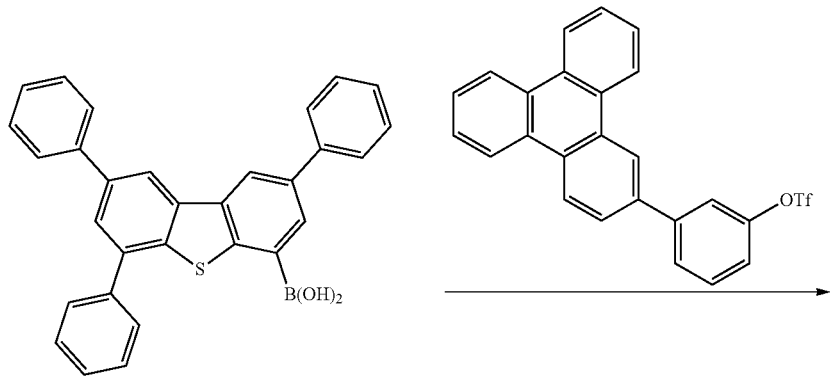

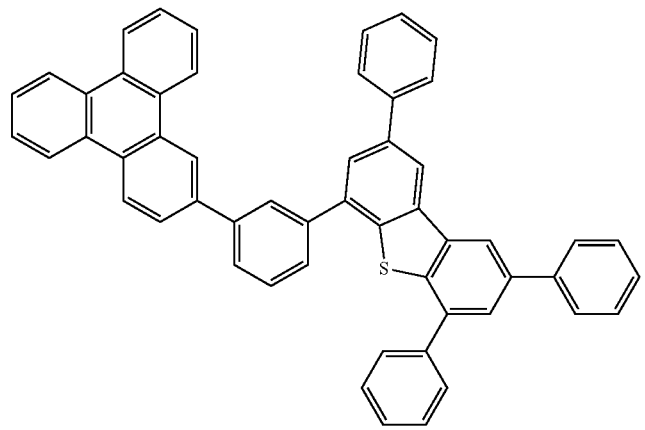

Compound 25S

Example 14

Compound 20

3.9 g (18.4 mmol) dibenzofurane-4-boronic acid, 7.0 g (15.4 mmol) 3-(triphenylen-2-yl)phenyl trifluoromethanesulfonate, 141 mg (0.154 mmol) Pd$_2$(dba)$_3$, 252 mg (0.46 mmol) S-phose, 9.8 g (46 mmol) K$_3$PO$_4$, 180 mL toluene and 20 mL water were charged in a 500 mL flask. The mixture was heated up to reflux under nitrogen for overnight. The reaction mixture was separated with separation funnel and the organic phase was purified by silica gel column chromatography using 20% dichloromethane in hexane as elute. ~6.2 g (87%) white solid was obtained as product which was confirmed by proton NMR.

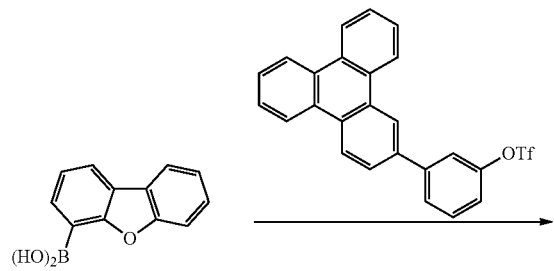

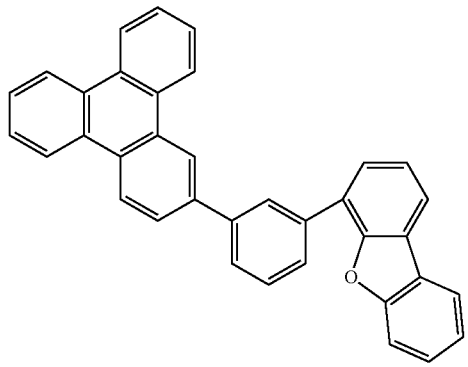

Compound 2O

Device Examples

All example devices were fabricated by high vacuum (<10$^{-7}$ Torr) thermal evaporation. The anode electrode is ~800 or 1200 Å of indium tin oxide (ITO). The cathode consisted of 10 Å of LiF followed by 1,000 Å of Al. All devices are encapsulated with a glass lid sealed with an epoxy resin in a nitrogen glove box (<1 ppm of $H_2O$ and $O_2$) immediately after fabrication, and a moisture getter was incorporated inside the package.

The organic stack of Device Examples 1-30 in Tables 1 and 2 consisted of sequentially, from the ITO surface, 100 Å of Compound A as the hole injection layer (HIL), 300 Å of 4,4'-bis[N-(1-naphthyl)-N-phenylamino]biphenyl (α-NPD) as the hole transporting layer (HTL), 300 Å of the invention compound doped with 10 or 15 wt % of an Ir phosphorescent compound as the emissive layer (EML), 50 or 100 Å of HPT or the invention compound as the ETL2 and 400 or 450 Å of $Alq_3$ (tris-8-hydroxyquinoline aluminum) as the ETL1.

Comparative Examples 1 and 2 were fabricated similarly to the Device Examples except that the CBP is used as the host.

The device structures and data are summarized in Tables 1 through 5. Table 1 shows device structure and Table 2 shows corresponding measured results for those devices, whereas each of Tables 3 through 5 show both the device structure and measured experimental results. As used herein, Compound A, Compound B, NPD and HPT, have the following structures:

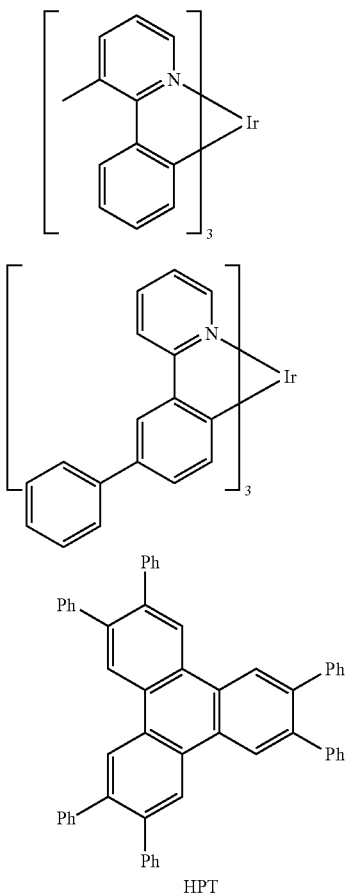

Compound A

Compound B

HPT

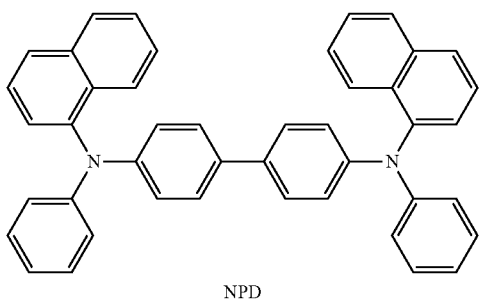

NPD

TABLE 1

| Device Example | Host | Dopant % | ETL2 (Å) | ETL1 (Å) | ITO thickness (nm) |
|---|---|---|---|---|---|
| Comparative 1 | CBP | B 10% | HPT (50) | Alq₃ (450) | 120 |
| Comparative 2 | CBP | A 10% | HPT (50) | Alq₃ (450) | 120 |
| 1 | 1S | A 10% | HPT (50) | Alq₃ (450) | 120 |
| 2 | 1S | A 10% | 1S (100) | Alq₃ (400) | 120 |
| 3 | 1S | A 15% | HPT (50) | Alq₃ (450) | 120 |
| 4 | 1S | A 15% | 1S (100) | Alq₃ (400) | 120 |
| 5 | 2S | A 10% | HPT (50) | Alq₃ (450) | 120 |
| 6 | 2S | A 10% | 2S (100) | Alq₃ (400) | 120 |
| 7 | 2S | A 15% | HPT (50) | Alq₃ (450) | 120 |
| 8 | 2S | A 15% | 2S (100) | Alq₃ (400) | 120 |
| 9 | 2S | B 10% | HPT (50) | Alq₃ (450) | 120 |
| 10 | 2S | B 10% | 2S (100) | Alq₃ (400) | 120 |
| 11 | 2S | B 15% | HPT (50) | Alq₃ (450) | 120 |
| 12 | 2S | B 15% | 2S (100) | Alq₃ (400) | 120 |
| 13 | 20S | A 10% | 20S (100) | Alq₃ (400) | 120 |
| 14 | 20S | A 10% | HPT (50) | Alq₃ (450) | 120 |
| 15 | 9S | A 10% | 20S (100) | Alq₃ (400) | 120 |
| 16 | 9S | A 10% | HPT (50) | Alq₃ (450) | 120 |
| 17 | 22S | A 10% | 22S (100) | Alq₃ (400) | 120 |
| 18 | 22S | A 10% | HPT (50) | Alq₃ (450) | 120 |
| 19 | 21S | A 10% | 21S (100) | Alq₃ (400) | 120 |
| 20 | 21S | A 10% | HPT (50) | Alq₃ (450) | 120 |
| 21 | 23S | A 15% | 23S (100) | Alq₃ (400) | 120 |
| 22 | 23S | A 15% | HPT (50) | Alq₃ (450) | 120 |
| 23 | 23S | A 10% | 23S (100) | Alq₃ (400) | 120 |
| 24 | 23S | A 10% | HPT (50) | Alq₃ (450) | 120 |
| 25 | 24S | A 10% | 24S (100) | Alq₃ (400) | 120 |
| 26 | 24S | A 10% | HPT (50) | Alq₃ (450) | 120 |
| 27 | 5S | A 10% | 5S (100) | Alq₃ (400) | 120 |
| 28 | 5S | A 10% | HPT (50) | Alq₃ (450) | 120 |
| 29 | 2O | A 10% | 2O (100) | Alq₃ (400) | 120 |
| 30 | 2O | A 10% | HPT (50) | Alq₃ (450) | 120 |

TABLE 2

| Device Example | CIE X | CIE Y | Emission max (nm) | FWHM (nm) | At L = 1000 cd/m² | | | | At J = 40 mA/cm² | |
|---|---|---|---|---|---|---|---|---|---|---|
| | | | | | V (V) | LE (cd/A) | EQE (%) | PE (lm/W) | L₀ (cd/m²) | LT₈₀% (hr) |
| Comparative 1 | 0.331 | 0.627 | 521 | 67 | 6.1 | 61.0 | 17 | 31.4 | 16,935 | 87 |
| Comparative 2 | 0.346 | 0.613 | 522 | 75 | 6.2 | 57.0 | 16 | 28.9 | 13,304 | 105 |
| 1 | 0.347 | 0.610 | 526 | 76 | 5.9 | 60.6 | 17 | 32.3 | 14,083 | 270 |
| 2 | 0.345 | 0.612 | 526 | 75 | 6.4 | 54.9 | 15 | 26.9 | 14,028 | 310 |
| 3 | 0.348 | 0.609 | 526 | 76 | 5.9 | 60.1 | 17 | 32.0 | 14,092 | 288 |
| 4 | 0.346 | 0.611 | 526 | 75 | 6.4 | 54.0 | 14.8 | 26.5 | 13,946 | 306 |
| 5 | 0.347 | 0.612 | 526 | 75 | 5.5 | 67.1 | 18 | 38.3 | 16,615 | 244 |
| 6 | 0.346 | 0.612 | 527 | 74 | 6.2 | 59.6 | 16 | 30.2 | 16,160 | 300 |
| 7 | 0.352 | 0.608 | 527 | 77 | 5.6 | 62.5 | 17 | 35.0 | 15,726 | 224 |
| 8 | 0.350 | 0.609 | 526 | 76 | 6.2 | 57.1 | 16 | 28.9 | 15,716 | 260 |
| 9 | 0.341 | 0.619 | 525 | 69 | 6.2 | 59.9 | 16.2 | 30.3 | 14,641 | 380 |
| 10 | 0.343 | 0.618 | 525 | 72 | 6.8 | 50.2 | 13.6 | 23.2 | 14,069 | 450 |
| 11 | 0.343 | 0.620 | 527 | 69 | 5.9 | 54.3 | 14.6 | 28.9 | 17,088 | 194 |
| 12 | 0.341 | 0.620 | 527 | 68 | 6.5 | 40.5 | 10.9 | 19.6 | 13,744 | 620 |
| 13 | 0.356 | 0.607 | 528 | 76 | 6.4 | 60.9 | 16.8 | 29.8 | 15,974 | 150 |
| 14 | 0.356 | 0.607 | 528 | 76 | 5.7 | 66.6 | 18.4 | 38.1 | 15,414 | 134 |
| 15 | 0.366 | 0.600 | 528 | 75 | 6.0 | 52 | 14.2 | 25 | 15,950 | 60 |
| 16 | 0.357 | 0.608 | 528 | 75 | 6.0 | 60 | 16.4 | 31.2 | 17,100 | 70 |
| 17 | 0.375 | 0.587 | 532 | 78 | 8 | 29.3 | 8.2 | 11.5 | 8,755 | 91 |
| 18 | 0.374 | 0.590 | 532 | 76 | 7.5 | 39.2 | 11 | 16.4 | 10,865 | 82 |
| 19 | 0.367 | 0.597 | 532 | 82 | 8.5 | 35.4 | 9.8 | 13.1 | 10,058 | 338 |
| 20 | 0.364 | 0.600 | 532 | 82 | 7.9 | 44.5 | 12.3 | 17.7 | 11,682 | 240 |
| 21 | 0.365 | 0.601 | 528 | 76 | 6.9 | 49.5 | 13.7 | 22.5 | 14,135 | 620 |
| 22 | 0.363 | 0.603 | 528 | 76 | 6.2 | 56.5 | 15.7 | 28.6 | 15,067 | 457 |
| 23 | 0.362 | 0.602 | 529 | 77 | 7.2 | 52.4 | 14.6 | 22.9 | 14,186 | 378 |
| 24 | 0.364 | 0.601 | 529 | 77 | 6.6 | 55.1 | 15.4 | 26.2 | 13,810 | 343 |
| 25 | 0.363 | 0.603 | 530 | 78 | 6.8 | 52.3 | 14.5 | 29.8 | 14,994 | 175 |
| 26 | 0.363 | 0.602 | 530 | 78 | 6.3 | 51.9 | 14.4 | 36.7 | 14,061 | 150 |
| 27 | 0.385 | 0.588 | 538 | 86 | 7.4 | 30.7 | 8.6 | 13.0 | 10,211 | 1.3 |
| 28 | 0.382 | 0.590 | 538 | 86 | 6.8 | 36.4 | 10.2 | 16.8 | 11,305 | 2.0 |
| 29 | 0.352 | 0.609 | 528 | 79 | 6.6 | 56.8 | 15.7 | 27.0 | 15,207 | 305 |
| 30 | 0.355 | 0.607 | 528 | 78 | 6 | 63.3 | 17.4 | 33.1 | 15,219 | 240 |

From Device Examples 1-30, it can be seen that Compounds 1S, 2S, 20S, 9S, 23S, 24S and 2O as hosts in green phosphorescent OLEDs give high device efficiency (LE>40 cd/A at 1000 cd/m²), indicating the triphenylene and benzothiophene combinations, either directly linked or m-phenylene-linked have triplet energy high enough for efficient green electrophosphorescence.

The high stability of devices incorporating Compounds 1S, 2S, 21S, 23S and 2O as the host is notable. Device Example 1 and Comparative Example 2 are only different in the host. Device Example 1 uses Compound 1 as the host whereas Comparative Example 2 uses the commonly used host CBP. The lifetime, $T_{80}$% (defined as the time required for the initial luminance, $L_0$, to decay to 80% of its value, at a constant current density of 40 mA/cm² at room temperature) are 270 hours and 105 hours respectively, with Device Example 1 having a slightly higher $L_0$. This translates to almost a 3 fold improvement in the device stability. Similarly, Device Example 5 using Compound 2S as the host, is at least 2.5 times more stable than Comparative Example 2. Device Example 9 using Compound 2S as the host, is at least 3 times more stable than Comparative Example 1 with CBP as the host. It is also notable that the compounds may function very well as an enhancement layer material (ETL2). Device Example 10 and Device Example 9 both have Compound 2S as the host, but Compound 2 and HPT as the enhancement layer respectively. Device Example 10 and Device Example 9 have $T_{0.8}$ of 450 and 380 hours respectively, indicating the good performance of Compound 2S as the enhancement layer material. Device Example 21 has $T_{0.8}$ of 620 hours which is significantly higher than the lifetime of Comparative Example 1 or 2 device with CBP.

The data suggest that triphenylene containing benzothiophenes, particularly triphenylene containing dibenzothiophenes, are excellent host and enhancement layer materials for phosphorescent OLEDs, providing as least the same efficiency and multiple times of improvement in stability compared to the commonly used CBP as the host. More conjugated versions of triphenylene containing benzothiophenes, for example triphenylene and benzothiophene units linked via p-phenylene (such as 4,4'-biphenyl) may be very suitable for lower energy (yellow to red) phosphorescent OLEDs.

Table 3 shows device structures and measured experimental results for some devices having an emissive layer with an interface between a first organic layer and a second organic layer, where the host and the dopant, i.e., the non-emissive material is the same material in both layers and the phosphorescent material is the same material in both layers, but the concentrations are different. All of the devices in Table 3 had a 100 Å hole injection layer of Compound A, a 100 Å enhancement layer (ETL2) of different materials depending on the specific device, a 400 Å electron transport layer (ETL1), and an LiF/Al cathode. The emissive layer included a first organic layer and a second organic layer with an interface between them, where the first organic layer was 300 Å of a non-emissive material (the "host" in Table 3) at a concentration of 70 wt % and a phosphorescent material (the "dopant" of Table 3) at a concentration of 30 wt %, and the second organic layer was 300 Å of the same non-emissive material (the "host" in Table 3) but at a concentration of 90 wt % and the same phosphorescent material (the "dopant" of Table 3) but at a concentration of 10 wt %. The specific host and dopant for each device are identified in Table 3. Thus, the general device structure for the devices of Table 3 was: ITO (1200 Å)/Compound A (100 Å)/host (70 wt %):dopant (30 wt %) (300 Å)/host (90 wt %):dopant (10 wt %) (300 Å)/ETL2 (100 Å)/Alq$_3$ (400 Å)/LiF/Al.

the stabilization of the oxidized/reduced states of the molecule by the i-conjugation provided by the benzothiophene and triphenylene units.

Table 4 and Table 5 show device structures and measured experimental results for devices having an emissive layer containing triphenylene and benzo-fused thiophene attached to a central pyridine.

All of the devices in Table 4 had a 100 Å hole injection layer of Compound A, a 300 Å hole transport layer of NPD,

TABLE 3

| | | | | CIE | | | | At 1,000 nits | | | At 40 mA/cm$^2$ | |
| --- | --- | --- | --- | --- | --- | --- | --- | --- | --- | --- | --- | --- |
| | | | | | | V | L.E. | E.Q.E. | P.E. | Lo | LT80% |
| Example | Host | Dopant | ETL2 | X | Y | (V) | [cd/A] | [%] | [lm/W] | [nits] | [h] |
| A | Cmpd. 2S | A | Cmpd. 2S | 0.36 | 0.61 | 6.4 | 57.5 | 15.9 | 28.2 | 17,225 | 1060 |
| B | Cmpd. 2S | A | HPT | 0.36 | 0.61 | 5.8 | 60.4 | 16.6 | 32.7 | 16,732 | 1000 |
| C | Cmpd. 2S | B | Cmpd. 2S | 0.34 | 0.62 | 8.4 | 46.4 | 12.5 | 17.3 | 15,184 | 2100 |
| D | Cmpd. 2S | B | HPT | 0.35 | 0.62 | 7.8 | 54.7 | 14.8 | 22.0 | 15,04 | 1350 |

The devices in Table 3, using Compound 2S as the host and Compound 2S or HPT as the enhancement layer material show high efficiency (>46 cd/A at 1000 cd/m$^2$). Even more notable are the stabilities of LT$_{80\%}$ of 1000 hours (Device Examples A, B and D) or even 2000 hours (Device Example C), rendering these devices among the most long-lived green phosphorescent OLEDs to date.

The good performance and high stability of the devices with triphenylene-benzothiophene hybrids is believed to be a result of the good charge balance provided by the triphenylene and benzothiophene charge transporting units, and a 300 Å emissive layer with Compound 21S as the host and Compound A as the dopant, a blocking layer (BL) having materials and thicknesses identified in Table 4, an electron transport layer (ETL) of Alq having a thickness identified in Table 4, and a LiF/Al cathode. In particular, the BL thickness and the ETL thickness have a sum total of 500 Å. The emissive layer was a single layer including the host and dopant. The specific percentage of dopant for each device is identified in Table 4. Thus, the general device structure for Table 4 was: ITO (1200 Å)/Compound A (100 Å)/NPD (300 Å)/Compound 21S:Compound A x % (300 Å)/BL/Alq (500 Å−BL)/LiF (10)/Al (1000).

TABLE 4

| | | Dopant | | ETL | CIE | | V | L.E. | EQE | P.E. | At 1,000 nits | At 40 mA/cm$^2$ |
| --- | --- | --- | --- | --- | --- | --- | --- | --- | --- | --- | --- | --- |
| | | | | | | | | | | | Lo | RT |
| Example | Host | x % | BL | (Å) | X | Y | (V) | [Cd/A] | [%] | [lm/W] | [nits] | 80% |
| E | 21S | A, 10% | 21S 100 Å | Alq 400 | 0.367 | 0.597 | 8.5 | 35.4 | 9.8 | 13.1 | 10,058 | 338 |
| F | 21S | A, 15% | 21S 100 Å | Alq 400 | 0.370 | 0.594 | 8.1 | 34 | 9.5 | 13.2 | 10,189 | 335 |
| G | 21S | A, 10% | HPT 50 Å | Alq 450 | 0.364 | 0.600 | 7.9 | 44.5 | 12.3 | 17.7 | 11,682 | 240 |
| H | 21S | A, 15% | HPT 50 Å | Alq 450 | 0.369 | 0.597 | 7.5 | 44.3 | 12.3 | 18.5 | 12,377 | 235 |

All of the devices of Table 5 had a 100 Å hole injection layer of Compound A, a 300 Å hole transport layer having materials identified in Table 5, a 300 Å emissive layer with Compound 22S as the host and Compound A as the dopant, a blocking layer (BL) having materials and thicknesses identified in Table 5, an electron transport layer having a thickness that is 500 Å minus the thickness (Å) of the blocking layer (BL), and a LiF/Al cathode. In particular, the BL thickness and the ETL thickness have a sum total of 500 Å. The emissive layer was a single layer including the host and dopant. The specific percentages for each device is identified in Table 5. Thus, the general device structure for Table 5 was: ITO (1200 Å)/Compound A 100 (Å)/HTL (300 Å)/Compound 22S:Compound A x % (300 Å)/BL/Alq (500 Å—BL)/LiF (10)/Al (1000).

TABLE 5

| Example | HTL, 300 Å | Host | Dopant x % | BL (Å) | ETL (Å) | CIE X | CIE Y | V (V) | L.E. [cd/A] | E.Q.E. [%] | P.E. [lm/W] | Lo [nits] | RT 80% [hr]* |
|---|---|---|---|---|---|---|---|---|---|---|---|---|---|
| I | NPD 300 Å | 22S | A 10% | 22S 100 | Alq 400 | 0.375 | 0.587 | 8 | 29.3 | 8.2 | 11.5 | 8,755 | 91 |
| J | NPD 300 Å | 22S | A 10% | HPT 50 | Alq 450 | 0.374 | 0.590 | 7.5 | 39.2 | 11 | 16.4 | 10,865 | 82 |
| K | NPD 300 Å | 22S | A 15% | 22S 100 | Alq 400 | 0.374 | 0.590 | 7.9 | 31.2 | 8.7 | 12.4 | 9,222 | 120 |
| L | NPD 300 Å | 22S | A 15% | HPT 50 | Alq 450 | 0.373 | 0.594 | 7.4 | 42.4 | 11.7 | 18.0 | 11,522 | 110 |
| M | 22S:Å 30% | 22S | A 10% | 22S 100 | Alq 400 | 0.398 | 0.579 | 9.5 | 16.4 | 4.7 | 5.4 | 5,959 | >600 |
| N | 22S:Å 30% | 22S | A 10% | HPT 50 | Alq 450 | 0.393 | 0.583 | 9.3 | 20.2 | 5.8 | 6.8 | 6,863 | >600 |

*extrapolated data

It is understood that the various embodiments described herein are by way of example only, and are not intended to limit the scope of the invention. For example, many of the materials and structures described herein may be substituted with other materials and structures without deviating from the spirit of the invention. The present invention as claimed may therefore includes variations from the particular examples and preferred embodiments described herein, as will be apparent to one of skill in the art. Particularly, the triphenylene containing group may be attached to any position of benzothiophene or benzofuran. It is understood that various theories as to why the invention works are not intended to be limiting.

The invention claimed is:

1. A compound represented by a structure selected from the group consisting of:

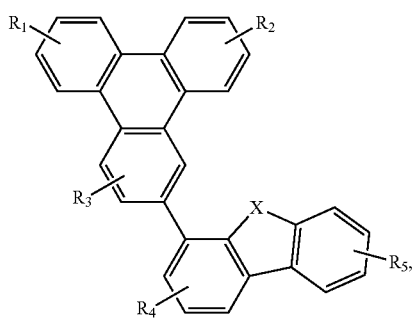

Compound 1G

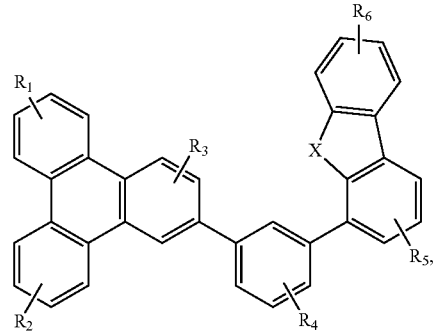

Compound 2G

-continued

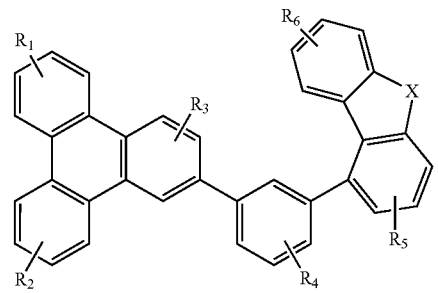

Compound 3G

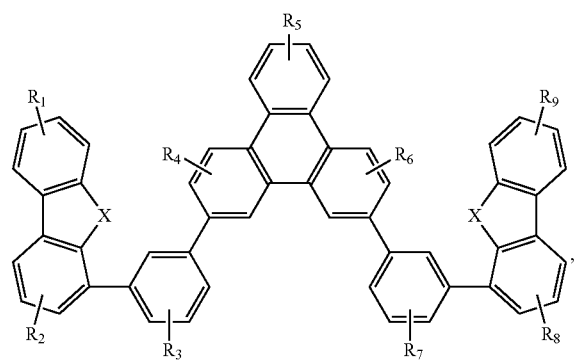

Compound 4G

-continued
Compound 5G
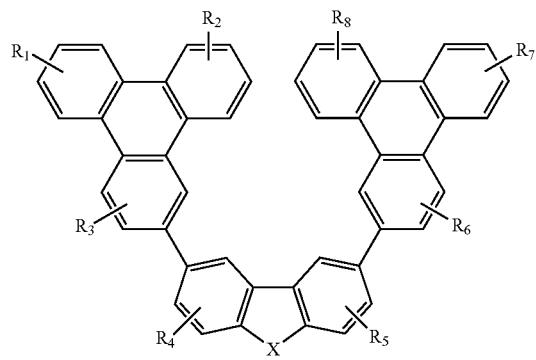
Compound 6G
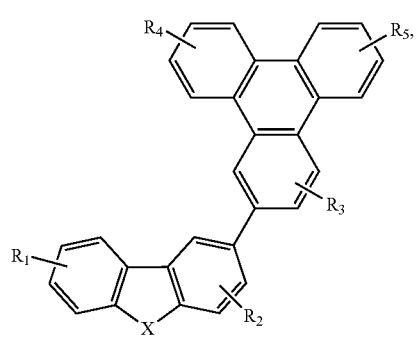
Compound 7G
Compound 8G
Compound 9G
-continued
Compound 10G
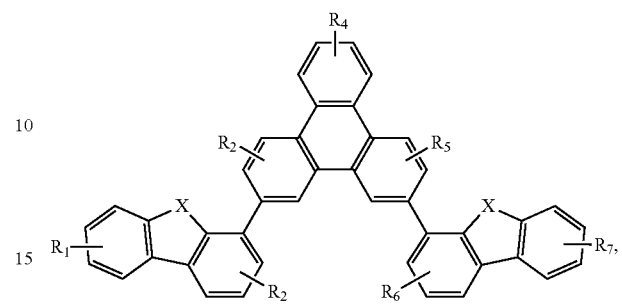
Compound 11G
Compound 12G
Compound 13G
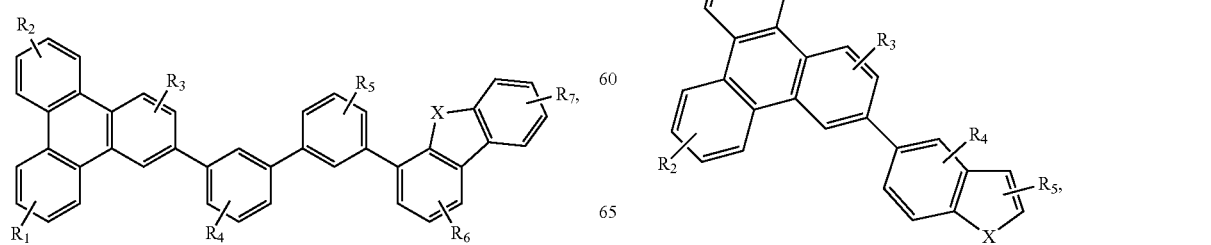

Compound 14G
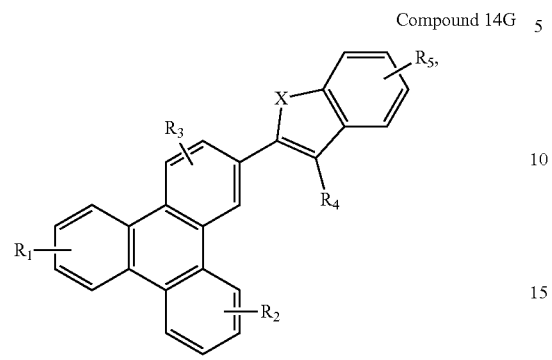
Compound 15G
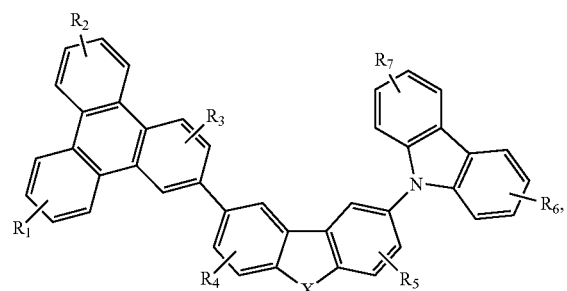
Compound 16G
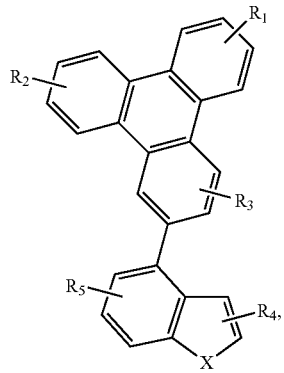
Compound 17G
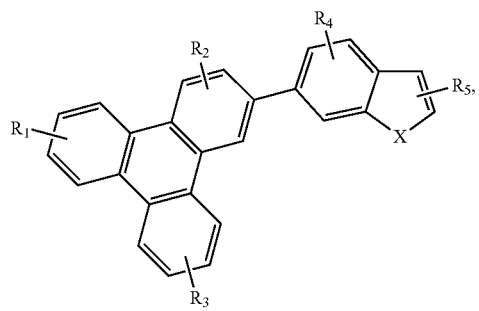
Compound 18G
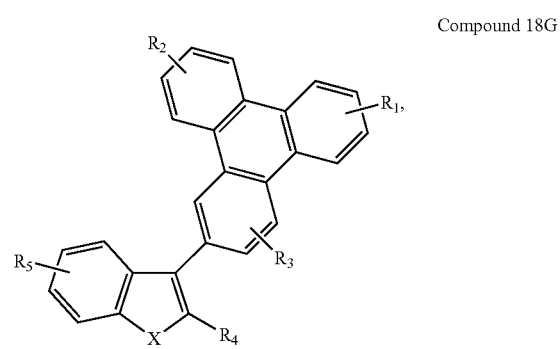
Compound 19G
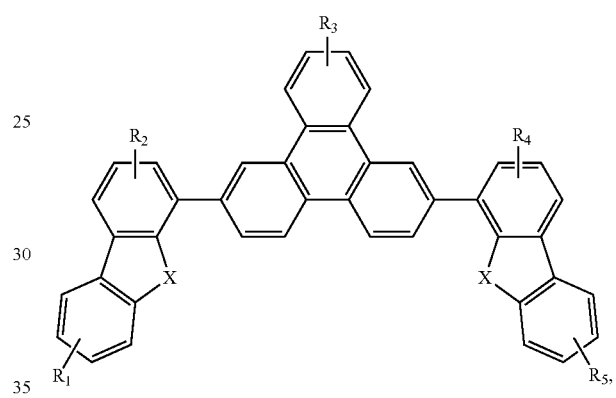
Compound 20G
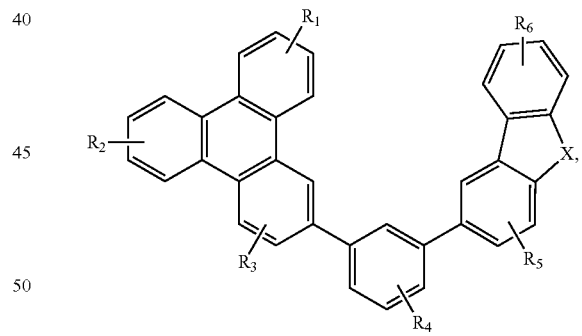
Compound 21G
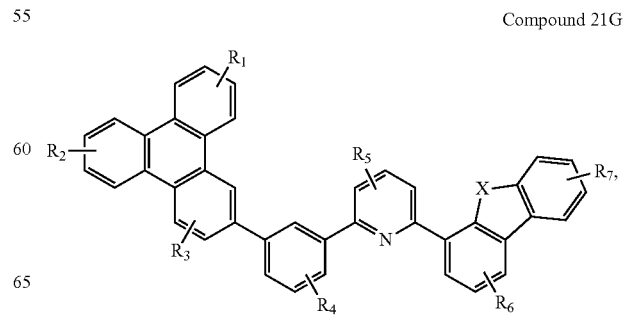

Compound 22G
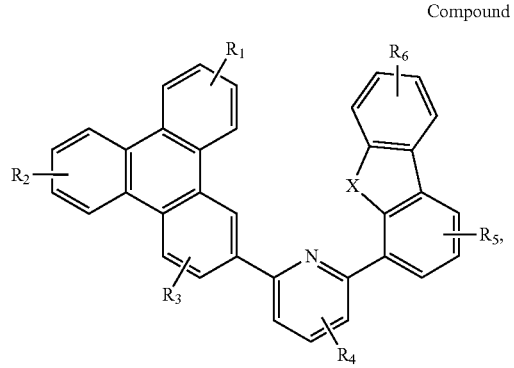
Compound 26G
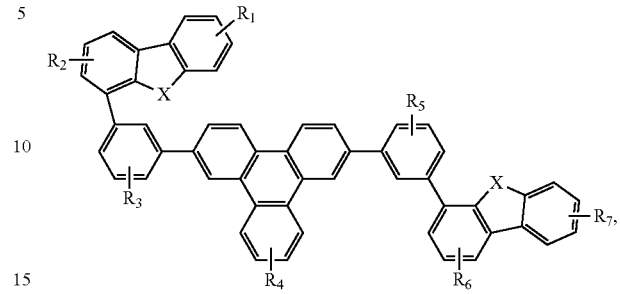
Compound 23G
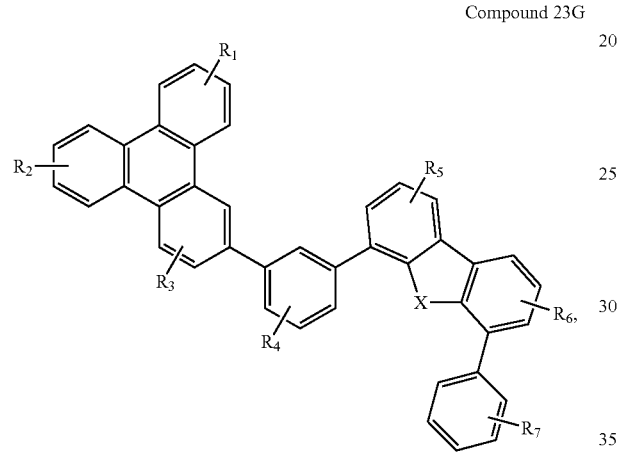
Compound 27G
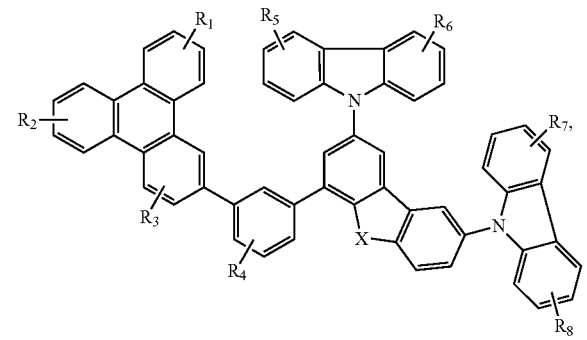
Compound 24G
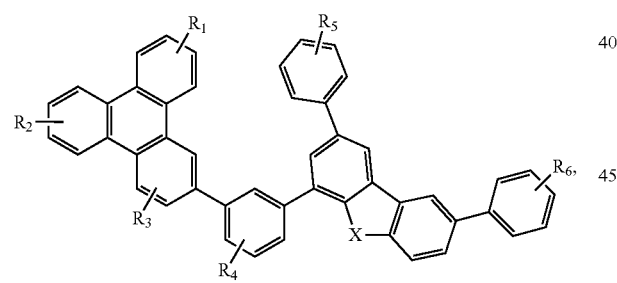
Compound 28 G
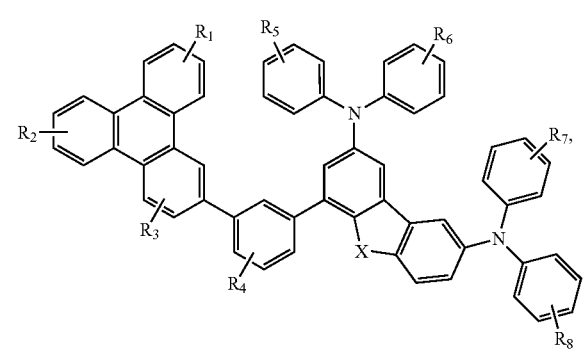
Compound 25G
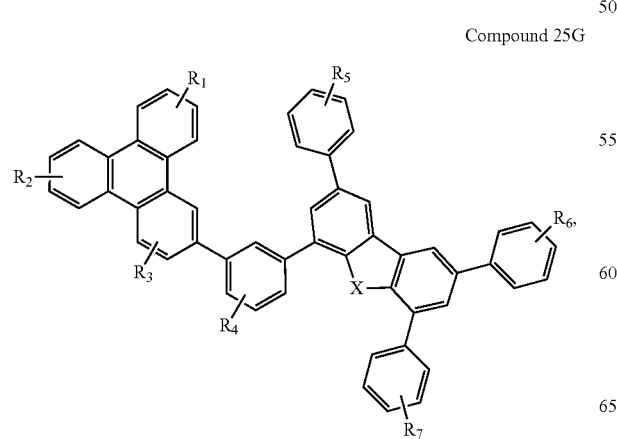
Compound 29G
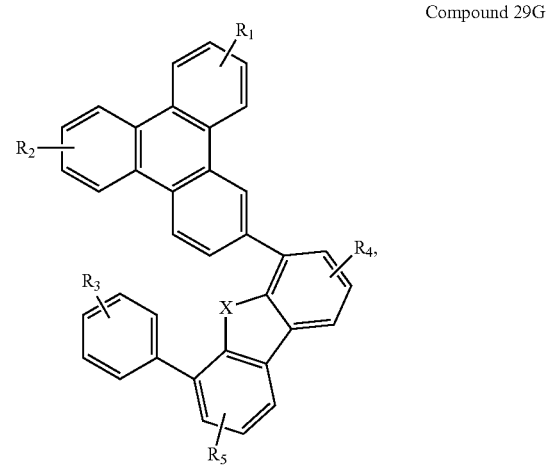

-continued
Compound 30G
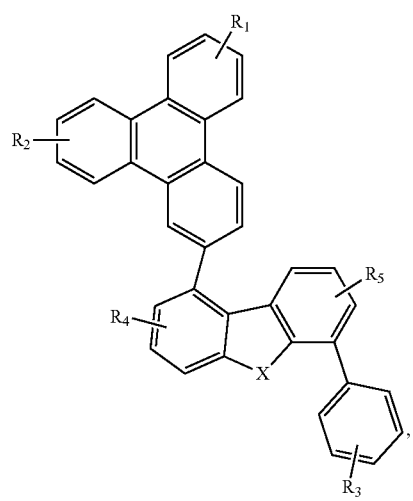
Compound 31G
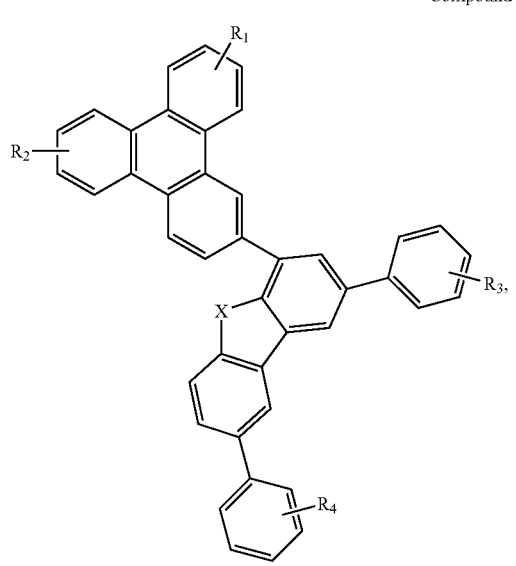
Compound 32G
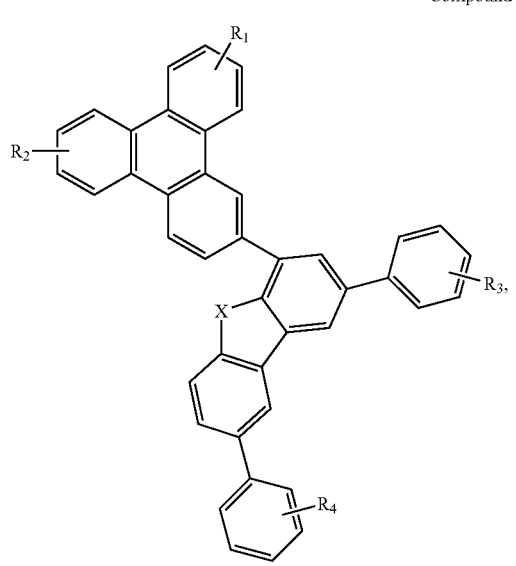
-continued
Compound 33G
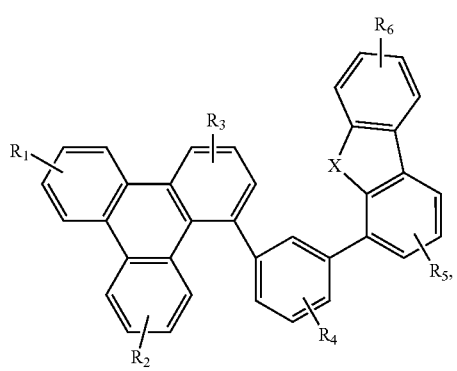
Compound 34G
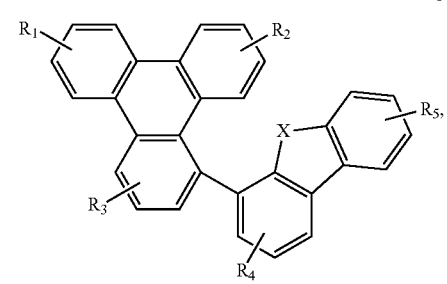
Compound 35G
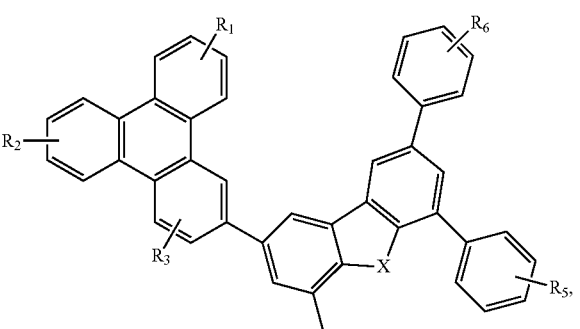
Compound 36G
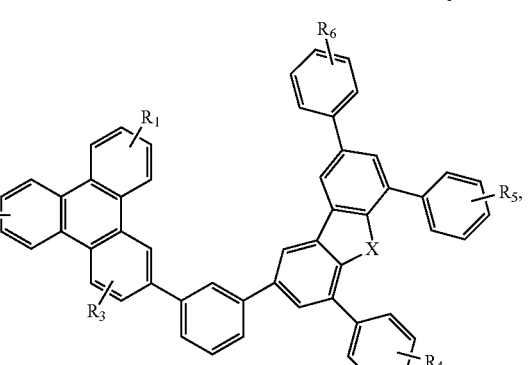

Compound 37G
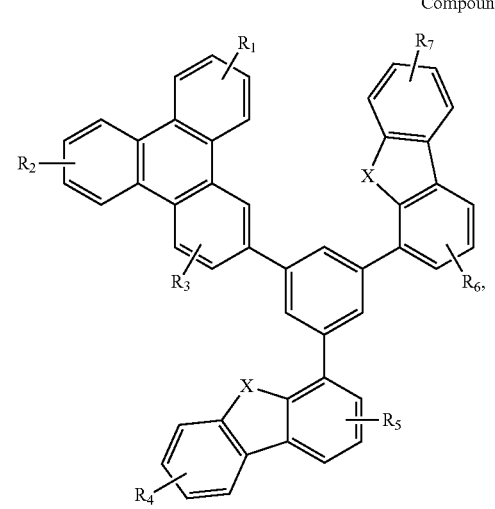
Compound 38G
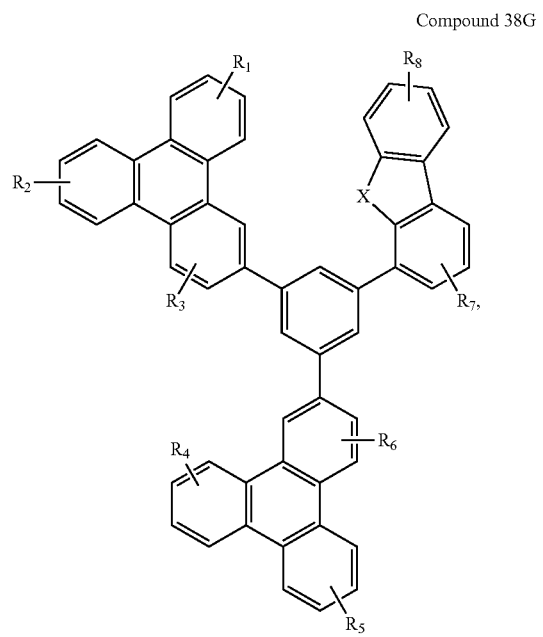
Compound 39G
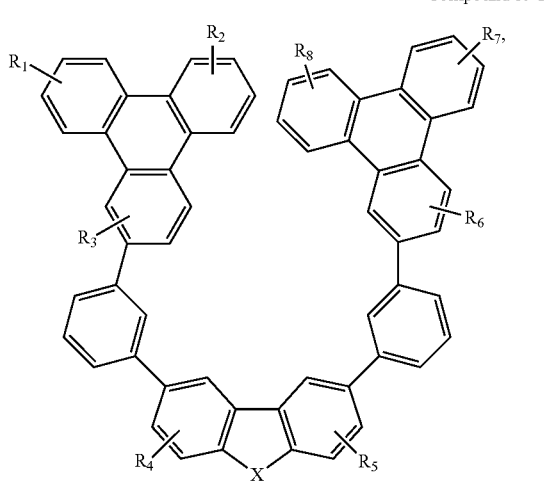
Compound 40G
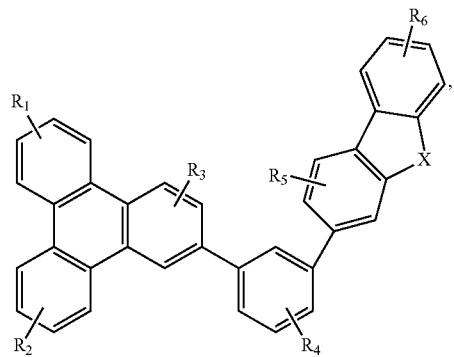
Compound 41G
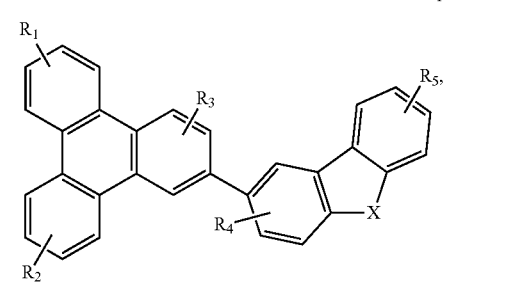
Compound 42G
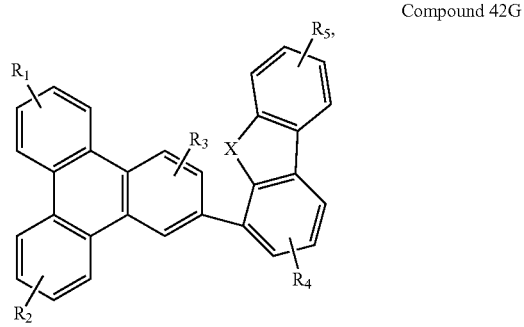
Compound 43 G
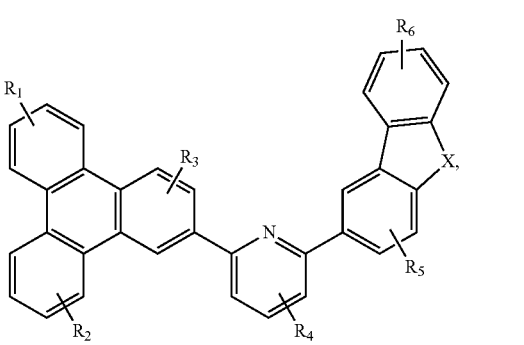
Compound 44 G
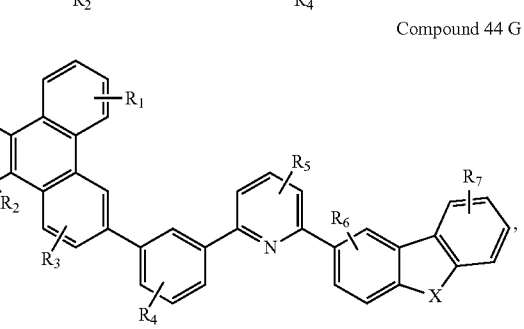

Compound 45G

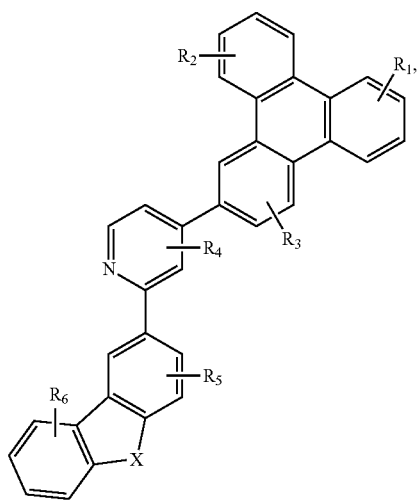

Compound 46 G

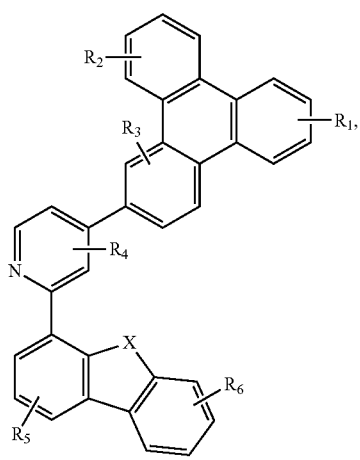

Compound 47 G

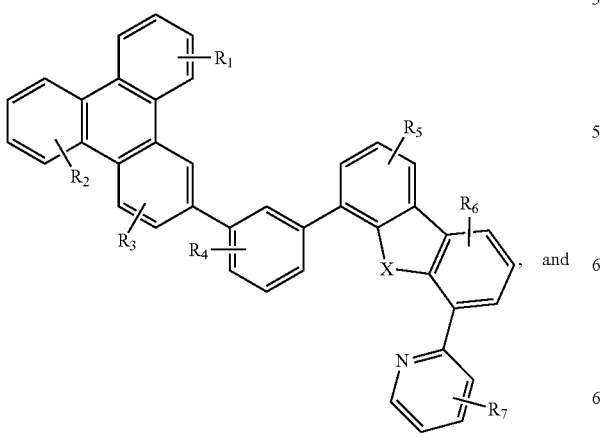, and

Compound 48 G

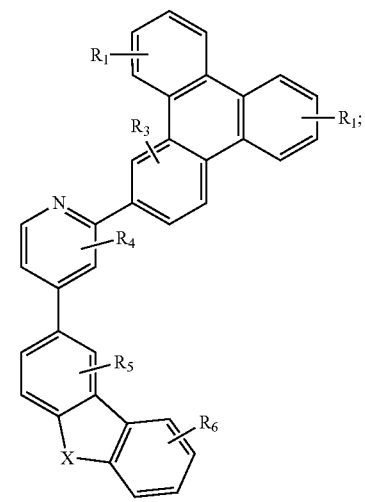;

wherein X is S or O;
wherein $R_1$ to $R_9$ are independently selected from the group consisting of hydrogen, alkyl, alkoxy, amino, alkenyl, alkynyl, arylalkyl, aryl, and heteroaryl; and
wherein each of $R_1$ to $R_9$ may represent mono substitutions up to the maximum possible substitutions, or no substitutions.

2. The compound of claim 1, wherein X is O.

3. The compound of claim 1, wherein X is S.

4. The compound of claim 1, wherein each of $R_1$ to $R_9$ is aryl, heteroaryl, or no substitution.

5. The compound of claim 1, wherein at least one $R_1$, $R_2$, $R_3$, or $R_4$ is other than hydrogen.

6. The compound of claim 1,
wherein at least one $R_5$ is other than hydrogen, and
wherein the structure is selected from the group consisting of Compound 1G to Compound 30G and Compound 32G to Compound 48G.

7. The compound of claim 1,
wherein at least one $R_6$ is other than hydrogen, and
wherein the compound has a structure is selected from the group consisting of Compound 2G, Compound 3G, Compound 4G, Compound 5G, Compound 9G, Compound 10G, Compound 11G, Compound 16G, Compound 21G, Compound 22G, Compound 23G, Compound 24G, Compound 25G, Compound 26G, Compound 27G, Compound 28G, Compound 35G, Compound 36G, Compound 37G, Compound 38G, Compound 39G, Compound 40G, Compound 43G, Compound 44G, Compound 45G, Compound 46G, Compound 47G, and, Compound 48G.

8. The compound of claim 1,
wherein at least one $R_6$ is other than hydrogen, and
wherein the compound has a structure is selected from the group consisting of Compound 2G, Compound 3G, Compound 4G, Compound 50, Compound 9G, Compound 10G, Compound 11G, Compound 16G, Compound 21G, Compound 22G, Compound 23G, Compound 24G, Compound 25G, Compound 26G, Compound 27G, Compound 28G, Compound 35G, Compound 36G, Compound 37G, Compound 38G, Compound 39G, Compound 40G, Compound 43G, Compound 44G, Compound 45G, Compound 46G, Compound 47G, and Compound 48G.

9. The compound of claim 1,
wherein at least one $R_7$ is other than hydrogen, and
wherein the compound has a structure is selected from the group consisting of Compound 4G, Compound 5G, Compound 9G, Compound 10G, Compound 11G, Compound 16G, 21G, Compound 23G, Compound 25G, Compound 26G, Compound 27G, Compound 28G, Compound 37G, Compound 38G, Compound 39G, Compound 44G, and Compound 47G.

10. The compound of claim 1,
wherein at least one $R_8$ is other than hydrogen, and
wherein the compound has a structure is selected from the group consisting of Compound 4G, Compound 5G, Compound 27G, Compound 28G, Compound 38G, and Compound 39G.

11. The compound of claim 1,
wherein at least one $R_9$ is other than hydrogen, and the compound has a structure of Compound 4G.

12. The compound of claim 1, having a structure selected from the group consisting of:

Compound 1

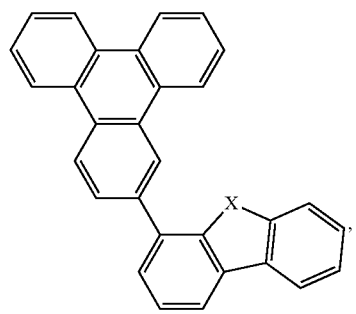

Compound 2

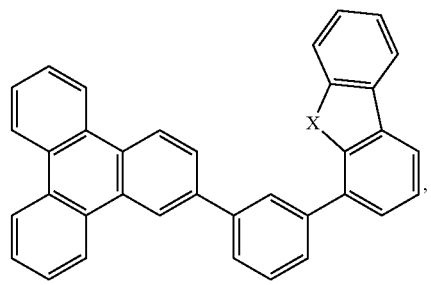

Compound 3

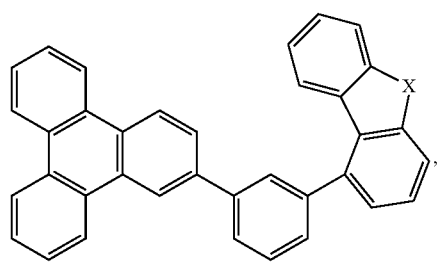

Compound 4

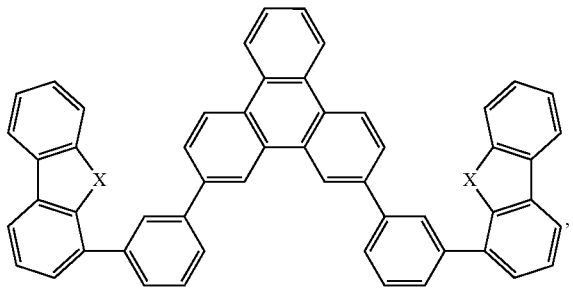

Compound 5

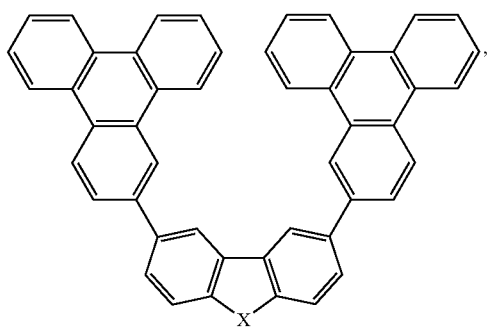

Compound 6

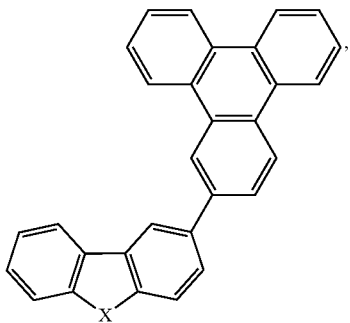

Compound 7

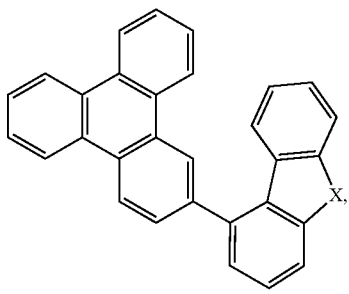

Compound 8

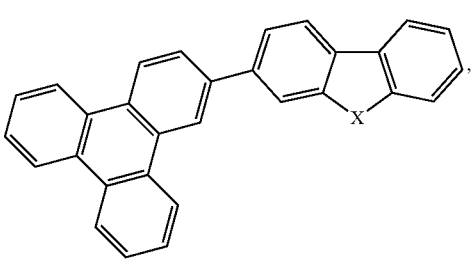

Compound 9
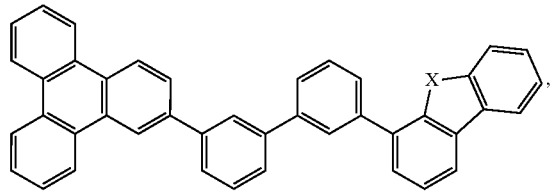
Compound 10
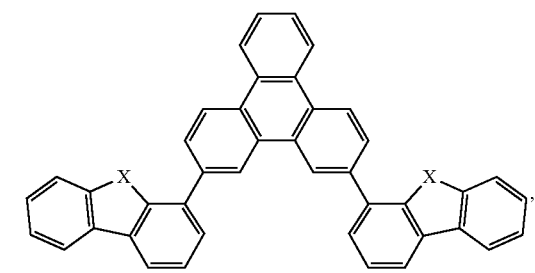
Compound 11
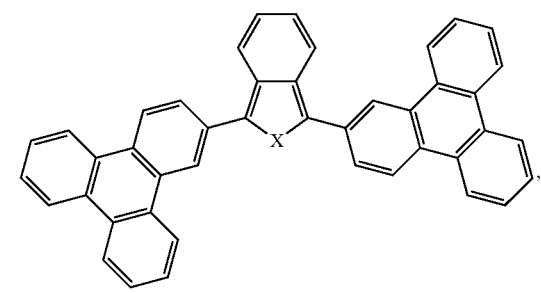
Compound 12
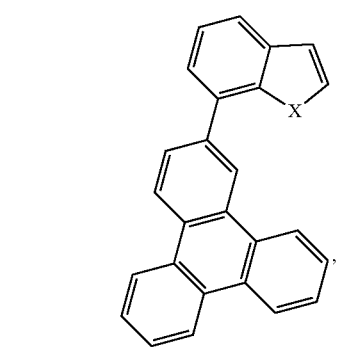
Compound 13
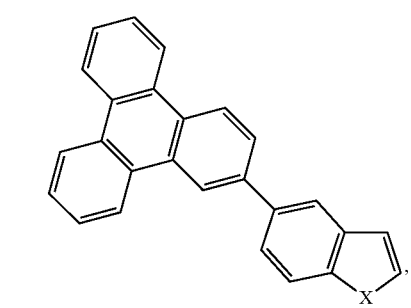
Compound 14
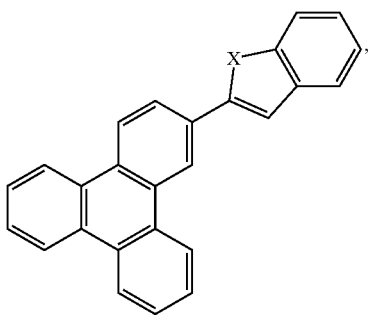
Compound 15
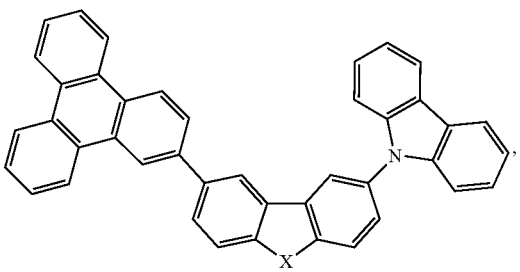
Compound 16
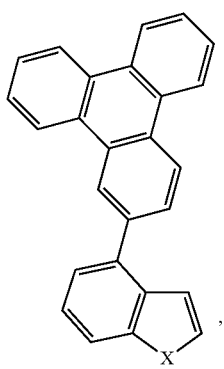
Compound 17
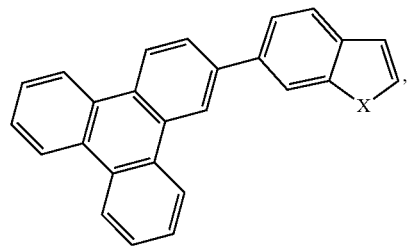
Compound 18
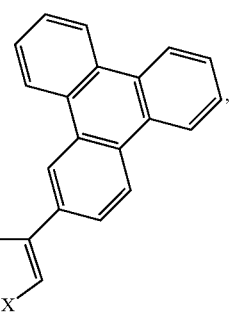

Compound 19
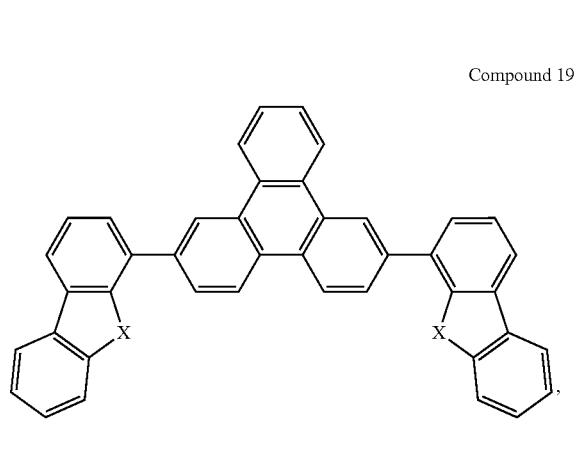
Compound 20
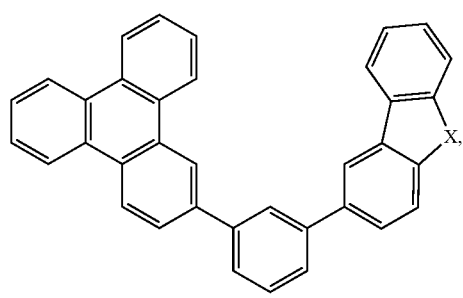
Compound 21
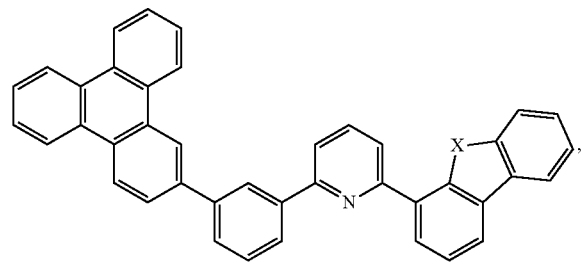
Compound 22
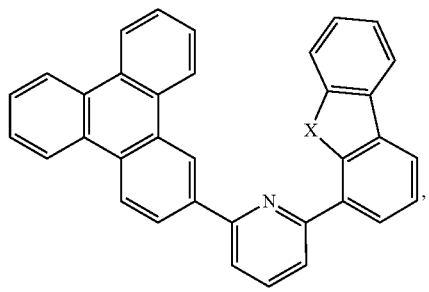
Compound 23
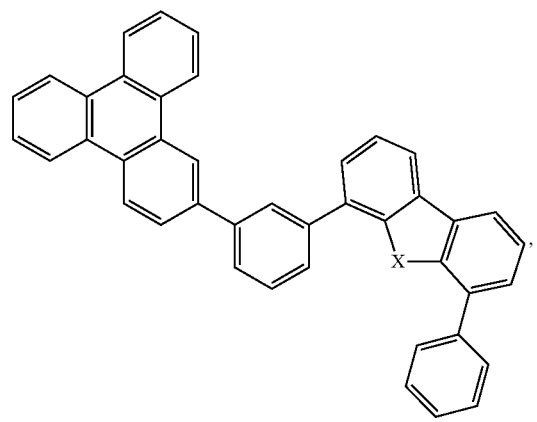
Compound 24
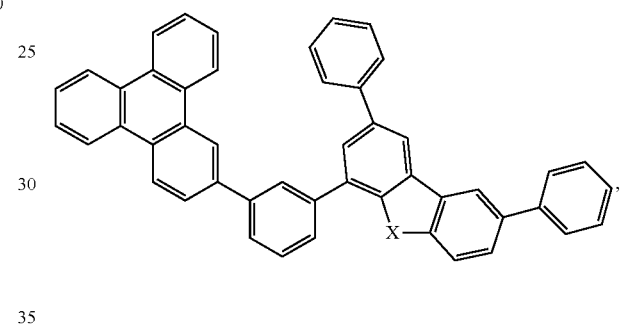
Compound 25
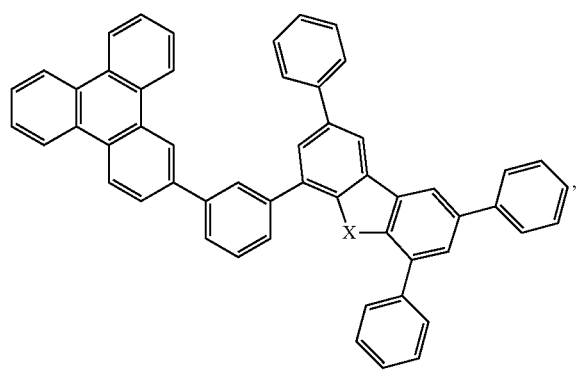
Compound 26
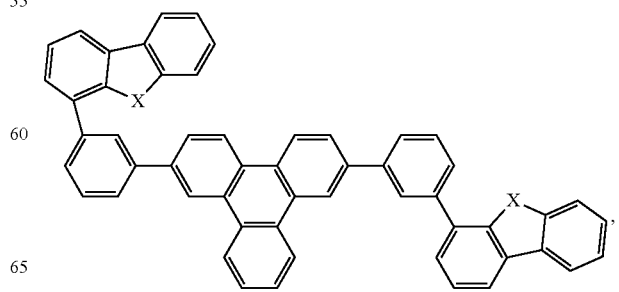

101
-continued
Compound 27
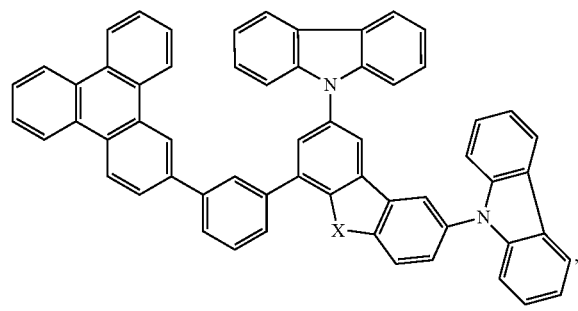
Compound 28
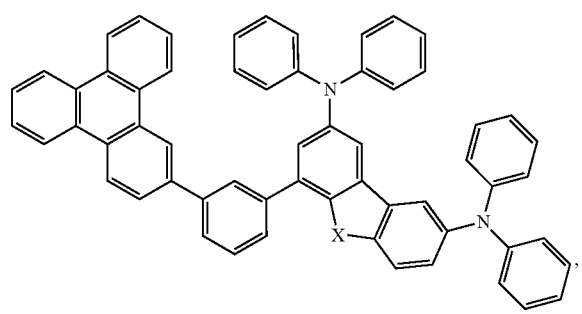
Compound 29
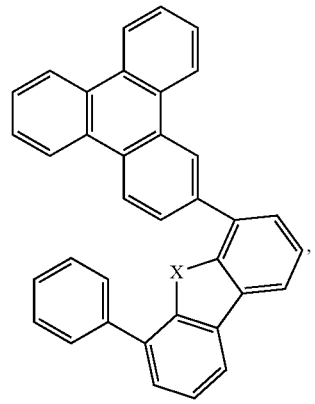
Compound 30
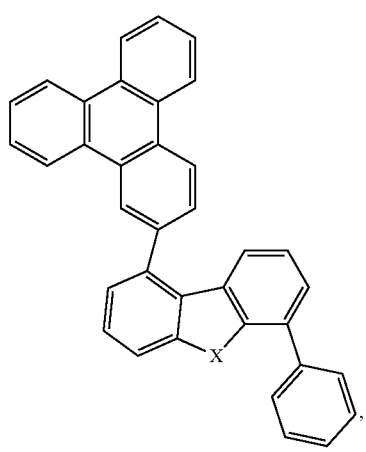
102
-continued
Compound 31
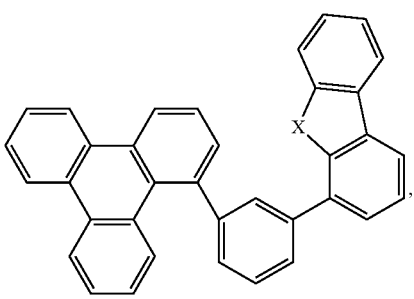
Compound 32
Compound 33

-continued
Compound 34
Compound 35
Compound 36
Compound 37
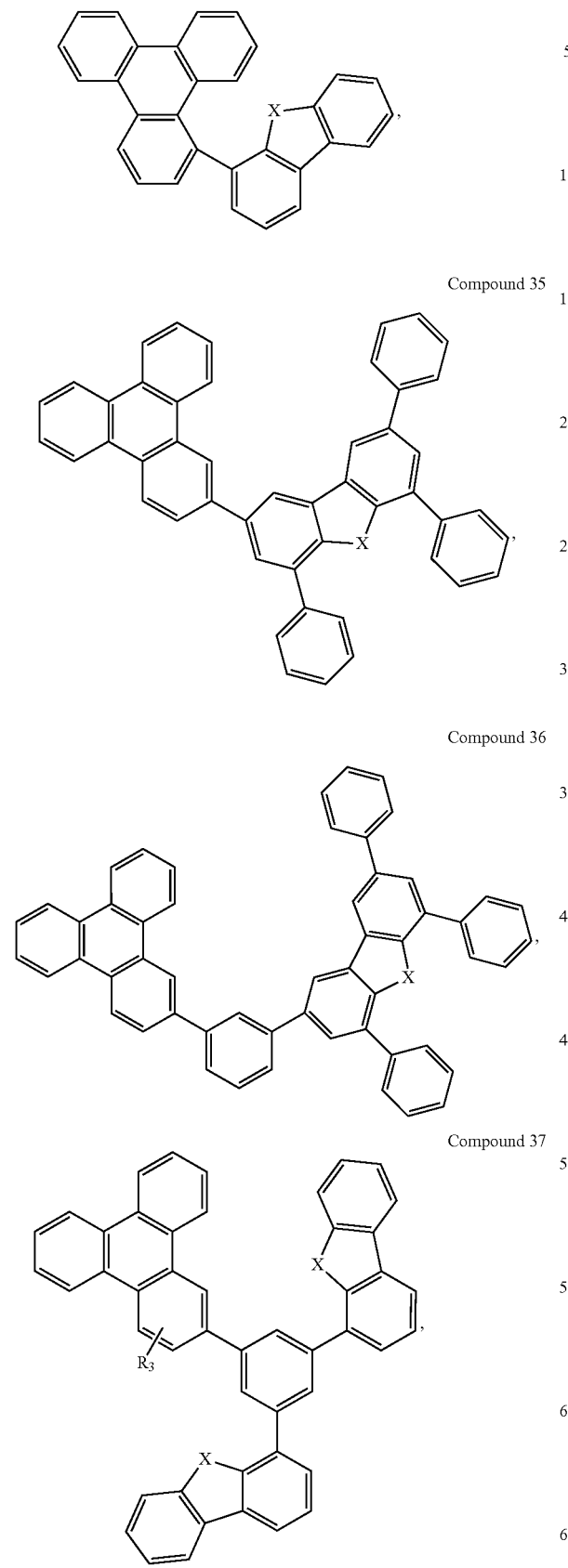
-continued
Compound 38
Compound 39
Compound 40
Compound 41
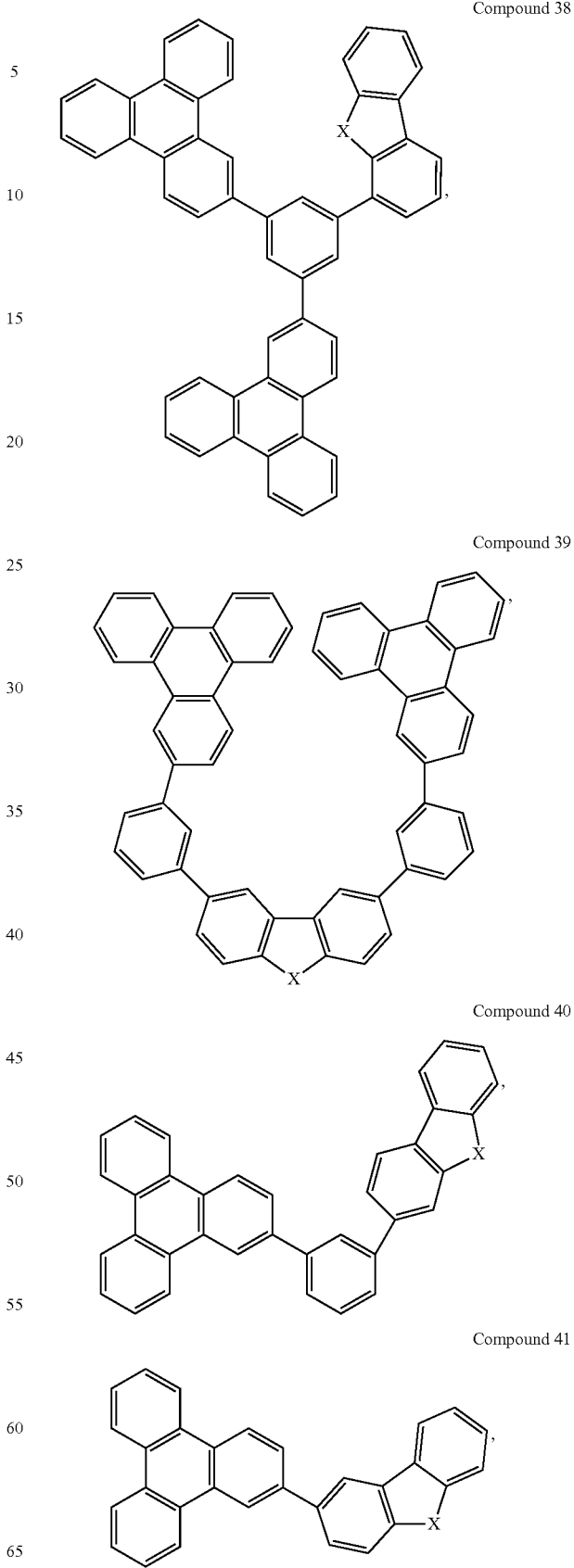

-continued
Compound 42
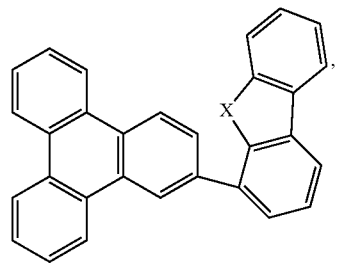
Compound 43
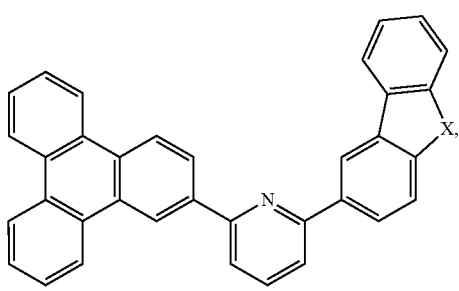
Compound 44
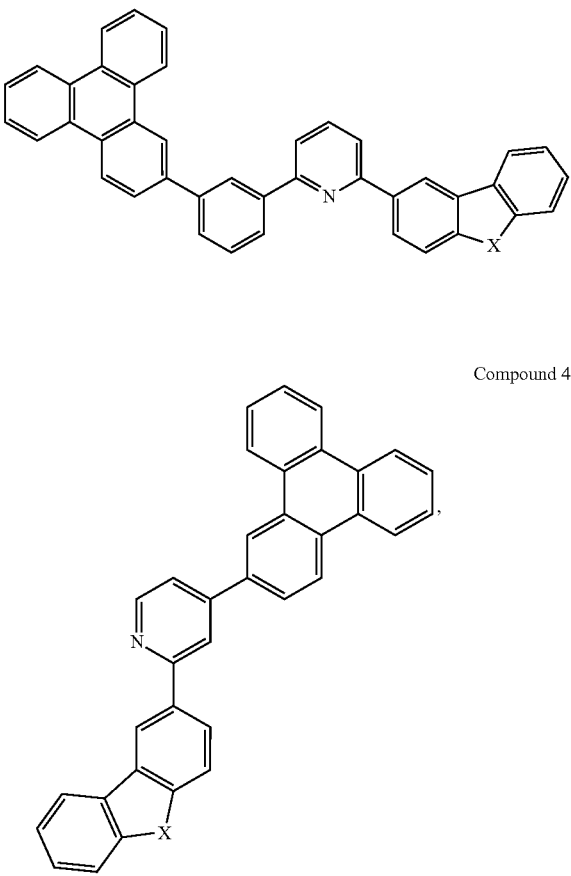
Compound 45
Compound 46
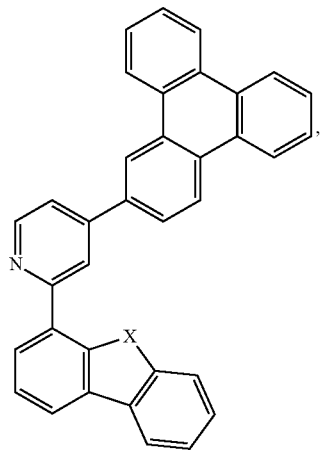
Compound 47
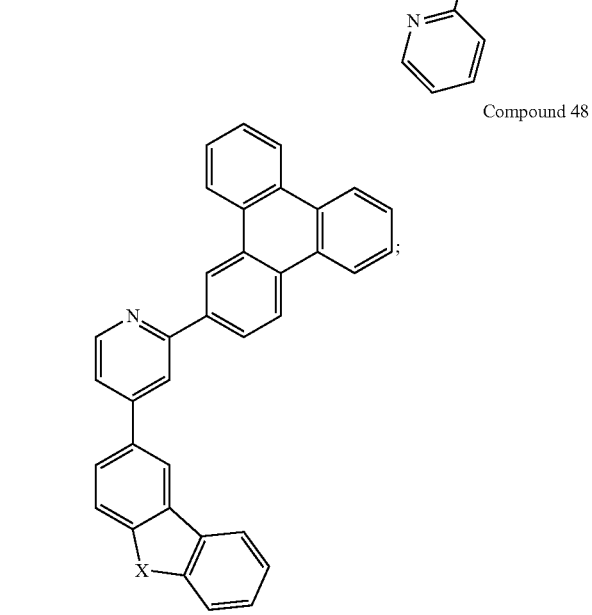
and
Compound 48
and
wherein X is S or O.
13. The compound of claim 12, wherein X is O.
14. The compound of claim 12, wherein X is S.
15. An organic light emitting device, comprising:
an anode;
a cathode; and an organic layer disposed between the anode and the cathode, wherein the organic layer comprises a compound represented by a structure selected from the group consisting of:
Compound 1G
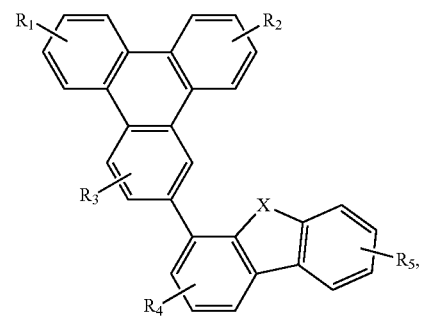
Compound 2G
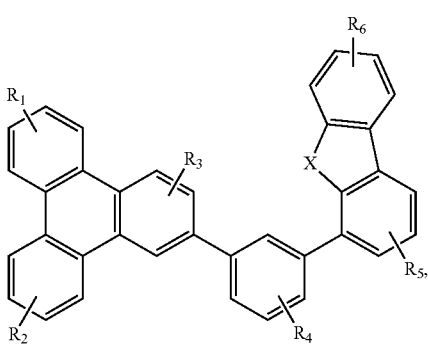
Compound 3G
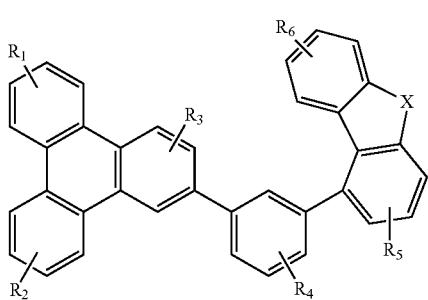
Compound 4G
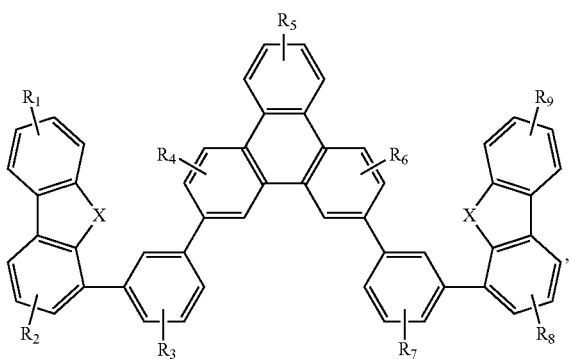
Compound 5G
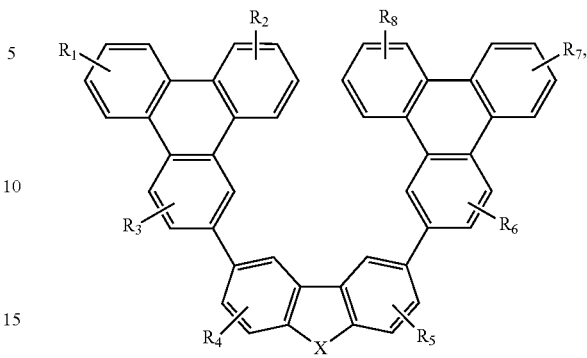
Compound 6G
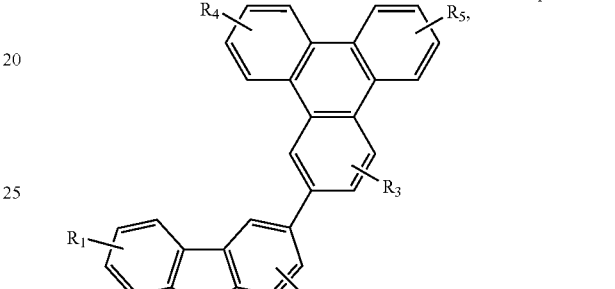
Compound 7G
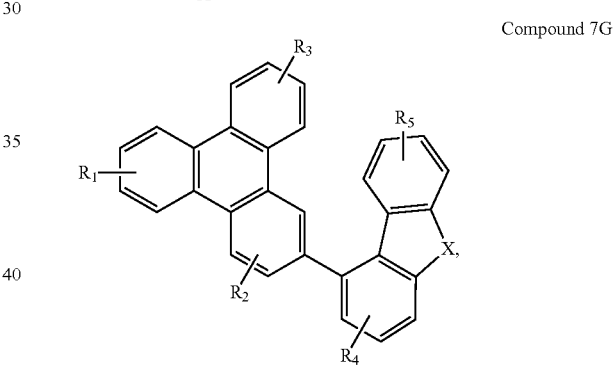
Compound 8G
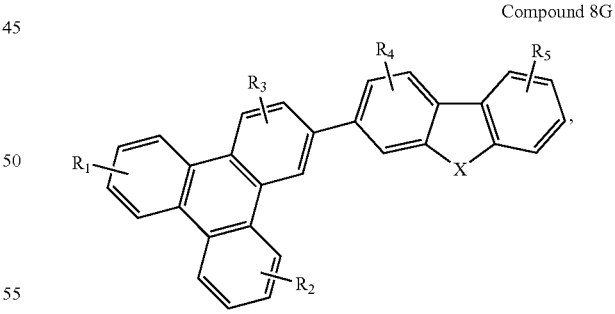
Compound 9G
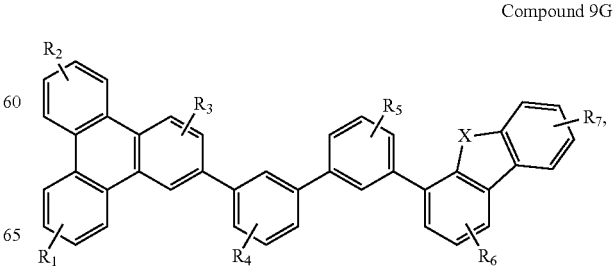

Compound 10G
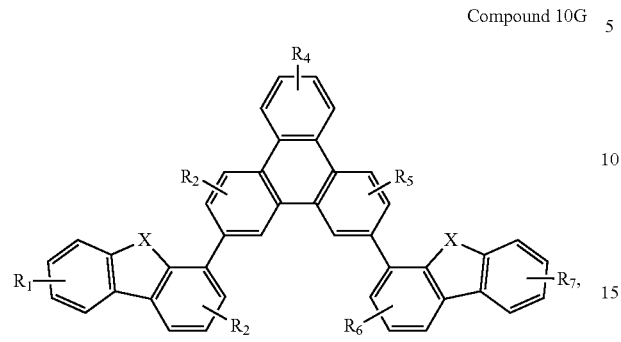
Compound 14G
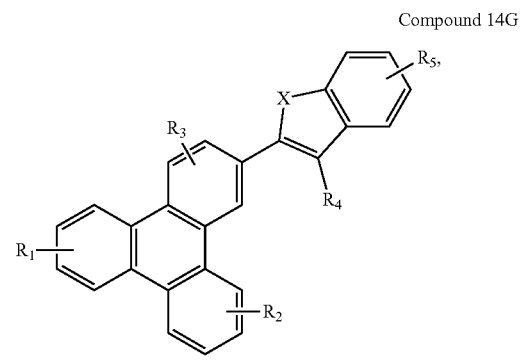
Compound 11G
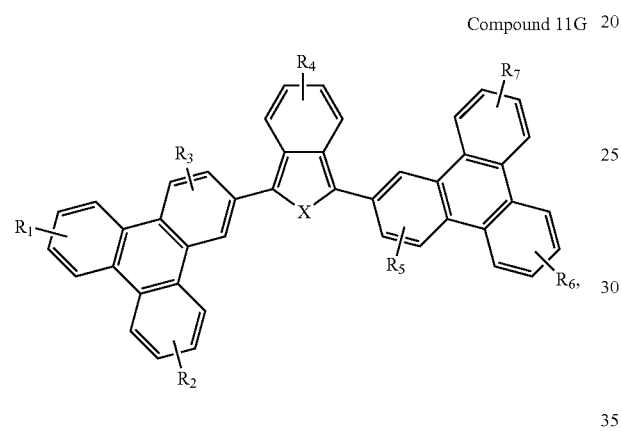
Compound 15G
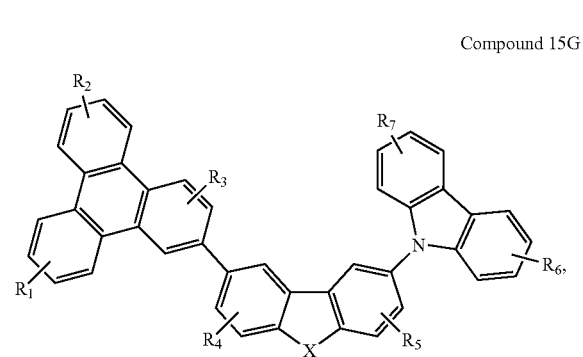
Compound 12G
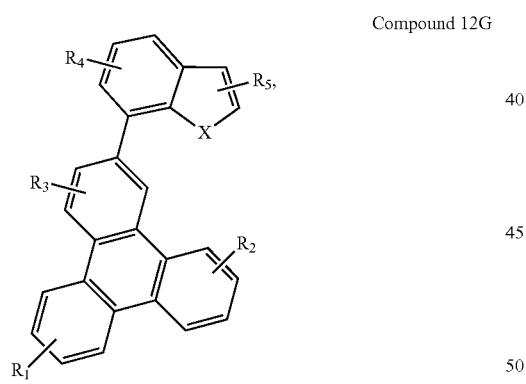
Compound 16G
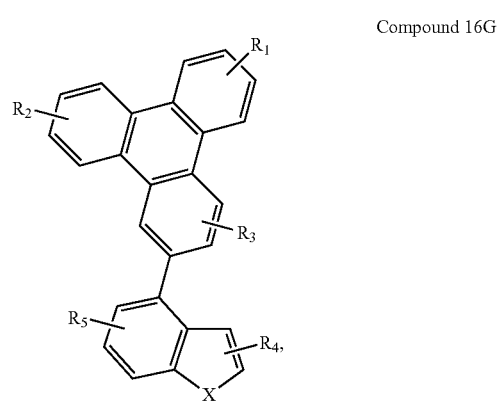
Compound 13G
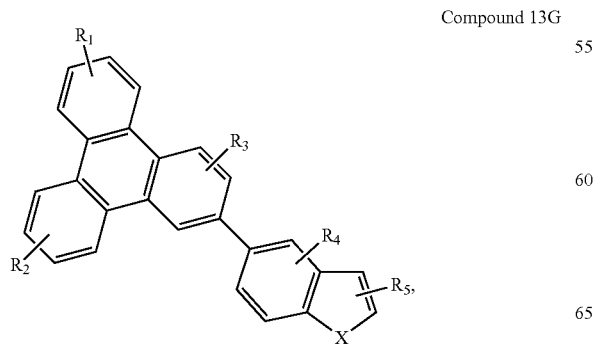
Compound 17G
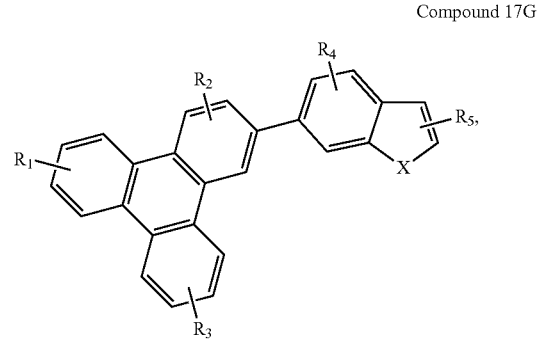

Compound 18G
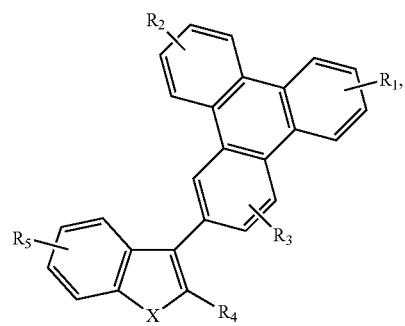
Compound 19G
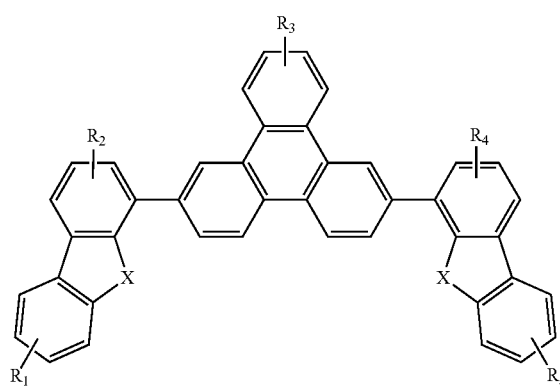
Compound 20G
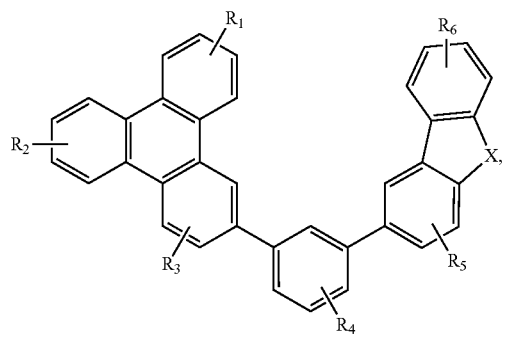
Compound 21G
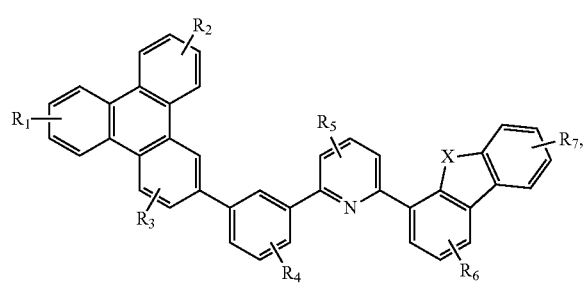
Compound 22G
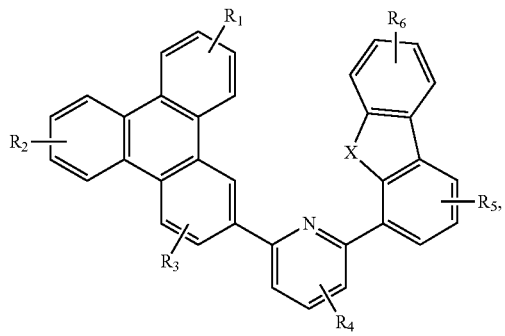
Compound 23G
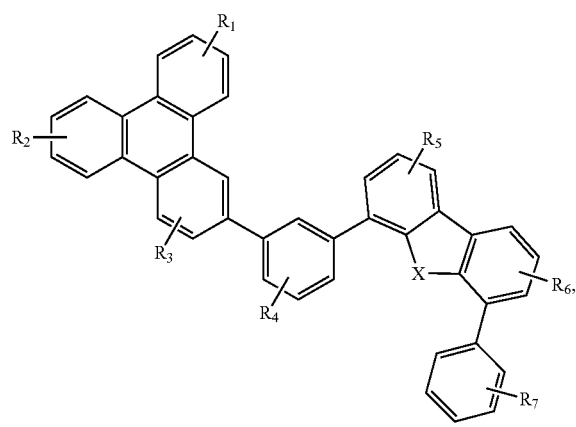
Compound 24G
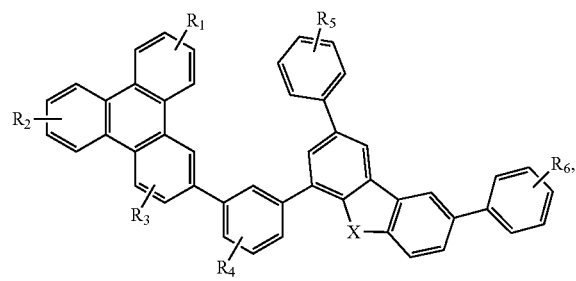
Compound 25G
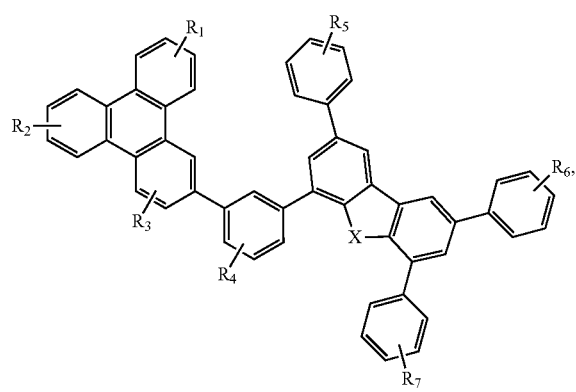

Compound 26G
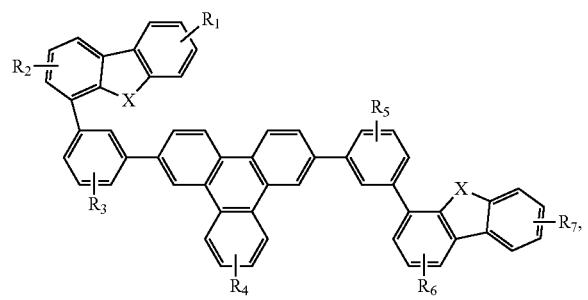
Compound 27G
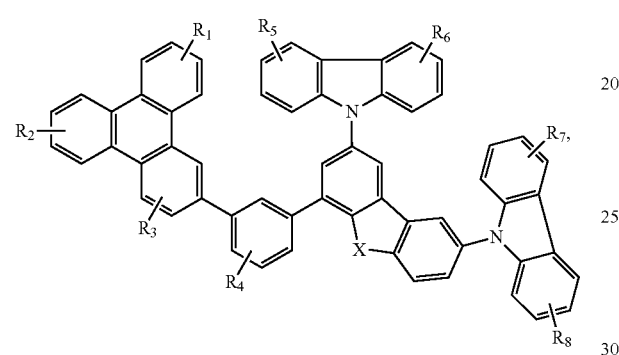
Compound 28G
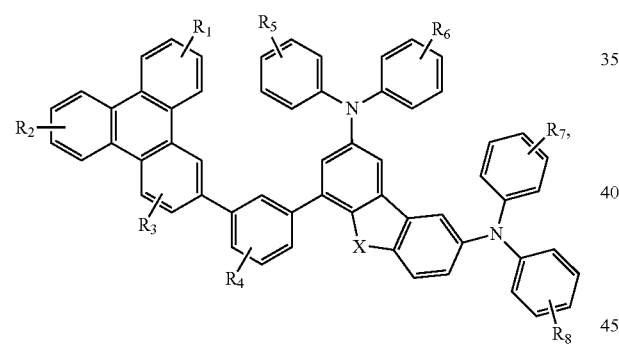
Compound 29G
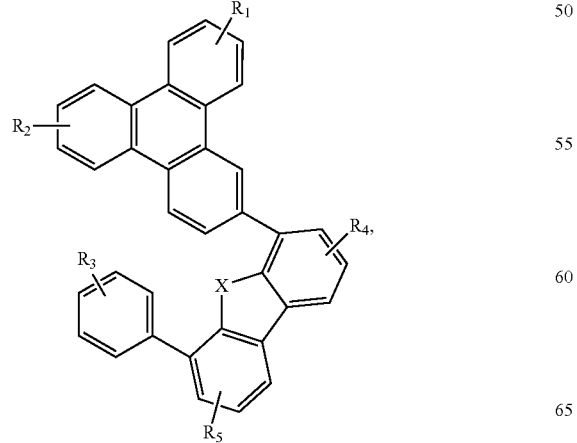
Compound 30G
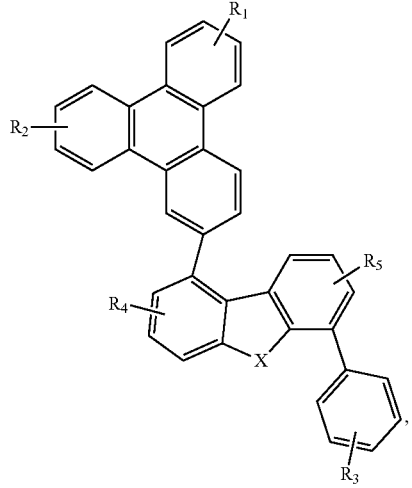
Compound 31G
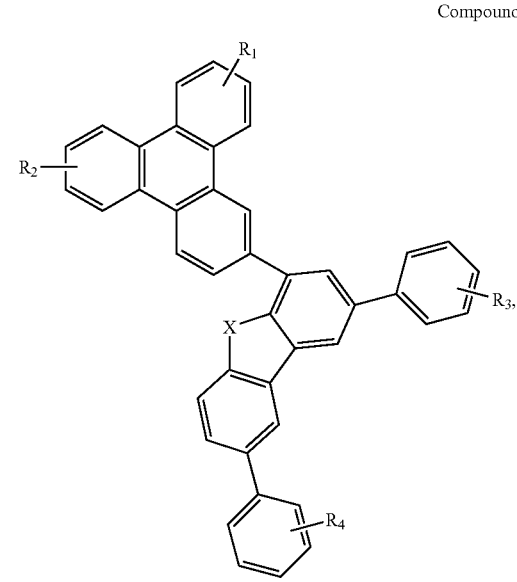
Compound 32G
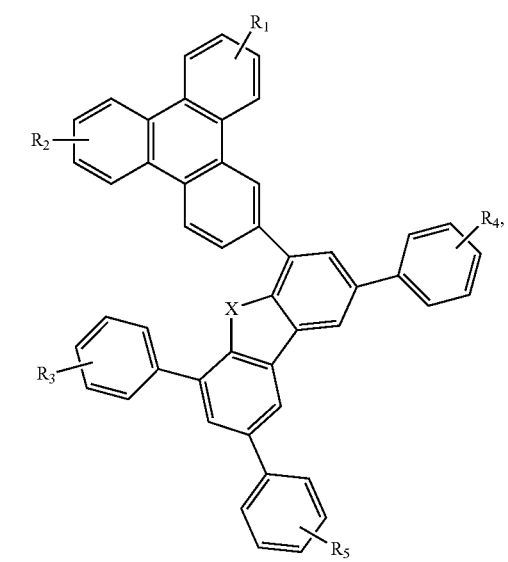

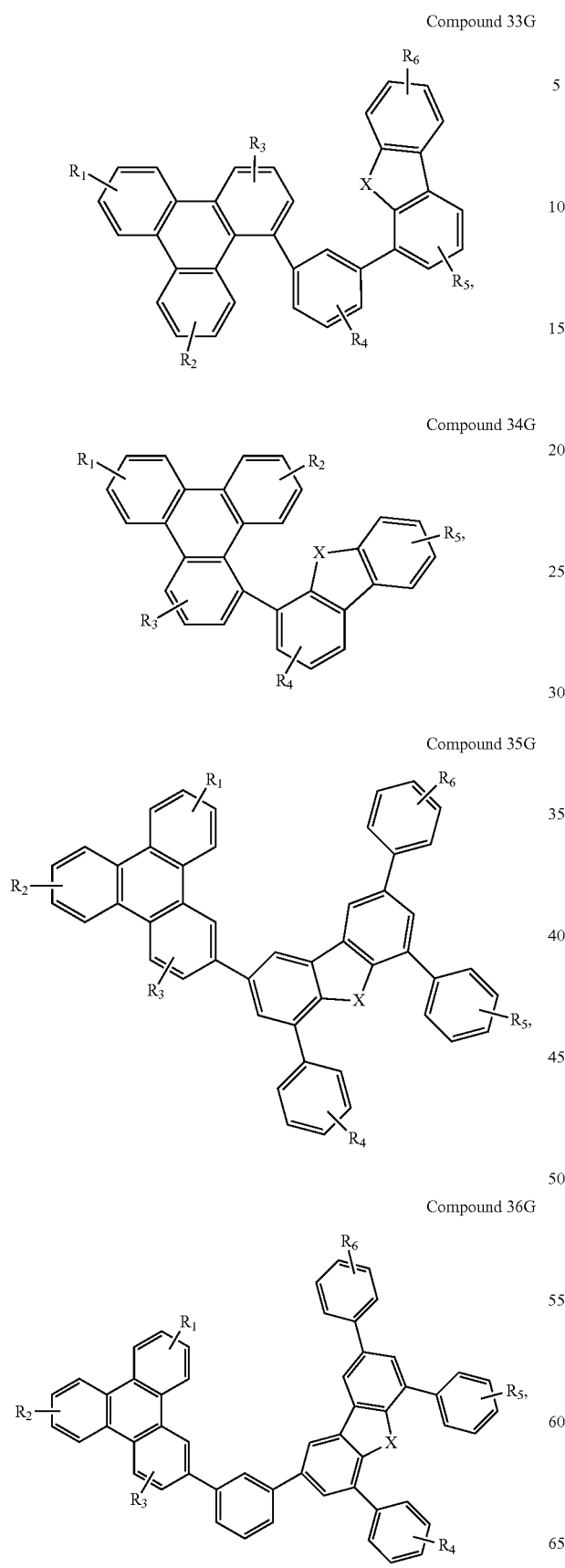
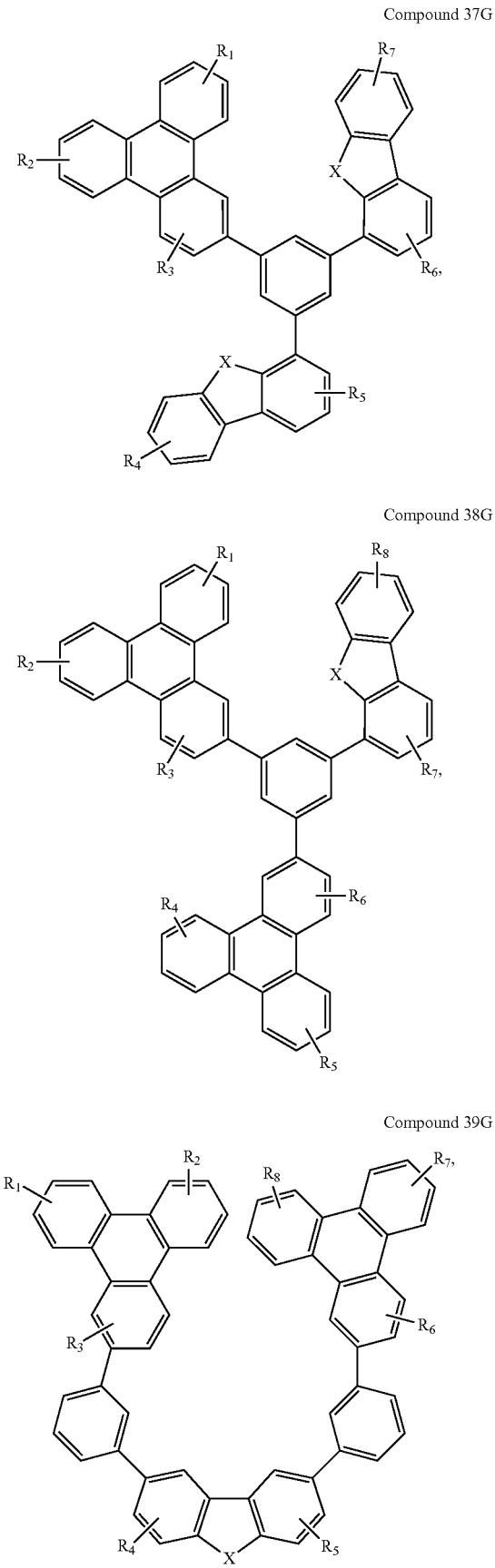

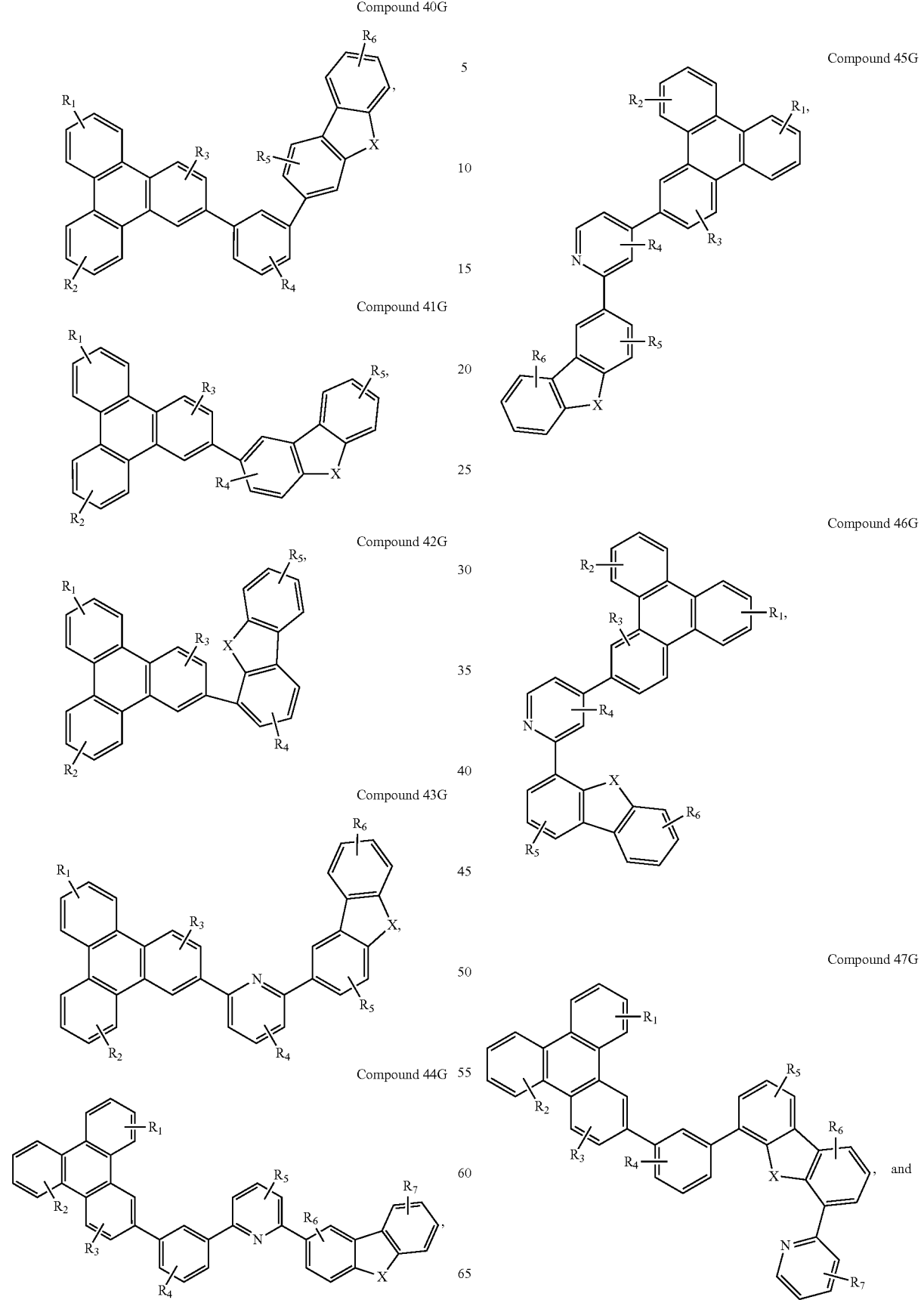

Compound 48G

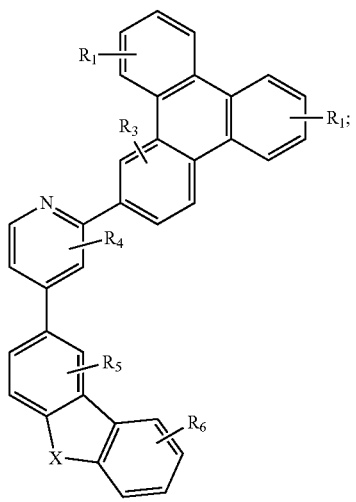

wherein X is S or O;
wherein $R_1$ to $R_9$ are independently selected from the group consisting of hydrogen, alkyl, alkoxy, amino, alkenyl, alkynyl, arylalkyl, aryl, and heteroaryl; and
wherein each of $R_1$ to $R_9$ may represent mono substitutions up to the maximum possible substitutions, or no substitutions.

16. The organic light emitting device of claim 15, wherein the organic layer further comprises a phosphorescent emitter.

17. The organic light emitting device of claim 16, wherein the phosphorescent emitter is an iridium complex.

18. The organic light emitting device of claim 15, wherein the compound is

Compound 1

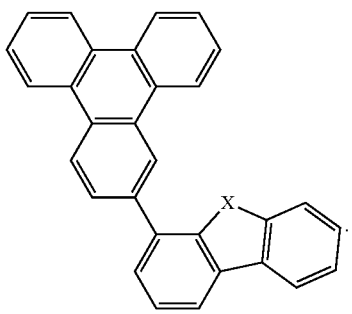

19. The organic light emitting device of claim 15, wherein the compound is

Compound 2

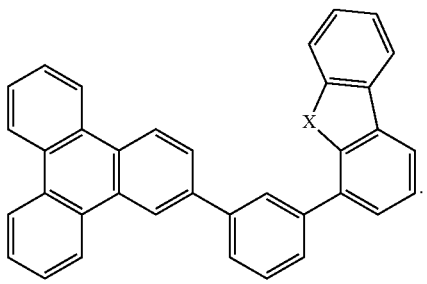

* * * * *

UNITED STATES PATENT AND TRADEMARK OFFICE
CERTIFICATE OF CORRECTION

PATENT NO. : 9,577,200 B2
APPLICATION NO. : 14/838450
DATED : February 21, 2017
INVENTOR(S) : Bin Ma et al.

Page 1 of 4

It is certified that error appears in the above-identified patent and that said Letters Patent is hereby corrected as shown below:

In the Specification

In Column 10, Lines 35-48, please delete

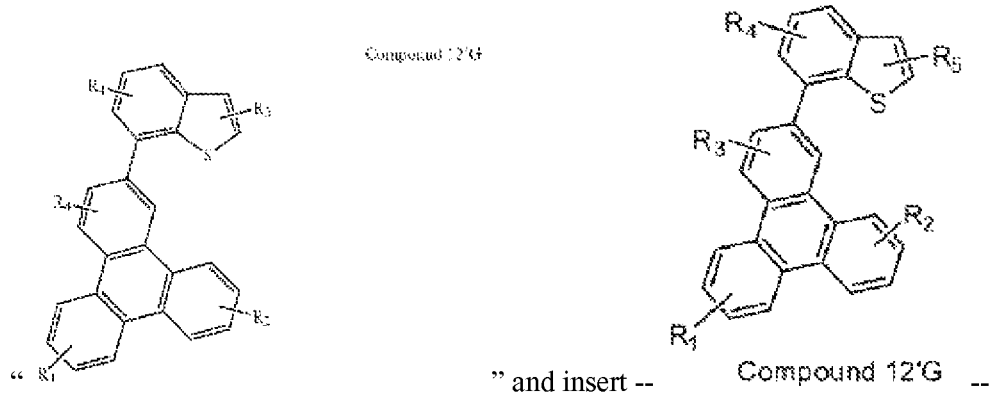

" and insert --    Compound 12'G    --

In Column 11, Lines 1-18, please delete

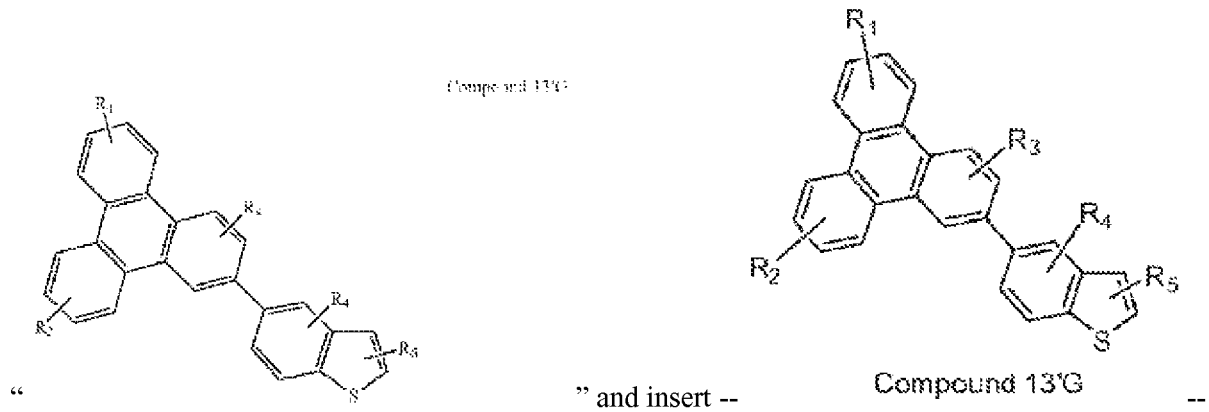

" and insert --    Compound 13'G    --

Signed and Sealed this
Twenty-third Day of May, 2017

Michelle K. Lee
*Director of the United States Patent and Trademark Office*

CERTIFICATE OF CORRECTION (continued)
U.S. Pat. No. 9,577,200 B2

In Column 12, Lines 1-18, please delete " " and insert --

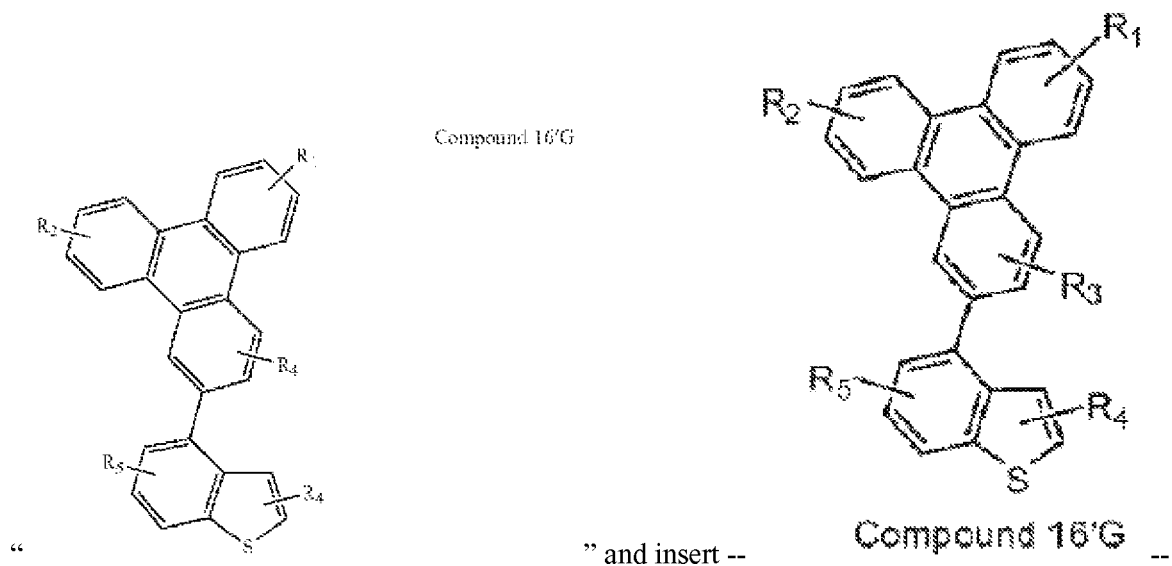

In Column 13, Lines 37-50, please delete " " and insert --

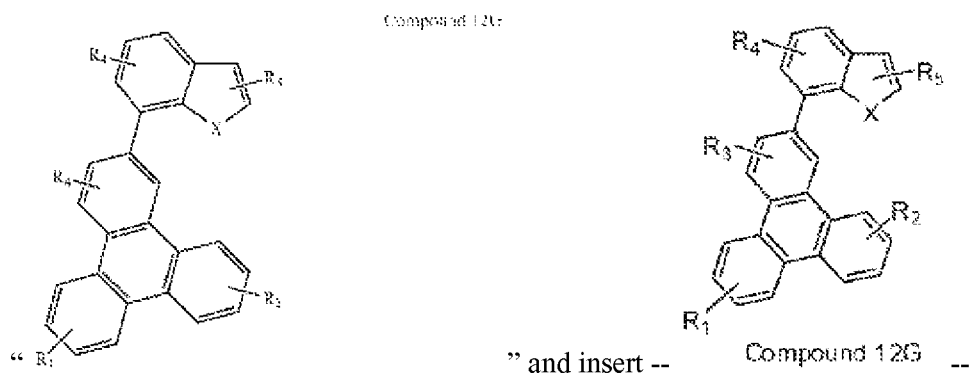

In Column 14, Lines 1-18, please delete " " and insert --

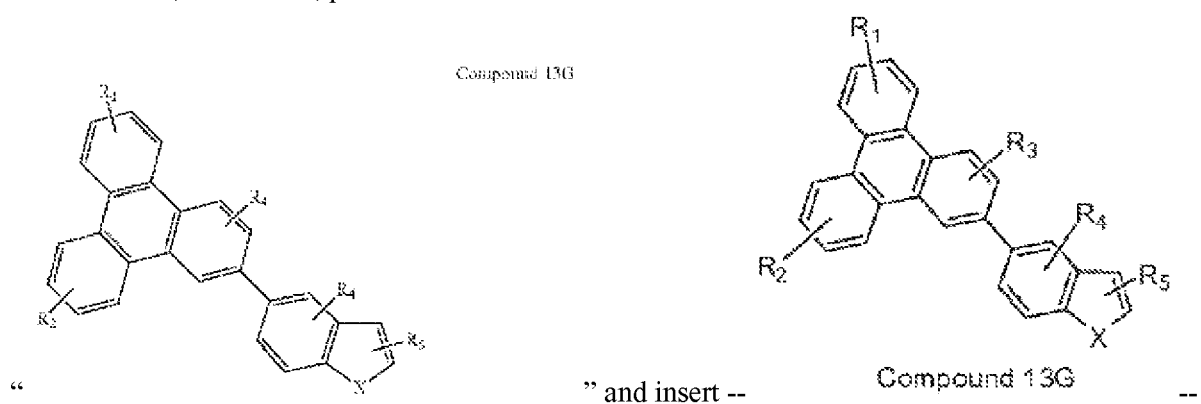

CERTIFICATE OF CORRECTION (continued)
U.S. Pat. No. 9,577,200 B2

In Column 15, Lines 1-19, please delete

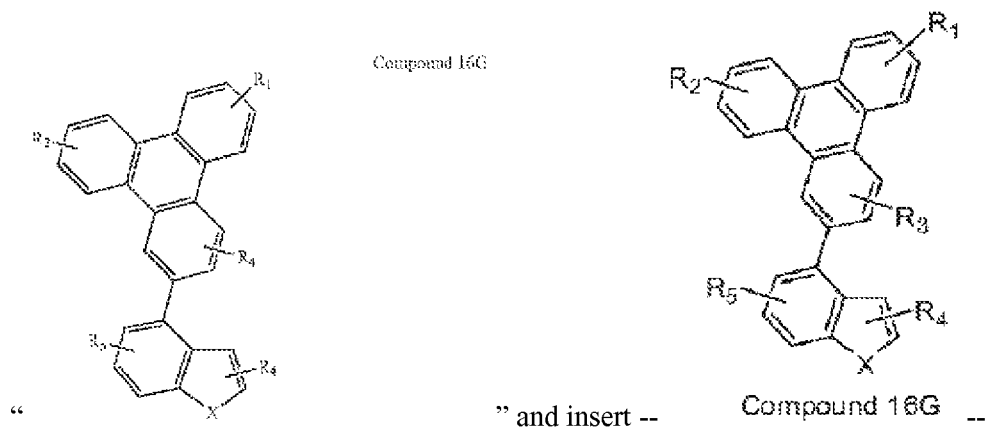

In Column 28, Lines 1-19, please delete

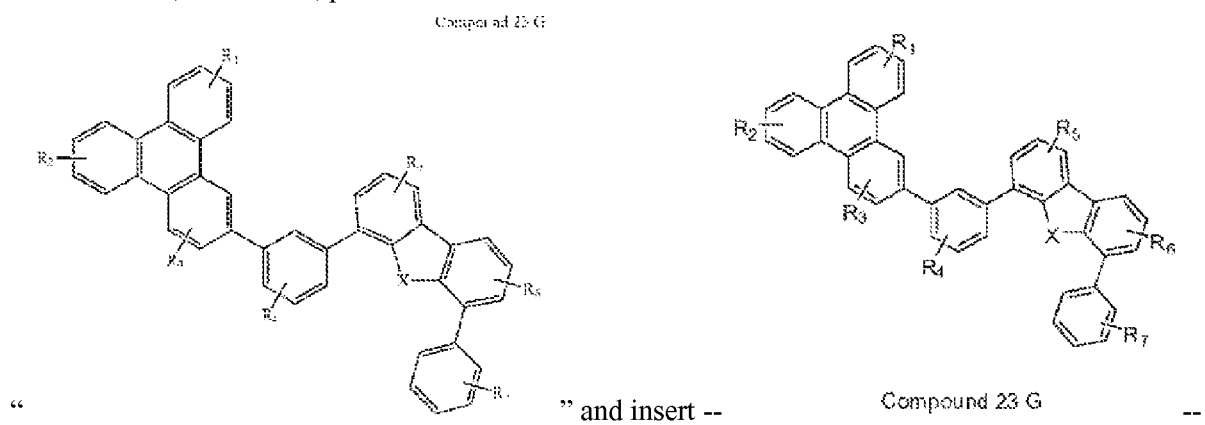

In the Claims

In Claim 1, Column 94, Lines 1-22, please delete

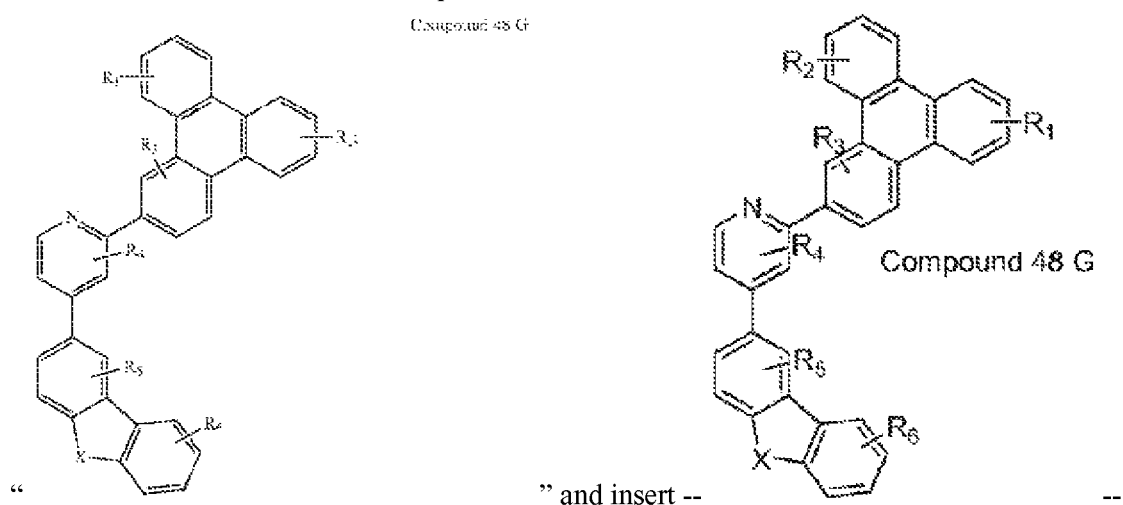

In Claim 8, Column 94, Line 59, please delete "Compound 50" and insert -- Compound 5G --

CERTIFICATE OF CORRECTION (continued)
U.S. Pat. No. 9,577,200 B2

In Claim 15, Column 109, Lines 1-17, please delete " " and insert -- 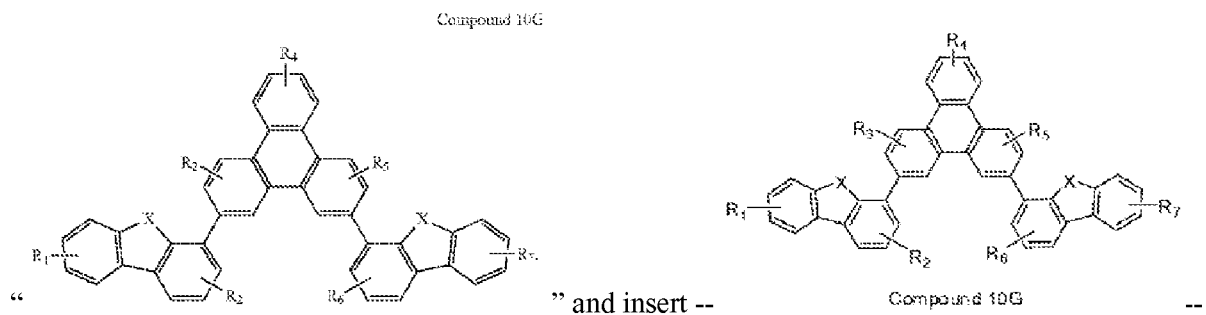 --

In Claim 15, Column 119, Lines 1-22, please delete " " and insert -- 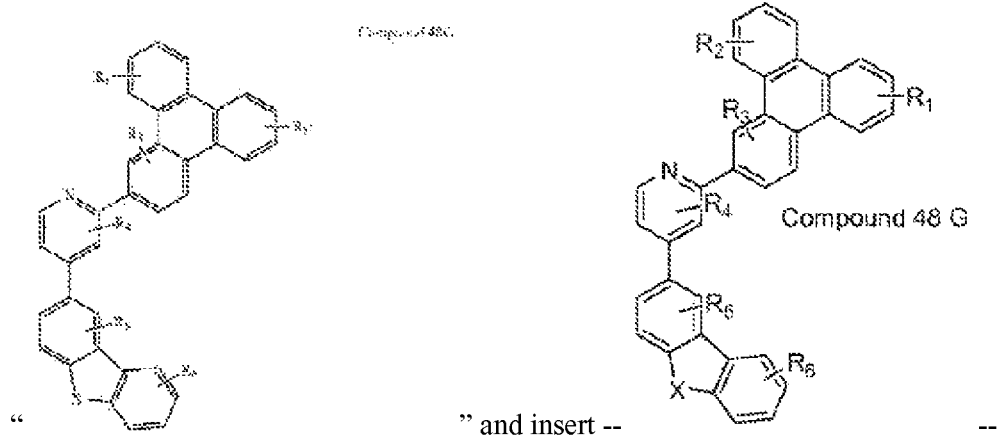 --